(12) United States Patent
Rao et al.

(10) Patent No.: US 10,570,150 B2
(45) Date of Patent: Feb. 25, 2020

(54) 6,7-TRANS CEPHALOSPORIN-BASED PROBES FOR DETECTING BACTERIA EXPRESSING A METALLO-BETA-LACTAMASE

(71) Applicant: The Board of Trustees of the Leland Stanford Junior University, Palo Alto, CA (US)

(72) Inventors: Jianghong Rao, Sunnyvale, CA (US); Haibin Shi, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 183 days.

(21) Appl. No.: 15/111,576

(22) PCT Filed: Jan. 15, 2015

(86) PCT No.: PCT/US2015/011533
§ 371 (c)(1),
(2) Date: Jul. 14, 2016

(87) PCT Pub. No.: WO2015/109056
PCT Pub. Date: Jul. 23, 2015

(65) Prior Publication Data
US 2016/0333027 A1 Nov. 17, 2016

Related U.S. Application Data

(60) Provisional application No. 61/928,524, filed on Jan. 17, 2014, provisional application No. 61/968,404, filed on Mar. 21, 2014.

(51) Int. Cl.
| | | |
|---|---|---|
| *C07D 501/00* | (2006.01) | |
| *C07D 501/48* | (2006.01) | |
| *C07D 277/64* | (2006.01) | |
| *C07D 311/16* | (2006.01) | |
| *C07D 501/26* | (2006.01) | |
| *C12Q 1/34* | (2006.01) | |
| *C12Q 1/66* | (2006.01) | |

(52) U.S. Cl.
CPC ......... *C07D 501/00* (2013.01); *C07D 277/64* (2013.01); *C07D 311/16* (2013.01); *C07D 501/26* (2013.01); *C07D 501/48* (2013.01); *C12Q 1/34* (2013.01); *C12Q 1/66* (2013.01); *G01N 2333/986* (2013.01)

(58) Field of Classification Search
CPC .................................................. C07D 501/00
USPC ....................................................... 549/200
See application file for complete search history.

(56) References Cited

U.S. PATENT DOCUMENTS

| | | |
|---|---|---|
| 5,254,680 A | 10/1993 | Alpegiani et al. |
| 2005/0004367 A1 | 1/2005 | Du et al. |

FOREIGN PATENT DOCUMENTS

| | | |
|---|---|---|
| WO | 2013/173519 A1 | 11/2013 |
| WO | WO2014/111906 A1 * | 7/2014 |

OTHER PUBLICATIONS

King, Chem. Principle and Practice (1994), pp. 20-208.*
Bush, et al., "Updated Functional Classification of β-Lactamases", Antimicrobial Agents and Chemotherapy, Mar. 2010, vol. 54, No. 3, pp. 969-976.
World Health Organization, "Global tuberculosis report 2013", 2013, 306 pages.
Dheda, et al., "Point-of-care diagnosis of tuberculosis: Past, present and future", Respirology, 2013, 18, pp. 217-232.
Gao, et al., "Novel Fluorogenic Substrates for Imaging β-Lactamase Gene Expression", J. Am. Chem. Soc., 2003, 125, 11146-11147.
Keeler, et al., "Reducing the global burden of tuberculosis: the contribution of improved diagnostics", Nature Publishing Group, 2006, pp. 49-57.
Kong, et al., "Imaging tuberculosis with endogenous β-lactamase reporter enzyme fluorescence in live mice", PNAS, Jul. 6, 2010, vol. 107, No. 27, 12239-12244.
McNerney, et al., "Towards a point-of-care test for active tuberculosis: obstacles and opportunities", Nature Reviews, Microbiology, Mar. 2011, vol. 9, pp. 204-213.
Rukavishnikov, et al., "Fluorogenic cephalosporin substrates for β-lactamase TEM-1", Analytical Biochemistry, 2011, 419, pp. 9-16.
Urdea, et al., "Requirements for high impact diagnostics in the developing world", Nature Publishing Group, 2006, pp. 73-79.
Xie, et al., "Rapid point-of-care detection of the tuberculosis pathogen using a BlaC-specific fluorogenic probe", Nat. Chem., Oct. 2012, 4(10), pp. 802-809.

(Continued)

*Primary Examiner* — Taofiq A Solola
(74) *Attorney, Agent, or Firm* — Thomas|Horstemeyer, LLP

(57) ABSTRACT

The present invention discloses a probe useful for the selective detection of metallo-beta-lactamases, in particular carbapenemases, thereby distinguishing those species of bacteria that are carbapenem-resistant from bacterial strains that are sensitive. Cephalospori based probes that have the 6,7 R,R configuration are susceptible to cleavage by beta-lactamases but cannot distinguish between cleavage by metallo-beta-lactamases and other beta-lactamases. By modifying a side group of the cephalosporin, selectivity can be introduced allowing the probes to distinguish between various types of metallo-beta-lactamases.

7 Claims, 37 Drawing Sheets
Specification includes a Sequence Listing.

(56) References Cited

OTHER PUBLICATIONS

Xing, et al., "Cell-Permeable Near-Infrared Fluorogenic Substrates for Imaging β-Lactamase Activity", J. Am. Chem. Soc., 2005, 127, pp. 4158-4159.
Yao, et al., "A Bioluminogenic Substrate for In Vivo Imaging of β-Lactamase Activity", Angew. Chem. Int. Ed., 2007, 46, pp. 7031-7034.
Zhang, et al., "Ratiometric Fluorescence Detection of Pathogenic Bacteria Resistant to Broad-Spectrum β-Lactam Antibiotics", Angew. Chem. Int. Ed., 2012, 51, pp. 1865-1868.
Zlokarnik, et al., "Quantitation of Transcription and Clonal Selection of Single Living Cells with β-Lactamase as Reporter", Science, Jan. 2, 1998, vol. 279, pp. 84-88.
Arakawa, et al., "Convenient Test for Screening Metallo-β-Lactamase-Producing Gram-Negative bacteria by Using Thiol Compounds", Journal of Clinical Microbiology, Jan. 2000, vol. 38, No. 1, pp. 40-43.
Arnold, et al., "Emergence of Klebsiella pneumoniae Carbapenesmase (KPC)—Producing Bacteria", South Med J, Jan. 2011, 104(1), 40-45.
Avlami, et al., "Detection of metallo-β-lactamase genes in clinical specimens by a commerical multiplex PCR system", Journal of Microbiological Methods, 83, 2010, 185-187.
Backus, et al., "Uptake of unnatural trehalose analogs as a reporter for *Mycobacterium* tuberculosis", Nat Chem Biol., Apr. 2011, 7(4), 228-235.
Basker, et al., "Comparative Antibacterial Properties In Vitro of Seven Olivanic Acid Derivatives: MM 4550, MM 13902, MM 17880, MM 22380, MM 22381, MM 22382 and MM 22383", The Journal of Antibiotics, Aug. 1980, 378-884.
Beatty, et al., "Sulfatase-activated fluorophores for rapid discrimination of mycobacterial species and strains", PNAS, Aug. 6, 2013, vol. 110, No. 32, pp. 12911-12916.
Behr, et al., "Transmission of *Mycobacterium* tuberculosis from patients smear-negative for acid-fast bacilli", The Lancet, vol. 353, Feb. 6, 1999, 444-449.
Bernabeu, et al., "Spectrophotometry-based detection of carbapenemase producers among Enterobacteriaceae", Diagnostic Microbiology and Infections Disease, 2012, 74, 88-90.
Bradley, et al., "Carbapenems in Clinical practice: a guide to their use in serious infection", International Journal of Antimicrobial Agents, 1999, 11, 93-100.
Boyd, et al., "Electronic Structures of Cephalosporins and Penicillins. 9. Departure of a Leaving Group in Dephalosporins", Journal of Medicinal Chemistry, 1979, vol. 22, No. 7, pp. 778-784.
Burckhardt, et al., "Using Matrix-Assisted Laser Desorption Ionization-Time of Flight Mass Spectrometry to Detect Carbapenem Resistance within 1 to 2.5 Hours", Journal of Clinical Microbiology, Sep. 2011, vol. 49, No. 9, pp. 3321-3324.
Cepheid, Xpert MTB/RIF, 2015, 2 pages.
Chang, et al., "Rapid and effective diagnosis of tuberculosis and rifampicin resistance with Xpert MTB/RIF assay: A meta-analysis", Journal of Infection, 2012, 64, 580-588.
Dye, et al., "Measuring tuberculosis burden, trends and teh impact of control programmes", Lancet Infect. Dis, 2008, 8, 233-243.
Cohen Stuart, et al., "Guideline for phenotypic screening and confirmation of carbapenemases in Enterobacteriaceae", International Journal of antimicrobial Agents, 2010, 36, 205-210.
Crompton, et al., "β-Lactamase inhibitors, the inhibition of serine β-lactamases by specific boronic acids", Biochem J., 1988, 251, 453-459.
Doherty, et al., "Inhibition of Human Leukocyte Elastase. 1. Inhibition by C-7Substituted Cephalosporin tert-Bytyl Esters", Journal of Medicinal Chemistry, 1990, vol. 33, No. 9, 2513-2521.
Dortet, et al., "Rapid Detection of Carbapenemase-Producing Pseudomonas spp." Journal of Clinical Microbiology, Nov. 2012, vol. 50, No. 11, pp. 3773-3776.
Dortet, et al., "Rapid Identification of Carbapenemase Types in Enterobacteriaceae and Pseudomonas spp. By Using a Biochemical Test" Antimicrobial Agents and Chemotherapy, Dec. 2012, vol. 56, No. 12, pp. 5437-6440.
Falzon, et al., "WHO guidelines for the programmatic management of drug-resistant tuberculosis: 2011 update", Eur Respir J, 2011, 38, 516-528.
Flores, et al., "Genetic analysis of the β-lactamase of *Mycobacterium* tuberculosis and *Mycobacterium* smegmatis and susceptibility to β-lactam antibiotics", Microbiology, 2005, 151, 521-532.
Greco, et al. "Current evidence on diagnostic accuracy of commercially based nucleic acid amplification tests for teh liagnosis of pulmonary tuberculosis", Thorax, 2006, 61, 783-790.
Griffin, et al., "Structural and Kinetic Studies on Metallo-β-lactamase IMP-1", American Chemical Society, Biochemistry, 2011, 50, 9125-9134.
Hughes, et al., "The cost effectiveness of Nucleic Acid Amplification Techniques for the diagnosis of tuberculosis", SciVerse ScienceDirect, Respiratory Medicine, 2012, 106, 300-307.
Ioerger, et al., "The non-clonality of drug resistance in Beijing-genotype isolates of *Mycobacterium* tuberculosis from the Western Cape of South Africa", BMC Genomics, 2010, 11670, 14 pages.
Jacobson, et al., "Treatment Outcomes among Patients with Extensively Drug-Resistant Tuberculosis: Systematic Review and Meta-Analysis", CID, 2010:51, 9 pages.
Kwon, et al., "Distribution and characterization of β-lactamases of mycobacteria and related organisms", Tubercle and Lung Disease, 1995, 76, 141-148.
Lee, et al., "Evaluation of the Hodge Test and the Imipenem-EDTA Double-Disk Synergy Test for Differentiating Metallo-β-Lactamase-Producing Isolates of Pseudomonas spp. and Acinetobacter spp.", Journal of Clinical Microbiology, Oct. 2003, p. 4623-4629.
Nordmann, et al., "Global Spread of Carbapenemase-producing Enterobacteriaceae", Emerging Intectious Diseases, Oct. 2011, vol. 17, No. 10, pp. 1791-1798.
Nordmann, et al., "Identification and screening of carbapenemase-producing Enterobacteriaceae", Clin Microbiol Infect, 2012; 18, pp. 432-438.
Nordmann, et al., "Rapid Detection of Carbapenemase-producing Enterobacteriaceae", Emerging Infectious Diseases, Sep. 2012, vol. 18, No. 9, pp. 1503-1507.
Minion, et al., "Diagnosing tuberculosis with urine lipoarabinomannan: systematic review and meta-analysis", Eur Respir J., 2011, 38, pp. 1398-1405.
Miriagou, et al., "Acquired carbapenemases in Gram-negative bacterial pathogens: detection and surveillance issues", Clin Microbiol Infect, 2010, 16, pp. 112-122.
Oelschlaeger, et al., "Evolving Carbapenemases: Can Medicinal Chemists Advance One Step Ahead of the Coming Strom?", Journal of Medicinal Chemistry Perspective, 2010, 53, pp. 3013-3027.
Palmer, et al., "Nutritional Cues Control Pseudomonas aeruginosa Multicellular Behavior in Cystic Fibrosis Sputum", Journal of Cacteriology, Nov. 2007, vol. 189, No. 22, pp. 8079-8087.
Papp-Wallace, et al., "Carbapenems: Past, Present, and Future", Antimicrobial Agents and Chemotherapy, Nov. 2011, vol. 55, No. 11, pp. 4943-4960.
Poirel, et al., "Multiplex PCR for detection of acquired carbapenemase genes", ScienceDirect, Diagnostic Microbiology and Infections Disease, 2011, 70, pp. 119-123.
Queenan, et al., "Carbapenemases: the Versatile β-Lactamases", Clinical Microbiology Reviews, Jul. 2007, vol. 20, No. 3, pp. 440-458.
Richard, et al., "Pseudomonas aeruginosa Outbreak in a Burn Unit: role of Antimicrobials in the Emergence of Multiply resistant Strains", the Journal of Infections Diseases, 1994, 170, pp. 377-383.
Rupp, et al., "Extended Spectrum β-Lactamase (ESBL)-Producing Enterobacteriaceae", Drugs, 2003, 63 (4), pp. 353-365.
Spellberg, et al., "The Future of Antiobiotics and Resistance", N Engl J Med, Jan. 24, 2013, 368;4, pp. 299-302.
Steingart, et al., "Fluorescence versus conventional sputum smear microscopy for tuberculosis: a systematic review", Lancet Infect Dis, 2006, 6, pp. 570-581.
Swarts, et al., "Probing the Mycobacterial Trehalome with Bioorthogonal Chemistry", Journal of the American Chemical Society, 2012, 134, pp. 16123-16126.

(56) References Cited

OTHER PUBLICATIONS

Udwadia, et al., "Totally Drug-Resistant Tuberculosis in India", CID, 2012, 54, pp. 579-581.
Urano, et al., "Evolution of Fluorescein as a Platform for Finely Tunable Fluorescence Probes", J. Am. Chem. Soc., 2005, 127, pp. 4888-4894.
Voladri, et al., "Recombinant Expression and Characterization of the Major β-Lactamase of *Mycobacterium* tuberculosis", Antimicrobial Agents and Chemotherapy, Jun. 1998, vol. 42, No. 6, p. 1375-1381.
Walsh, et al., "Metallo-β-Lactamases: the Quiet before the Storm?" Apr. 2005, vol. 18, No. 2, pp. 306-325.
Watanabe, et al., "Multicolor Protein Labeling in Living Cells Mutant β-Lactamase-Tag Technology", Bioconjugate Chem., 2010, 21, pp. 2320-2326.
Yang, et al., "Using β-Lactamase to Trigger Supramolecular Hydrogelation", J. Am. Chem. Soc., 2007, 129, 266-267.
Zumla, et al., "Tuberculosis", New England Journal of Medicine, Feb. 21, 2013, 368;8, pp. 745-755.
Office Action for Chinese Patent Application 201580004972.0 dated Mar. 20, 2018.
Alpegiani, et al. (1991) "Stereoselective Alkoxy-De-Amination of 7β-Amino-3-Deacetoxycephalosporanic Acid". Tetrahedron Letters. 32(31): 3883-3886.
Zhang, et al. (2013) "A novel fluorogenic substrate for dinuclear ZN(II)-containing metallo-β-lactamases". Bioorganic & Medicinal Chemistry Letters. 23: 1676-1679.
van Berkel, et al. (2013) "Assay Platform for Clinically Relevant Metallo-β-lactamases". J. Med. Chem. 56: 6945-6953.
International Search Report for PCT/US2015/011533 dated Apr. 7, 2015.
Van Berkel et al. Assay Platform for Clinically Relevant Metallolactamases in Journal of Medicinal Chemistry, 2003, vol. 56, pp. 6945-6953.
Zhang et al. A novel fluorogenic substrate for dinuclear Zn(II}-containing metallo-beta-lactamases in Bioorganic & Medicinal Chemistry Letters 23 (2013) 1676-1679.
Cheng, et al., Fluorogenic Probes with Substitutions at the 2 and 7 Positions of Cephalosporin are Highly BlaC-Specific for Rapid *Mycobacterium* tuberculosis Detection, Angewandte Communications, Angew. Chem. Int. Ed., 2014, 53, pp. 9360-9364.

\* cited by examiner

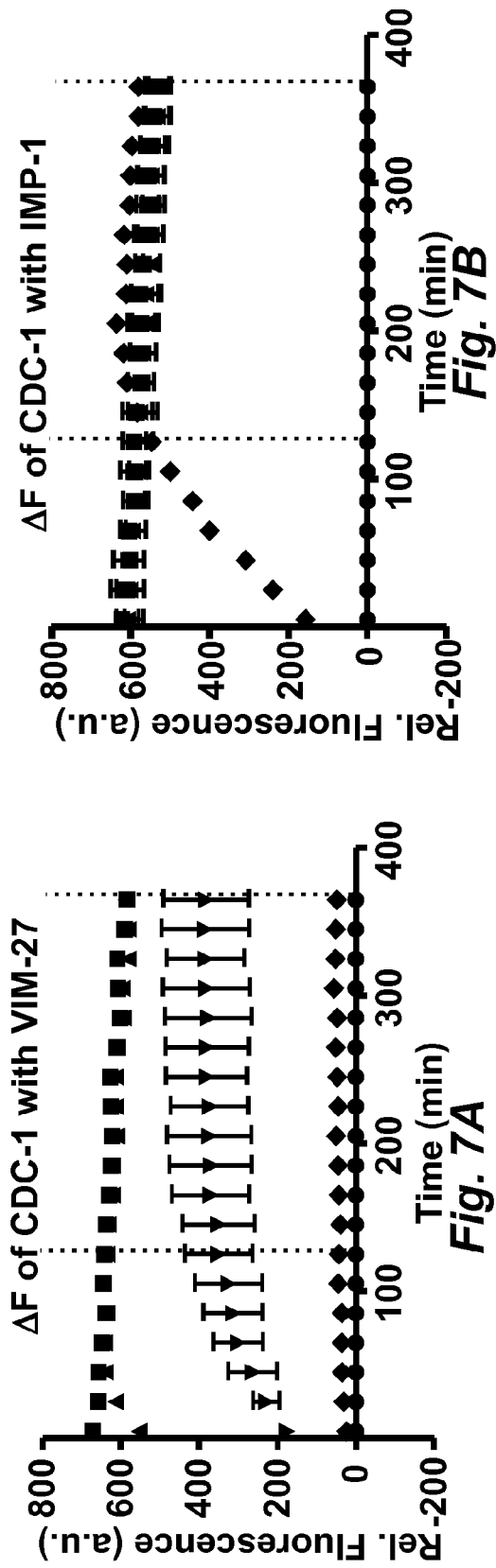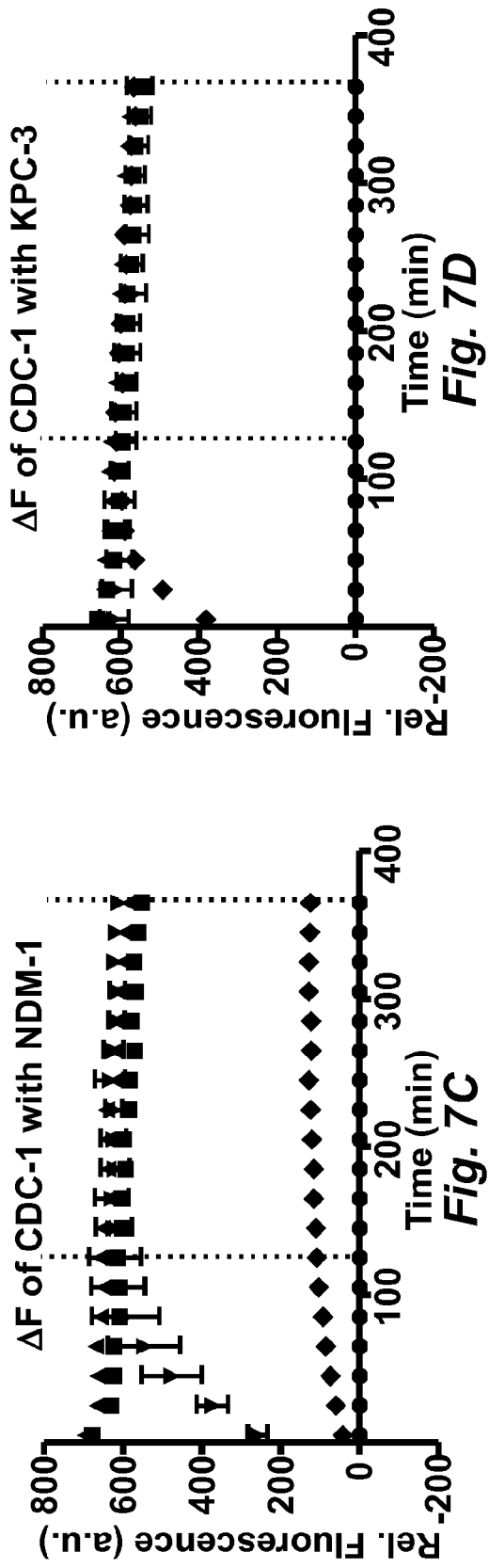
Fig. 7A  Fig. 7B  Fig. 7C  Fig. 7D

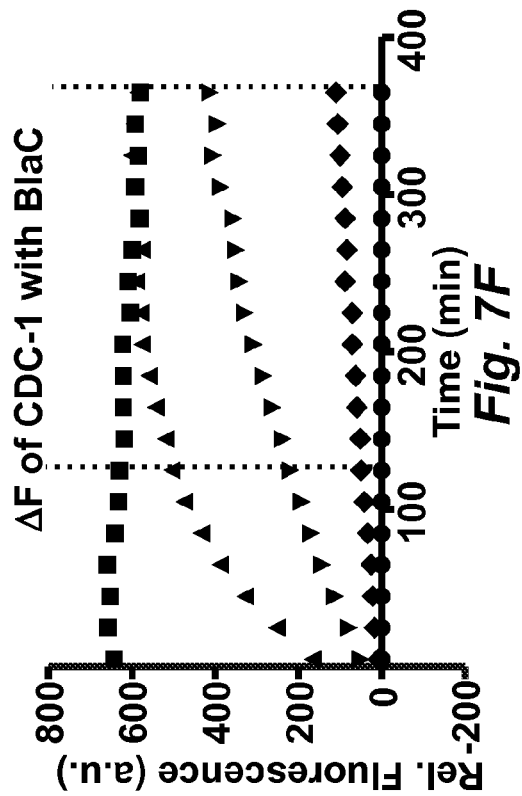
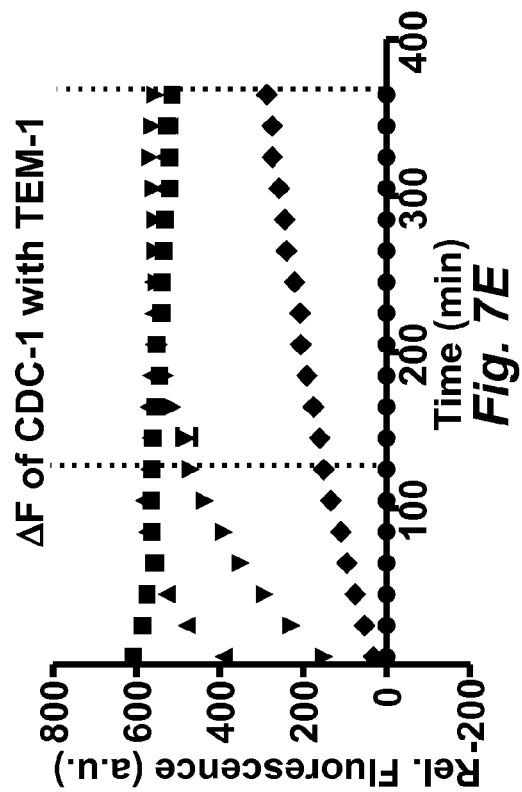
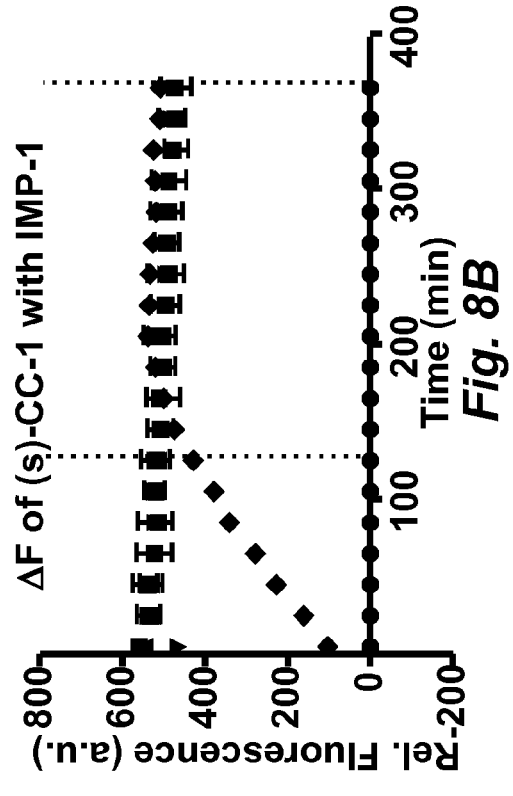
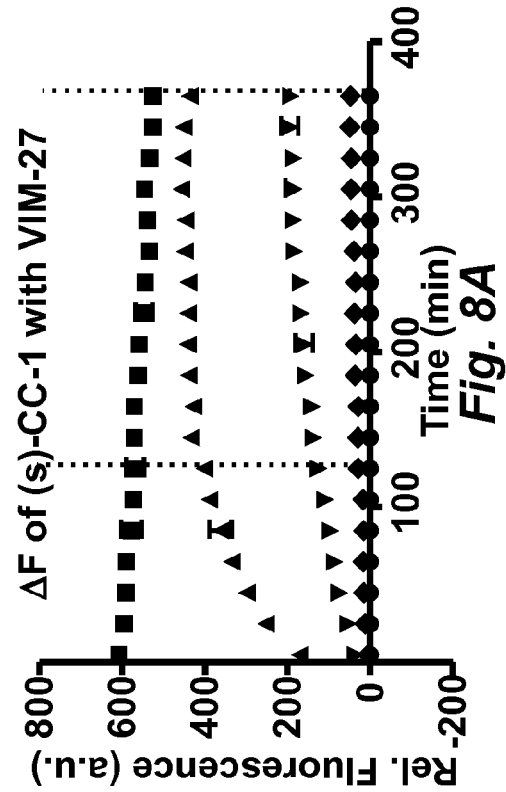

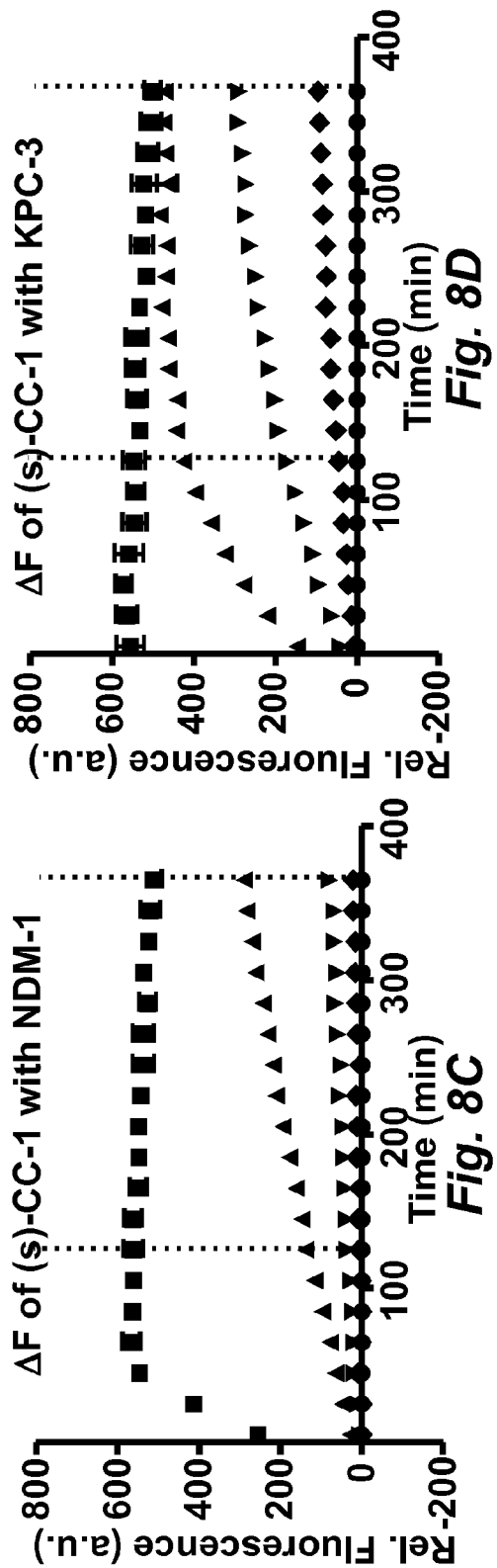
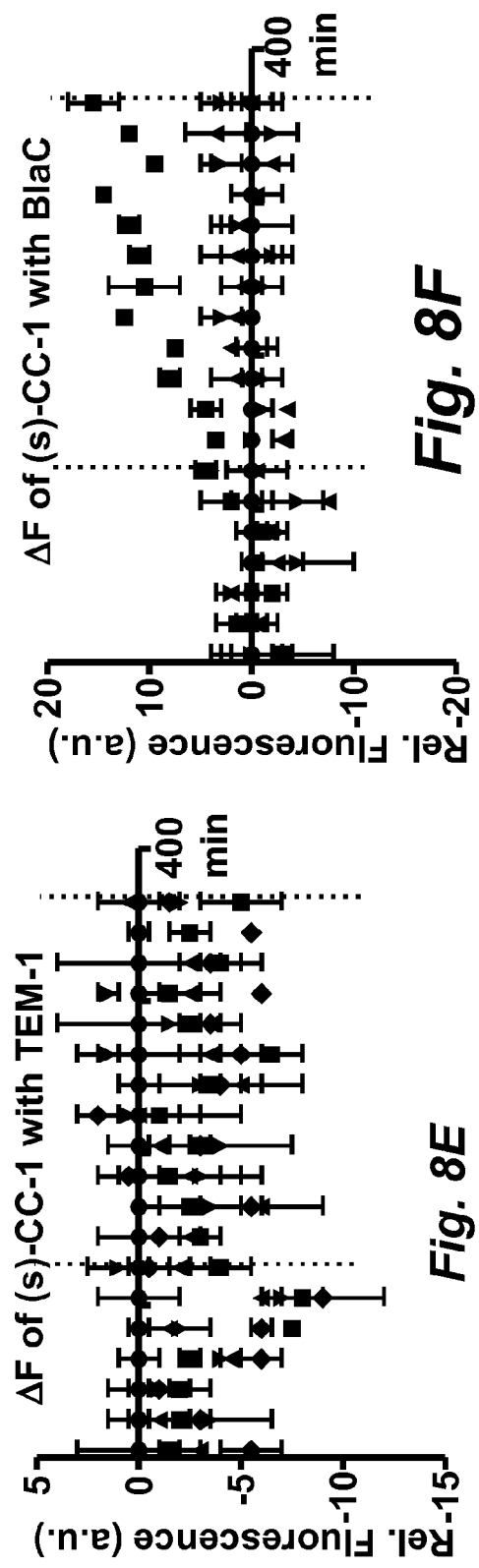

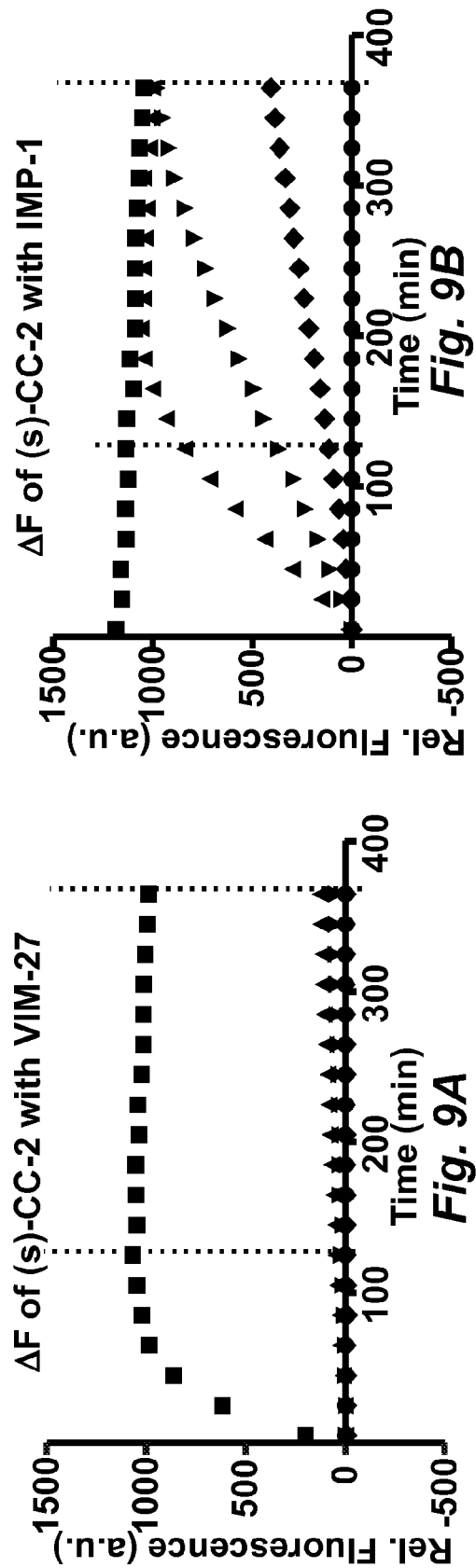
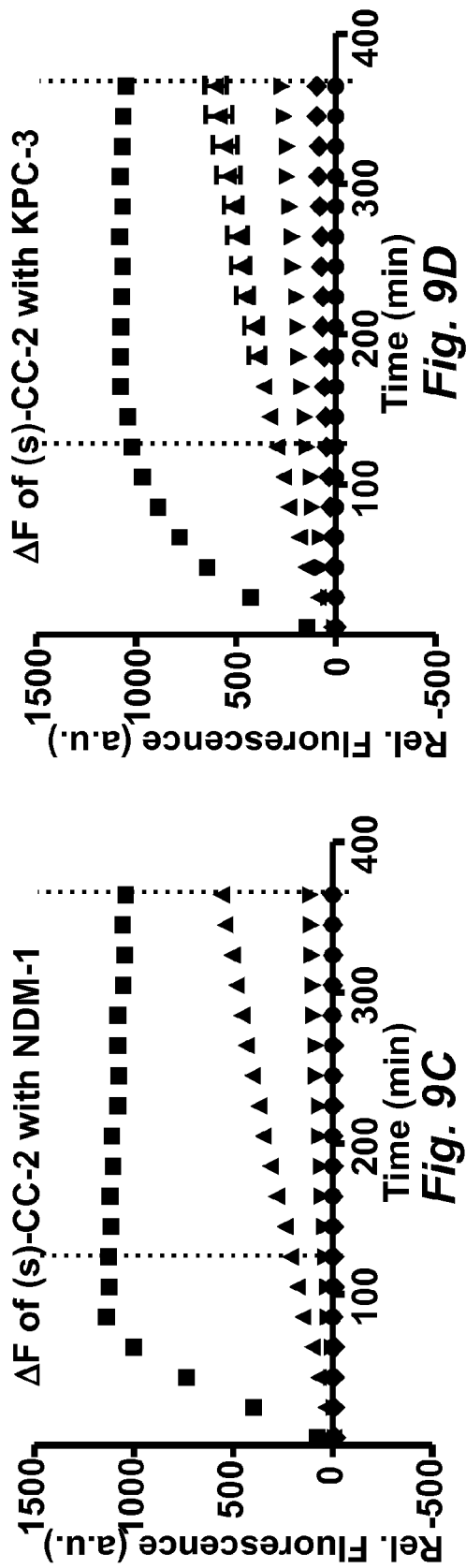

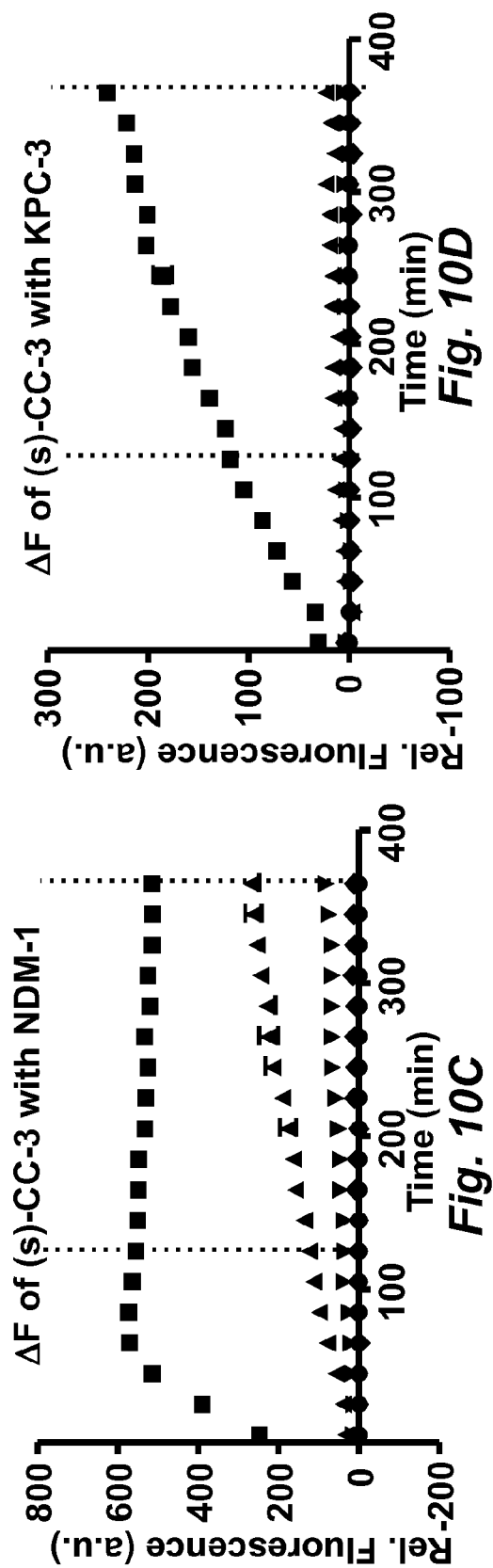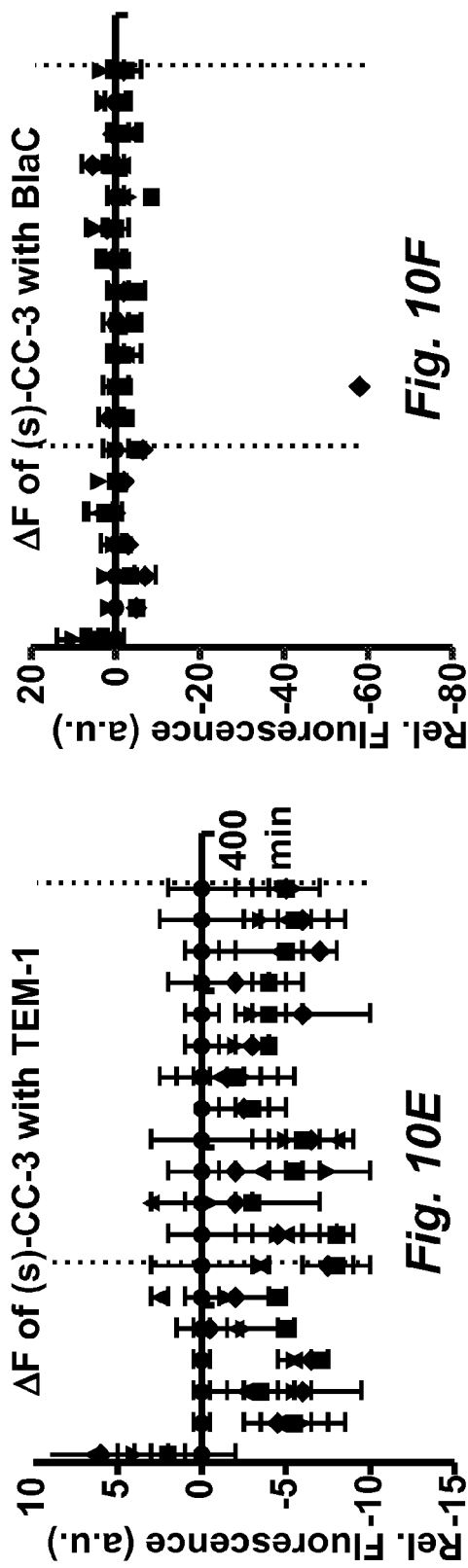

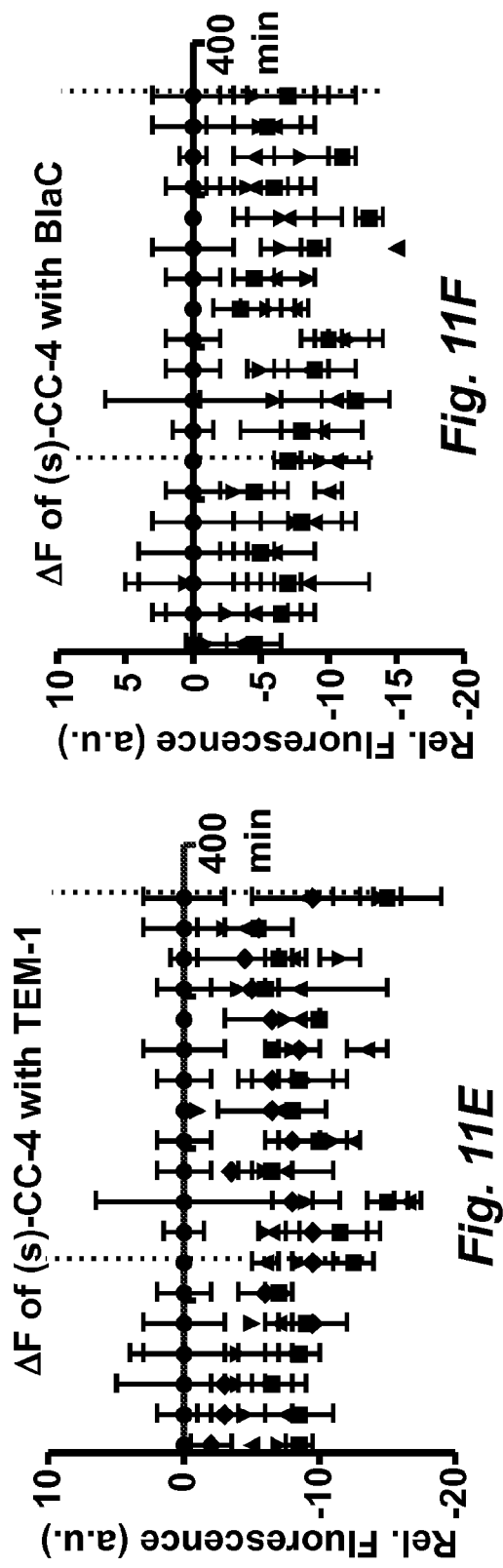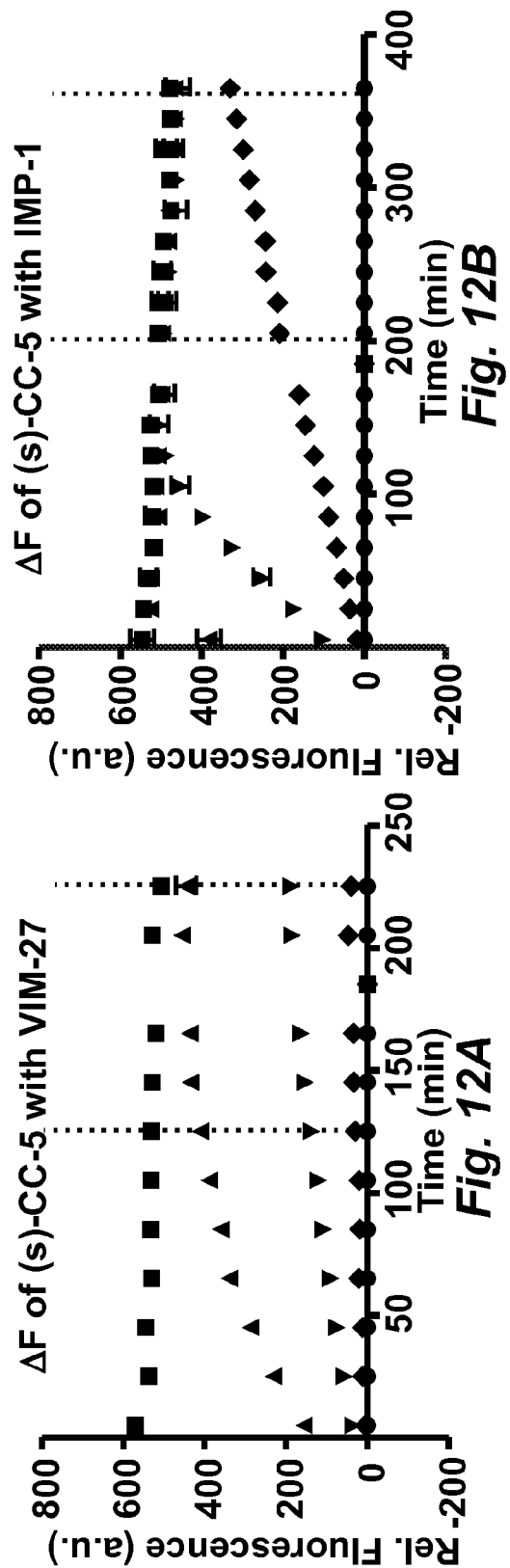

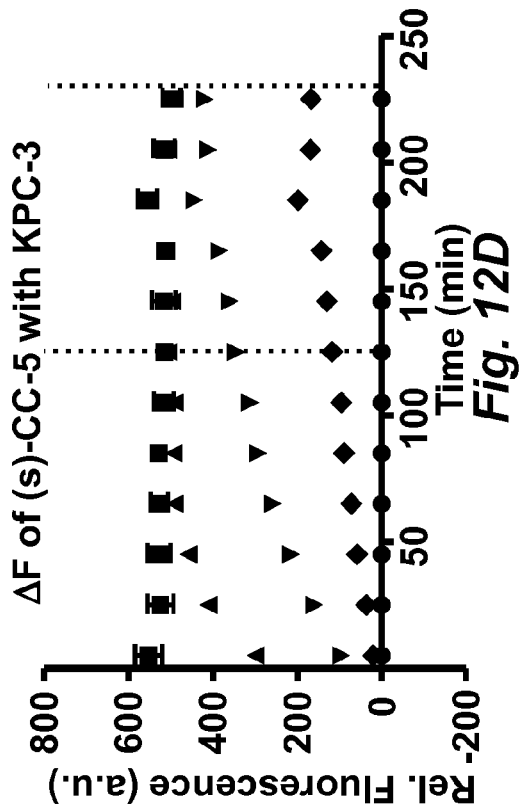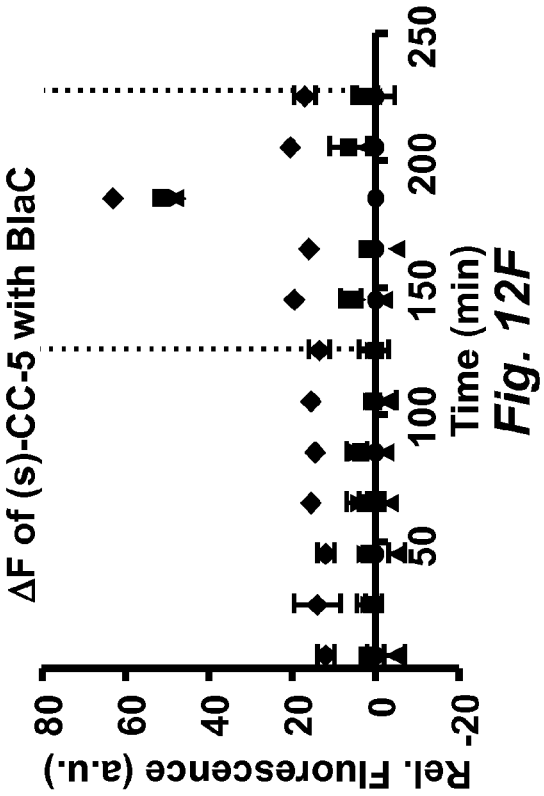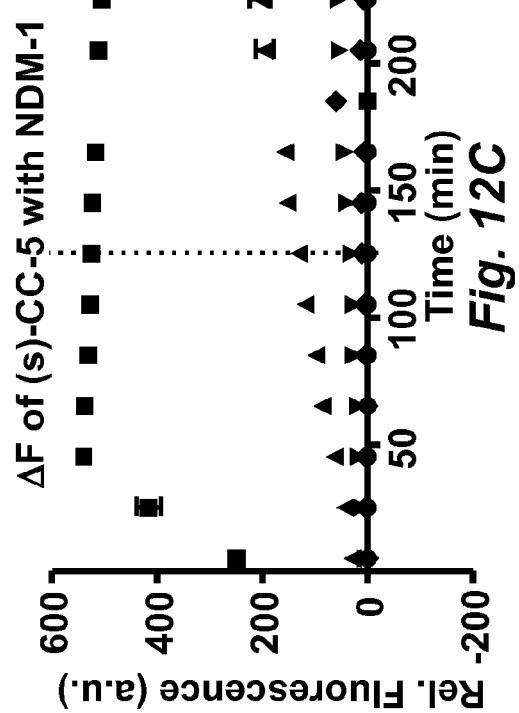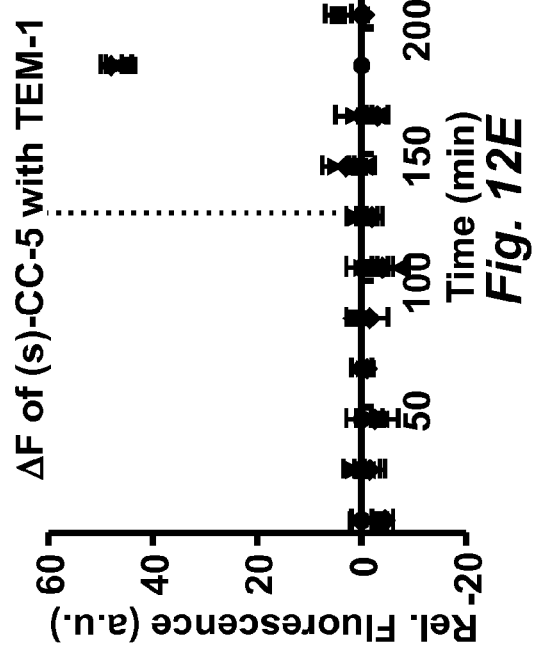

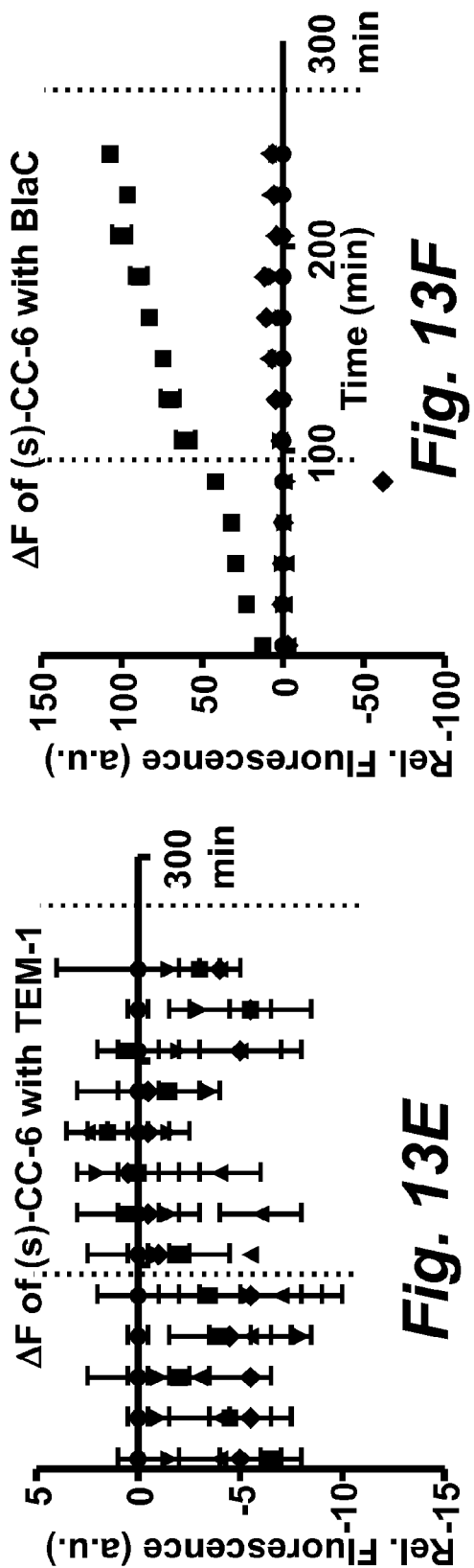

NDM-1 (SEQ ID NO: 3)

gattgggggtgacgtggtcagccatggctcag<u>cgcagcttgtcggccat</u>gcgggccgtatgagtgattgc
<span style="margin-left:15em">NDM-1R</span>
ggcgcggctatcggggcggaatggctcatcacgatcatgctggccttggggaacgccgcaccaaacgcg
cgcgctgacgcggcgtagtgctcagtgtcggcatcaccgagattgccgagcgacttggccttgctgtcct
tgatcaggcagccaccaaaagcgatgtcggtgccgtcgatccaacggtgatattgtcactggtgtggcc
ggggccggggtaaaataccttgagcgggccaaagttgggcgcggttgctggttcgacccagccattggcg
gcgaaagtcaggctgtgttgcgccgcaaccatccctcttgcggggcaagctggttcgacaacgcattgg
cataagtcgcaatcccgcgcatgcagcgcgtccataccgccatcttgtcctgatgcgcgtgagtcac
caccgccagcgcgaccggcaggttgatctcctgcttgatccagttgaggatctgggcggtctggtcatcg
gtccaggcggtatcgaccaccagcacgcggccgcatccctgacgatcaaaccgttggaagcgactgcc
cgaaacccggcatgtcgagataggaagtgtgctgccagacattcggtgcgagctggcggaaaaccagatc
gccaaaccgttggtcgccagttttccatttgctggccaatcgtcgggcggatttcaccgggcatgcaccg
ctcagcatcaatgcagcggctaatgcggtgctcagcttcgcgacc<u>gggtgcataatattgggcaatt</u>cca
<span style="margin-left:30em">NDM-1F</span>
tcaagttttccttttattcagcattaaaaacccgcaaatgcgaggcctagtaaatagat

KPC-1 (SEQ ID NO: 4)

tcaggcgaggtggccgacccatgaacgccgacctgattcgttttttcaagctcggtgataatcccagctgt
agcggcctgattacatccggccgctacacctagctccaccttcaaacaaggaatatcgttgatg<u>tcactg</u>
<u>tatcgccgtctagttc</u>tgctgtcttgtctctcatggccgctggctggcttttctgccaccgcgctgacca
<span style="margin-left:3em">KPC-3F</span>
acctcgtcgcggaaccattcgctaaactcgaacaggactttggcggctccatcggtgtgtacgcgatgga
taccggctcaggcgcaactgtaagttaccgcgctgaggagcgcttccactgtgcagctcattcaagggc
tttcttgctgccgctgtgctggctcgcagccagcagcaggccggcttgctggacacacccatccgttacg
gcaaaaatgcgctggttccgtggtcacccatctcggaaaaatatctgacaacaggcatgacggtggcgga
gctgtccgcggccgcgtgcaatacagtgataacgccgccgccaatttgttgctgaaggagttgggcggc
cggccgggctgacggccttcatgcgctctatcggcgataccacgttccgtctggaccgctgggagctgg
agctgaactccgccatcccaggcgatgcgcgcgatacctcatcgccgcgcgccgtgacggaaagcttaca
aaaactgacactgggctctgcactggctgcgccgcagcggcagcagtttgttgattggctaaagggaaac
acgaccggcaaccacgcatccgcgcggcggtgccggcagactgggcagtcggagacaaaaccggaacct
gcggagtgtatggcacggcaaatgactatgccgtcgtctggcccactgggcgcgcacctattgtgttggc
cgtctacacccgggcgcctaacaaggatgacaagtacagcgaggccgtcatcgccgctgcggctagactc
gcgctcgagg<u>gattgggcgtcaacgggcag</u>taaggctctgaaaatcatctattggcccaccaccgccgcc
<span style="margin-left:10em">KPC-3R</span>
cttgcgggcggcatggattaccaaccactgtcacatttaggctaggagtctgcgcggcagagccgtgtga
ccggttttctgtagagcactgacgat

VIM-27 (SEQ ID NO: 1)

atg<u>ttaaaagttattagtagtttattggtctacatgaccg</u>cgtctgtcatggctgtcgcaagtccgttag
<span style="margin-left:3em">VIM-27F</span>
cccattccggggagccgagtggtgagtatccgacagtcaacgaaattccggtcggagaggtccgacttta
ccagattgccgatggtgtttggtcgcatatctcaacgcagtcgtttgatggcgcggtctacccgtccaat
ggtctcattgtccgtgatggtgatgagttgcttttgattgatacagcgtggggtgcgaaaaacacagcgg
cacttctcgcggagattgaaaagcaaattggacttcccgtaacgcgtgcagtctccacgcactttcatga
cgaccgcgtcggcggcgttgatgtccttcgggcggctggggtggcaacgtacgcatcaccgtcgacacgc
cggctagccgaggcagaggggaacgagattccacgcattctctagaaggactctcatcgagcggggacg
cagtgcgcttcggtccagtagagctcttctatcctggtgctgcgcattcgaccgacaatctggttgtata
cgtcccgtcagcgaacgtgctatacggtggttgtgccgttcatgagttgtcaagcacgtctgcggggaac
gtggccgatgccgatctggctgaatggcccacctccgttgagcggattcaaaaacactacccggaagcag
aggtcgtcattcccgggcacggtctaccgggcggtctagacttgctccagcacacagcgaacgttgtcaa
agca<u>cacaaaaatcgctcagtcgccgagt</u>ag
<span style="margin-left:3em">VIM27R</span>

*Fig. 16*

IMP-1 (SEQ ID NO: 2)
aaaaggaaaagtatg<u>agcaagttatctgtattctttatattttgttttgcagc</u>attgctaccgcagcag
         IMP-1F
agtctttgccagatttaaaaattgaaaagcttgatgaaggcgtttatgttcatacttcgtttgaagaagt
taacgggtggggcgttgttcctaaacatggtttggtggttcttgtaaatgctgaggcttacctaattgac
actccatttacggctaaagatactgaaaagttagtcacttggtttgtggagcgtggctataaaataaaag
gcagcatttcctctcattttcatagcgacagcacgggcggaatagagtggcttaattctcgatctatccc
cacgtatgcatctgaattaacaaatgaactgcttaaaaaagacggtaaggttcaagccacaaattcattt
agcggagttaactattggctagttaaaaataaaattgaagttttttatccaggccgggacacactccag
ataacgtagtggtttggttgcctgaaaggaaaatattattcggtggttgttttattaaaccgtacggttt
aggcaatttgggtgacgcaaatatagaagcttggccaaagtccgccaaattattaaagtccaaatatggt
aaggcaaaactggttgttccaagtcacagtgaagttggagacgcatcactcttgaaacttacattagagc
aggcggttaaagggttaaac<u>gaaagtaaaaaaccatcaaaaccaagcaac</u>taaatttctaacaagtcgtt
             IMP-1R
gcagcacgcc

OXA-48 (SEQ ID NO: 5)
acttcta<u>gggaataattttttcctgtttgagcacttc</u>ttttgtgatggcttggcgcagccctaaaccatc
     OXA-48R
cgatgtgggcatatccatattcatcgcaaaaaaccacacattatcatcaagttcaacccaaccgacccac
cagccaatcttaggttcgattctagtcgagtatccagttttagcccgaataatatagtcaccattggctt
cggtcagcatggcttgtttgacaatacgctggctgcgctccgatacgtgtaacttattgtgatacagctt
tcttaaaaagctgatttgctccgtggccgaaattcgaataccaccgtcgagccagaaactgtctacattg
cccgaaatgtcctcattaccataatcgaaagcatgtagcatcttgctcatacgtgcctcgccaatttggc
gggcaaattcttgataaacaggcacaactgaatatttcatcgcggtgattagattatgatcgcgattcca
agtggcgatatcgcgcgtctgtccatcccacttaaagacttggtgttcatccttaaccacgccaaatcg
agggcgatcaagctattgggaattttaaaggtagatgcgggtaaaaatgcttggttcgccgtttaagat
tattggtaaatccttgctgcttattctcattccagagcacaactacgcctgtgatttatgttcagtaaa
gtgagcattccaacttttgttttcttgccattcctttgctaccgcaggcattccgataatcgatgccacc
aaaaa<u>cacagccgataaggctaatacacg</u>cataacgtcccttgcttaat
  OXA-48F

TEM-1 (SEQ ID NO: 6)
aaggaagagtatg<u>agtattcaacatttccgtgtcgcccttatt</u>cccttttttgcggcattttgccttcct
      TEM-1F
gttttgctcacccagaaacgctggtgaaagtaaaagatgctgaagatcagttgggtgcacgagtgggtt
acatcgaactggatctcaacagcggtaagatccttgagagttttcgccccgaagaacgttttccaatgat
gagcacttttaaagttctgctatgtggtgcggtattatcccgtgttgacgccgggcaagagcaactcggt
cgccgcatacactattctcagaatgacttggttgagtactcaccagtcacagaaaagcatcttacggatg
gcatgacagtaagagaattatgcagtgctgccataaccatgagtgataacactgctgccaacttacttct
gacaacgatcggaggaccgaaggagctaaccgcttttttgcacaacatgggggatcatgtaactcgcctt
gatcgttgggaaccggagctgaatgaagccataccaaacgacgagcgtgacaccacgatgcctgcagcaa
tggcaacaacgttgcgcaaactattaactggcgaactacttactctagcttcccggcaacaattaataga
ctggatggaggcggataaagttgcaggaccacttctgcgctcggcccttccggctggctggtttattgct
gataaatctggagccggtgagcgtgggtctcgcggtatcattgcagcactggggccagatggtaagccct
cccgtatcgtagttatctacacgacggggagtcaggcaactatggatgaacgaaatagacagatcgctga
gataggt<u>gcctcactgattaagcattggtaac</u>tgtcagaccaagtttactcatatactttagattgat
      TEM-1R
ttaaaacttcattttaatttaaaaggatctaggtgaagatcctttttgataatctcatgaccaaaatcc
cttaacgtgagttttcgttccactgagcgtcagaccccgtaggcaaaagaaacgctcgatatcatgcaag
gtctttacgaaactcataagctt

*Fig. 16-Cont'd*

6,7-TRANS CEPHALOSPORIN-BASED PROBES FOR DETECTING BACTERIA EXPRESSING A METALLO-BETA-LACTAMASE

CROSS-REFERENCE TO RELATED APPLICATION

This application is the 35 U.S.C. § 371 national stage application of PCT Application No. PCT/US2015/011533, filed Jan. 15, 2015, where the PCT claims priority to U.S. Provisional Patent Application Ser. No. 61/928,524 entitled "PROBES FOR DETECTION OF CARBAPENEM-RESISTANT BACTERIA" filed Jan. 17, 2014 and to U.S. Provisional Patent Application Ser. No. 61/968,404 entitled "6,7-TRANS CEPHALOSPORIN-BASED FLUOROGENIC PROBES FOR DETECTION OF METALLO-1-LACTAMASE-EXPRESSING BACTERIA" filed Mar. 21, 2014 which are hereby incorporated by reference in their entireties.

STATEMENT OF GOVRENMENT SUPPORT

This invention was made with Government support under contract AI125286 awarded by the National Institutes of Health. The Government has certain rights in the invention.

SEQUENCE LISTING

The present disclosure includes a sequence listing incorporated herein by reference in its entirety.

FIELD OF THE DISCLOSURE

The present disclosure relates to fluorogenic probes specific for carbapenem-resistant enterobacteriaceae (CREs) and based on stereochemically-modified cephalosporins modified to include a 6,7-trans configuration. The disclosure further relates to methods of detecting bacterial strains that are carbapenem-resistant due to metallo-β-lactamase activity.

BACKGROUND

Antibiotic resistance among Gram-negative bacteria such as *Escherichia coli, Klebsiella* species, and other Enterobacteriaceae is emerging worldwide at an alarming rate due to the misuse and overuse of antibiotics (Queenan & Bush (2007) *Clin. Microbiol. Rev.* 20: 440-458; Richard et al., (1994) *J. Infect. Dis.* 170: 377-383; Spellberg et al., (2013) *N. Engl. J. Med.* 368: 299-302). Particularly, the resistance against broad-spectrum β-lactam antibiotics has become a major public health concern. Of many antibiotics, carbapenems have the broadest spectrum of activity and greatest potency against different types of bacteria, and have become the "last resort" in treatment of serious bacterial infections (Bradley et al., (1999) *Int. J. Antimicrob. Agents* 11: 93-100; Papp-Wallace et al., (2011) *Antimicrob. Agents Chemother.* 55: 4943-4960). However, Carbapenem-Resistant Enterobacteriaceaes (CREs) are now frequently observed and the number of cases is steadily growing, mostly due to acquired carbapenemases (Queenan & Bush (2007) *Clin. Microbiol. Rev.* 20: 440-458; Nordmann et al., (2011) *Emerg. Infect. Dis.* 17: 1791-1798).

Carbapenemases are a group of β-lactamases with the ability to hydrolyze almost all β-lactam antibiotics and include Ambler class A β-lactamases of the KPC-type, the metallo-β-lactamases (MBLs) (Ambler class B) of VIM-, IMP-, New Delhi metallo-β-lactamase (NDM), and the relatively rare class D carbapenemase of OXA-48 type (Queenan & Bush (2007) *Clin. Microbiol. Rev.* 20: 440-458; Nordmann et al., (2011) *Emerg. Infect. Dis.* 17: 1791-1798; Miriagou et al., (2010) *Clin. Microbiol. Infect.* 16: 112-122). Carbapenemases are also increasingly reported as the cause of therapeutic failures in hospital- and community-acquired infections, especially for MBLs, because of its transmission between different strains and poor susceptibility to clinically available inhibitors (Queenan & Bush (2007) *Clin. Microbiol. Rev.* 20: 440-458; Walsh et al., (2011) *Clin. Microbiol.* 49: 3222-3227). Therefore, rapid and accurate detection of MBL-producers is critically important for appropriate antibacterial chemotherapies and rigorous infection control.

Currently, the standard diagnostic methods for the detection of β-lactamases, such as the Modified Hodge Test (MHT) (Nordmann et al., (2012) *Clin. Microbiol. Infect.* 18: 432-438; Cohen & Leverstein-van (2010) *Int. J. Antimicrob. Agents* 36: 205-210; Bernabeu et al., (2012) *Diagn. Microbiol. Infect. Dis.* 74: 88-90; Dortet et al., (2012) *Antimicrob. Agents. Chemother.* 56: 6437-6440) and "double-disk synergy test" (DDST) (Arakawa et al., (2000) *J. Clin. Microbiol.* 38: 40-43) lack the necessary specificity and sensitivity, and are time-consuming, typically requiring at least 24-48 hours for accurate detection of most bacteria, but days for those bacteria with a slow growth rate.

PCR-based methods (Poirel et al., (2011) *Diagn. Microbiol. Infect. Dis.* 70: 119-125; Avlami et al., (2010) *J. Microbiol. Methods.* 83: 185-187; Chen et al., (2011) *J. Clin. Microbiol.* 49: 579-585) and mass spectrometry (Burckhardt & Zimmermann (2011) *J. Clin. Microbiol.* 49: 3321-3324; Hrabak et al., (2011) *J. Clin. Microbiol.* 49: 3327-3332) have high accuracy and sensitivity, but are associated with the disadvantages of high cost, heavy instrument requirements, and inability to detect newly-evolved carbapenemase genes. The Carba-NP test (CNP) recently developed by Nordmann (Nordmann et al., (2012) *Emerg. Infect. Dis.* 18: 1503-1507; Dortet et al., (2012) *J. Clin. Microbiol.* 50: 3773-3776; Dortet et al., (2012) *Antimicrob. Agents Chemother.* 56: 6437-6440) has high specificity, but it is only applicable to a bacterial lysate.

In contrast, fluorescence-based bioanalytical assays offer high sensitivity, ease of use, rapid detection, low cost, and little or no need for biological sample processing before analysis. A number of fluorescent probes that enable the detection of the β-lactamase activity with high sensitivity have been developed (Gao et al., (2003) *J. Am. Chem. Soc.* 125: 11146-11147; Zlokarnic et al., (1998) *Science* 279: 86-88; Xing et al., (2005) *J. Am. Chem. Soc.* 127: 4158-4159; Kong et al., (2010) *Proc. Natl. Acad. Sci. USA* 419: 9-16; Xie et al., (2012) *Nat. Chem.* 4: 802-809; Watanabe et al., (2010) *Bioconjugate Chem.* 21: 2320-2326; Zhang et al., (2012) *Angew. Chem. Int. Ed.* 51: 1865-1868; Yang et al., (2007) *J. Am. Chem. Soc.* 129: 266-267). However, most of these probes lack specificity for carbapenemases. Some probes have been used for detecting carbapenemases only when combined with certain inhibitors (Zhang et al., (2012) *Angew. Chem. Int. Ed.* 51: 1865-1868). Thus, few fluorescent probes are available for specifically detecting carbapenemases. The present disclosure provides a series of fluorogenic probes based on cephalosporin with a 6,7-trans configuration suitable for the specific detection of MBLs in bacteria.

SUMMARY

The present disclosure encompasses embodiments of a probe useful for the selective detection of metallo-β-lactamases, in particular carbapenemases, thereby distinguishing those species of bacteria that are carbapenem-resistant from bacterial strains that are sensitive. Cephalosporin-based probes that have the 6,7 R,R configuration are susceptible to cleavage by β-lactamases but cannot distinguish between cleavage by metallo-β-lactamases and other β-lactamases. Modification of the 6,7 position of the β-lactam ring from the R,R configuration to S,R allows a cephalosporin to be cleavable by metallo-β-lactamases, i.e. carbapenemases, but substantially not cleavable by other lactamases. In addition, by modifying a side group of the cephalosporin, selectivity can be introduced allowing the probes to distinguish between various types of metallo-β-lactamases and hence to more narrowly define the strain of bacteria and the type of metallo-β-carbapenemase produced.

One aspect of the disclosure, therefore encompasses embodiments of a composition comprising a probe selectively cleavable by a metallo-β-lactamase, said probe comprising a cephalosporin having a 6,7-trans configuration and a detectable label attached thereto. In some embodiments of this aspect of the disclosure the probe can have the formula I or formula II:

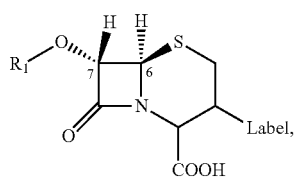

I

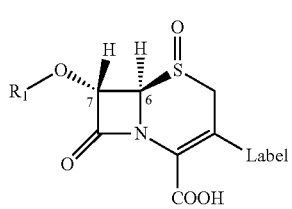

II wherein $R_1$ can be selected from the group consisting of: an alkyl, a substituted alkyl, an aromatic group, a substituted aromatic group, a fluorophore, and a fluorescent quencher.

In some embodiments of this aspect of the disclosure, $R_1$ can be selected from the group consisting of: methyl, ethyl, isopropyl, tert-butyl, benzyl-, and tosyloxy-.

In some embodiments of this aspect of the disclosure the detectable label is (2-oxo-2H-chromen-7-yl) (III) or (4S)-2-(6-oxo-1,3-benzothiazol-2-yl)-4,5-dihydrothiazole-4-carboxylic acid (IV) and can have the structures:

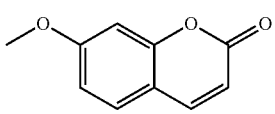

III or

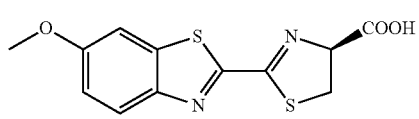

IV

In some embodiments of this aspect of the disclosure the probe can be selected from the group consisting of:

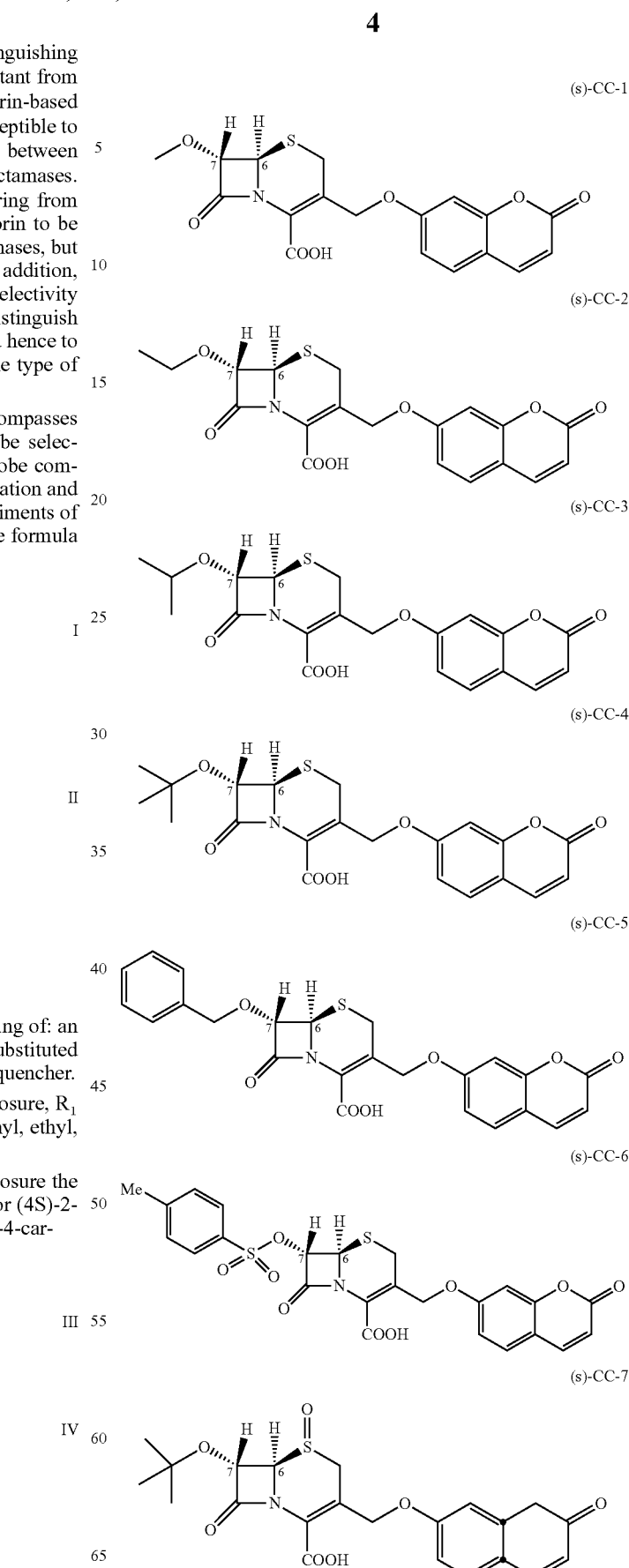

-continued

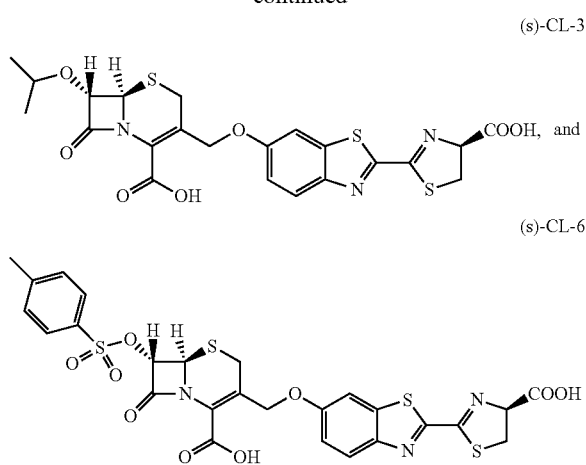

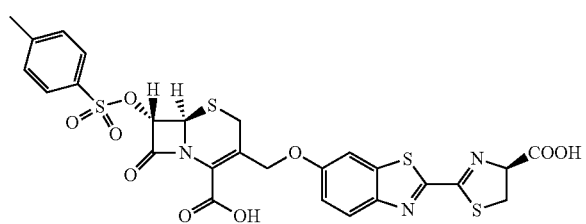

Another aspect of the disclosure encompasses embodiments of a method of selectively detecting a metallo-β-lactamase activity, said method comprising contacting a sample suspected of having a metallo-β-lactamase activity with a composition comprising a probe selectively cleavable by a metallo-β-lactamase, said probe comprising a cephalosporin moiety having a 6,7 trans configuration and a detectable label; allowing an effective period for a metallo-β-lactamase activity to cleave the cephalosporin moiety, thereby releasing the detectable label from the cephalosporin moiety, whereby a detectable signal is generated; and detecting the signal, wherein a detectable signal indicates that the sample contains a metallo-β-lactamase activity or a source of a metallo-β-lactamase activity.

In some embodiments of this aspect of the disclosure the probe has the formula I or formula II:

wherein $R_1$ is selected from the group consisting of: an alkyl, a substituted alkyl, an aromatic group, a substituted aromatic group, a fluorophore, and a fluorescent quencher. In some embodiments of this aspect of the disclosure $R_1$ is selected from the group consisting of: methyl, ethyl, isopropyl, tert-butyl, benzyl-, and tosyloxy-.

In some embodiments of this aspect of the disclosure the detectable label is (2-oxo-2H-chromen-7-yl) (III) or (4S)-2-(6-oxo-1,3-benzothiazol-2-yl)-4,5-dihydrothiazole-4-carboxylic acid (IV) and can have the structures:

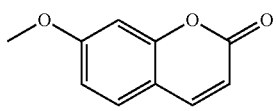

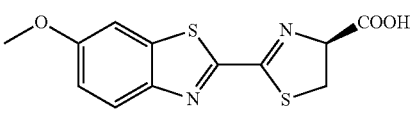

and can be selected from the group consisting of:

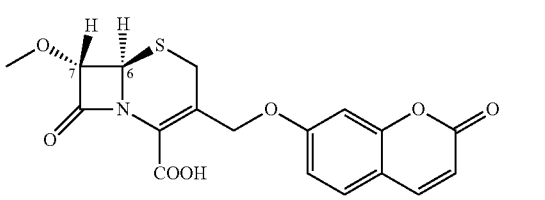

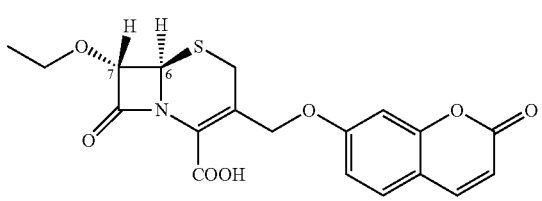

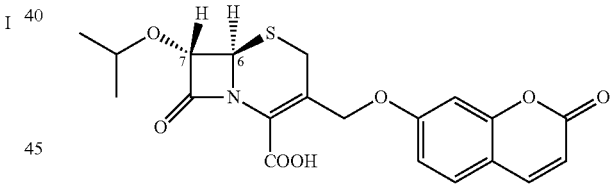

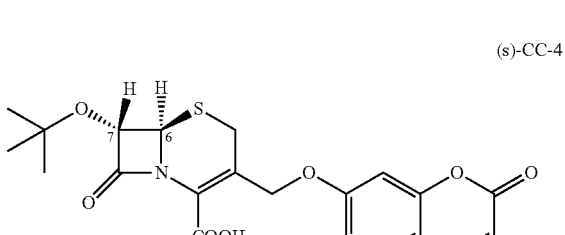

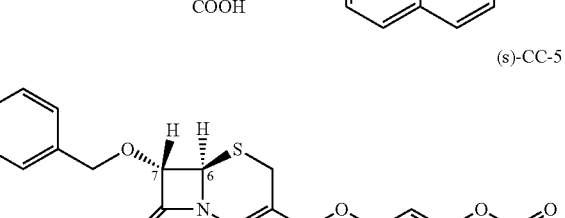

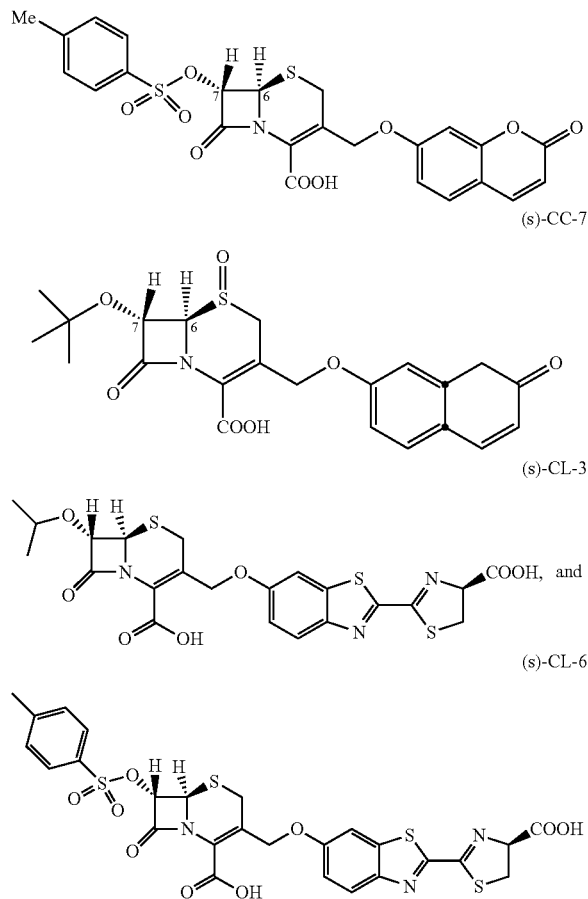

In some embodiments of this aspect of the disclosure the detectable label can be a luciferase substrate and said method can further comprise contacting the reaction mix with a luciferase thereby generating a detectable bioluminescent signal in the presence of released luciferase substrate.

BRIEF DESCRIPTION OF THE DRAWINGS

Aspects of the present disclosure will be more readily appreciated upon review of the accompanying drawings. The drawings are described in greater detail in the description and examples below.

FIG. 2A: probe CDC-1; FIG. 2B: (s)-CC-1; FIG. 2C: (s)-CC-3; FIG. 2D: (s)-CC-4; FIG. 2E: (s)-CC-5, and FIG. 2F: (s)-CC-6. Relative fluorescence represents the difference in the fluorescence intensity with and without β-lactamase incubation. Fluorescence was measured with excitation at 363 nm and emission at 454 nm (band width=5/7.5 nm). Error bars are ±SD.

FIG. 3A: probe CDC-1; FIG. 3B: (s)-CC-1; FIG. 3C: (s)-CC-3; FIG. 3D: (s)-CC-4; FIG. 3E: (s)-CC-5, and FIG. 3F: (s)-CC-6. From left to right in each figure: E. coli with IMP-1 (IMP1-E. coli), K. pneumoniae with VIM-27 (VIM27-Kp), E. coli with NDM-1 (NDM1-E. coli), K. pneumoniae with KPC-3 (KPC3-Kp), K. pneumoniae with CTX-M (CTX-Kp), K. pneumoniae with SHV-18 (SHV18-Kp), E. coli with TEM-1 Bla (TEM1-E. coli), E. coli with AmpC (AmpC-E. coli), E. coli transformed with BlaC (BlaC-E. coli), K. pneumoniae with OXA-48 (OXA48-Kp), E. coli with IMI (IMI-E. coli). All bacteria numbers are as indicated except for E. coli expressing AmpC where $10^7$ c.f.u. were used instead. Relative fluorescence represents the difference in fluorescence intensity with and without β-lactamase incubation. Fluorescence was measured with excitation at 363 nm and emission at 454 nm (band width=5/7.5 nm). Error bars are ±SD.

FIGS. 7A-13F illustrate a series of graphical representations of time-courses of fluorescent activation of probes with the lactamases VIM-27, IMP-1, NDM-1, KPC-3, TEM-1 and BlaC. Error bars are ±SD. Solid circle, Blank; Square, 200 fmoles, 25 μl; Triangle, 20 fmoles, 25 μl; Inverted triangle, 5 fmoles, 25 μl; Diamond, 1 fmole, 25 μl. x-axis, mins.

FIGS. 7A-7F: time-courses of fluorescent activation of CDC-1 with the lactamases VIM-27, IMP-1, NDM-1, KPC-3, TEM-1 and BlaC, respectively.

FIGS. 8A-8F: time-courses of fluorescent activation of (s)-CC-1 with the lactamases VIM-27, IMP-1, NDM-1, KPC-3, TEM-1 and BlaC, respectively.

FIGS. 9A-9F: time-courses of fluorescent activation of (s)-CC-2 with the lactamases VIM-27, IMP-1, NDM-1, KPC-3, TEM-1 and BlaC, respectively.

FIGS. 10A-10F: time-courses of fluorescent activation of (s)-CC-3 with the lactamases VIM-27, IMP-1, NDM-1, KPC-3, TEM-1 and BlaC, respectively.

FIGS. 11A-11F: time-courses of fluorescent activation of (s)-CC-4 with the lactamases VIM-27, IMP-1, NDM-1, KPC-3, TEM-1 and BlaC, respectively.

FIGS. 12A-12F: time-courses of fluorescent activation of (s)-CC-5 with the lactamases VIM-27, IMP-1, NDM-1, KPC-3, TEM-1 and BlaC, respectively.

FIGS. 13A-13F: time-courses of fluorescent activation of (s)-CC-6 with the lactamases VIM-27, IMP-1, NDM-1, KPC-3, TEM-1 and BlaC, respectively.

FIGS. 14A-14G illustrate the spontaneous hydrolysis in buffer of a probe according to the disclosure.

FIG. 14A is a schema illustrating the spontaneous hydrolysis of a probe of the disclosure in PBS buffer to release umbelliferone and thereby generate a fluorescent signal. [S]0=20 μM: Initial concentration of probe, [P]: Concentration of formed umbelliferone (hydrolyzed product).

FIGS. 14B-14G show a series of graphical representations of time-courses of percentage of hydrolyzed product. Error bars indicate the standard deviations of three replicate experiments.

FIG. 16 shows the nucleic acid sequences used as templates for the generation of expression vectors encoding the recombinant β-lactamases VIM-27 (GenBank accession no. HQ858608.1) (SEQ ID NO.: 1), IMP-1 (GenBank accession no. KC200566.1) (SEQ ID NO.: 2), NDM-1 (GenBank accession no. AF059836.1) (SEQ ID NO.: 3), KPC-3 (GenBank accession no. NC_019155.1) (SEQ ID NO.: 4), Oxa-48 (SEQ ID NO.: 5), and TEM-1 (GenBank accession no. KC493654.1) (SEQ ID NO.: 6). GenBank accession numbers for the corresponding amino acid sequences of the enzymes are in parentheses. In the figure, the positions of the primer sequences (as shown in Table 2) used for the PCR amplification step prior to insertion into an expression vector are indicated in bold and underlined.

FIG. 19A, left to right at each concentration: VIM, IMP, NDM, KPC, TEM-1, BlaC. FIG. 19B, left to right: E. coli with IMP-1, K. pneumoniae with VIM-27, E. coli with NDM-1, K. pneumoniae with KPC-3, K. pneumoniae with CTX-M, K. pneumoniae with SHV-18, E. coli with TEM-1 Bla, E. coli with AmpC, E. coli transformed with BlaC, K. pneumoniae with OXA-48, E. coli with IMI. All bacteria numbers are as indicated except that 10$^7$ c.f.u of E. coli expressing AmpC was used. Relative fluorescence represents the difference in the fluorescence intensity with and without β-lactamase/incubation. Fluorescence was measured with excitation at 363 nm and emission at 454 nm (band width=5/7.5 nm). Error bars are ±SD.

Figure 30:
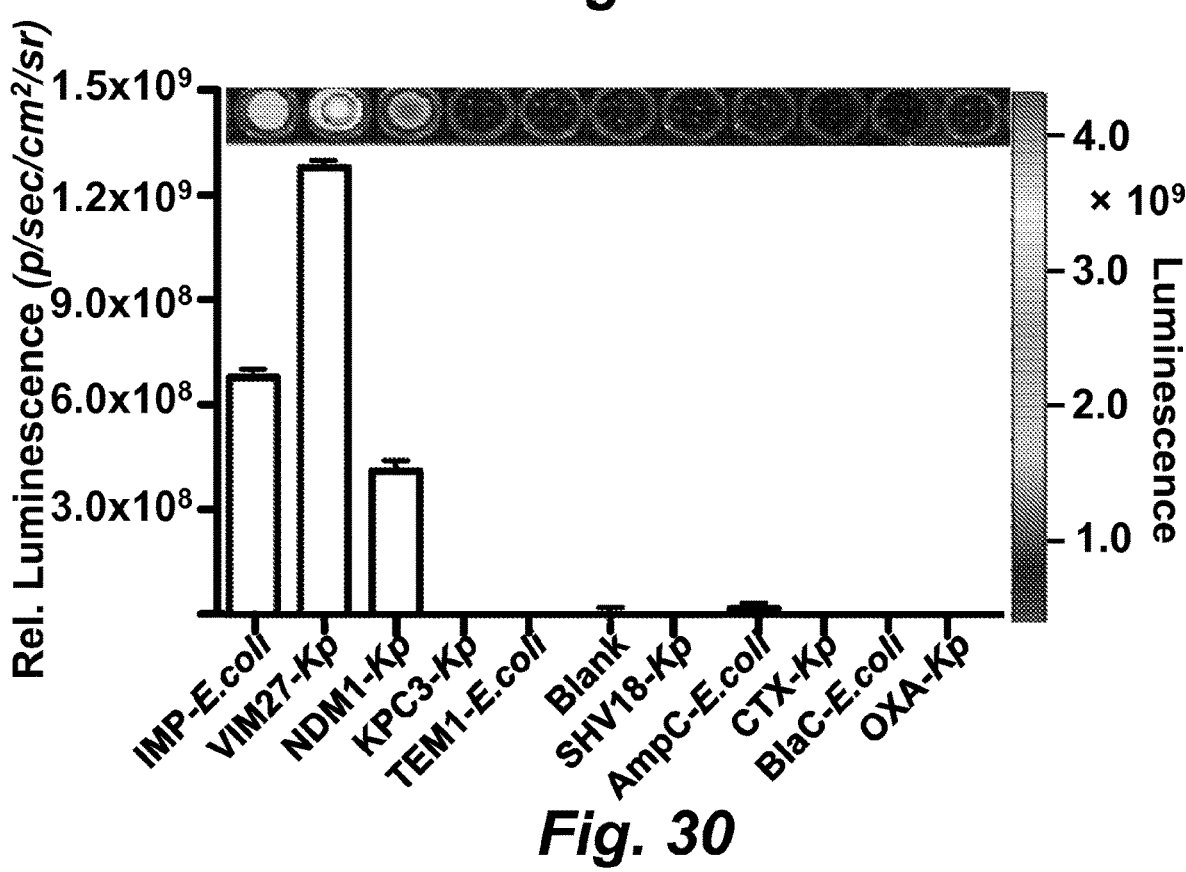

FIG. 30 illustrates β-lactamase selectivity of (s)-CL-6. Relative luminescence of 2×10$^5$ c.f. β-lactamase-expressing bacteria lysates after incubated with probe (1 μM) at room temperature in 100 μL of 1×PBS buffer (pH=7.4) for 2 h followed by addition of 50 ng fLuc. Relative luminescence represents the difference in luminescence intensity with and without β-lactamase-expressing bacteria lysate incubation. The graphs were taken by IVIS. Error bars are ±SD.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated.

Abbreviations

TFAA, Trifluoroacetic anhydride; MLB, metallo-β-lactamase; CRE, carbapenem-resistant enterobacteriaceae; PBS, Phosphate-buffered saline; TsOH, toluenesulfonic acid (PTSA or pTsOH) or tosylic acid; CPBA, chloroperoxybenzoic acid; DCM, dichloromethane; TFA, trifluoroacetic acid; TIPS, SDS, sodium dodecyl sulfate; r.t, room temperature.

Definitions

In describing and claiming the disclosed subject matter, the following terminology will be used in accordance with the definitions set forth below.

The term "acyl" as used herein, alone or in combination, means a carbonyl or thiocarbonyl group bonded to a radical selected from, for example, optionally substituted, hydrido, alkyl (e.g. haloalkyl), alkenyl, alkynyl, alkoxy ("acyloxy" including acetyloxy, butyryloxy, iso-valeryloxy, phenylacetyloxy, berizoyloxy, p-methoxybenzoyloxy, and substituted acyloxy such as alkoxyalkyl and haloalkoxy), aryl, halo, heterocyclyl, heteroaryl, sulfonyl (e.g. allylsulfinylalkyl), sulfonyl (e.g. alkylsulfonylalkyl), cycloalkyl, cycloalkenyl, thioalkyl, thioaryl, amino (e.g alkylamino or dialkylamino), and aralkoxy. Illustrative examples of "acyl" radicals are formyl, acetyl, 2-chloroacetyl, 2-bromacetyl, benzoyl, trifluoroacetyl, phthaloyl, malonyl, nicotinyl, and the like. The term "acyl" as used herein refers to a group —C(O)R$_{26}$, where R$_{26}$ is hydrogen, alkyl, cycloalkyl, cycloheteroalkyl, aryl, arylalkyl, heteroalkyl, heteroaryl, and heteroarylalkyl. Examples include, but are not limited to formyl, acetyl, cyclohexylcarbonyl, cyclohexylmethylcarbonyl, benzoyl, beozylcarbonyl and the like.

The term "acylamino" as used herein refers to an acyl-NH— group wherein acyl is as previously described.

The term "acyloxyl" as used herein refers to an acyl-O— group wherein acyl is as previously described.

The term "alkyl", either alone or within other terms such as "thioalkyl" and "arylalkyl", as used herein, means a monovalent, saturated hydrocarbon radical which may be a straight chain (i.e. linear) or a branched chain. An alkyl radical for use in the present disclosure generally comprises from about 1 to 20 carbon atoms, particularly from about 1 to 10, 1 to 8 or 1 to 7, more particularly about 1 to 6 carbon atoms, or 3 to 6. Illustrative alkyl radicals include methyl, ethyl, n-propyl, n-butyl, n-pentyl, n-hexyl, isopropyl, isobutyl, isopentyl, amyl, sec-butyl, tert-butyl, tert-pentyl, n-heptyl, n-actyl, n-nonyl, n-decyl, undecyl, n-dodecyl, n-tetradecyl, pentadecyl, n-hexadecyl, heptadecyl, n-octadecyl, nonadecyl, eicosyl, dosyl, n-tetracosyl, and the like, along with branched variations thereof. In certain aspects of the disclosure an alkyl radical is a $C_1$-$C_6$ lower alkyl comprising or selected from the group consisting of methyl, ethyl, n-propyl, n-butyl, n-pentyl, n-hexyl, isopropyl, isobutyl, isopentyl, amyl, tributyl, sec-butyl, tert-butyl, tert-pentyl, and n-hexyl. An alkyl radical may be optionally substituted with substituents as defined herein at positions that do not significantly interfere with the preparation of compounds of the disclosure and do not significantly reduce the efficacy of the compounds. In certain aspects of the disclosure, an alkyl radical is substituted with one to five substituents including halo, lower alkoxy, lower aliphatic, a substituted lower aliphatic, hydroxy, cyano, nitro, thio, amino, keto, aldehyde, ester, amide, substituted amino, carboxyl, sulfonyl, sulfuryl, sulfenyl, sulfate, sulfoxide, substituted carboxyl, halogenated lower alkyl (e.g. $CF_3$), halogenated lower alkoxy, hydroxycarbonyl, lower alkoxycarbonyl, lower alkylcarbonyloxy, lower alkylcarbonylamino, cycloaliphatic, substituted cycloaliphatic, or aryl (e.g., phenylmethyl benzyl)), heteroaryl (e.g., pyridyl), and heterocyclic (e.g., piperidinyl, morpholinyl). Substituents on an alkyl group may themselves be substituted.

The term "alkenyl" as used herein refers to an unsaturated, acyclic branched or straight-chain hydrocarbon radical comprising at least one double bond. An alkenyl radical may contain from about 2 to 24 or 2 to 10 carbon atoms, in particular from about 3 to 8 carbon atoms and more particularly about 3 to 6 or 2 to 6 carbon atoms. Suitable alkenyl radicals include without limitation ethenyl, propenyl (e.g., prop-1-en-1-yl, prop-1-en-2-yl, prop-2-en-1-yl (allyl), and prop-2-en-2-yl), buten-1-yl, but-1-en-2-yl, 2-methyl-prop-1-en-1-yl, but-2-en-1-yl, but-2-en-2-yl, buta-1,3-dien-1-yl, beta-1,3-dien-2-3/1, hexen-1-yl, 3-hydroxyhexen-yl, hepten-1-yl, and octen-1-yl, and the like. An alkenyl radical may be optionally substituted similar to alkyl.

The term "alkylcarbamoyl" as used herein refers to a R'RN—CO— group wherein one of R and R is hydrogen and the other of R and R' is alkyl and/or substituted alkyl as previously described.

The term "alkylene" as used herein refers to a linear or branched radical having from about 1 to 10, 1 to 8, 1 to 6, or 2 to 6 carbon atoms and having attachment points for two or more covalent bonds. Examples of such radicals are methylene, ethylene, propylene, butylene, pentylene, hexylene, ethylidene, methylethylene, and isopropylidene. When an alkenylene radical is present as a substituent on another radical it is typically considered to be a single substituent rather than a radical formed by two substituents.

The term "alkenylene" as used herein refers to a linear or branched radical having from about 2 to 10, 2 to 8 or 2 to 6 carbon atoms, at least one double bond, and having attachment points for two or more covalent bonds. Examples of alkenylene radicals include 1,1-vinylidene (—$CH_2$=C—), 1,2-vinylidene (—CH=CH—), and 1,4-butadienyl (—CH=CH—CH=CH—).

The term "aralkoxycarbonyl" as used herein refers to an aralkyl-O—CO— group. An exemplary aralkoxycarbonyl group is benzyloxycarbonyl.

The term "aralkyl" as used herein refers to an aryl or a substituted aryl group bonded directly through an alkyl group, such as benzyl. Other particular examples of substituted aryl radicals include chlorobenzyl, and amino benzyl. Exemplary aralkyl groups include benzyl, phenylethyl, and naphthylmethyl.

The term "aralkyloxyl" as used herein refers to an aralkyl-O— group wherein the aralkyl group is as previously described. An exemplary aralkyloxyl group is benzyloxyl.

The term "aroyl" as used herein refers to aryl radicals, as defined above, attached to a carbonyl radical as defined herein, including without limitation benzoyl and toluoyl. An aroyl radical may be optionally substituted with groups as disclosed herein.

The term "aroylamino" as used herein refers to an aroyl-NH— group wherein aroyl is as previously described.

The term "aryl" as used herein refers to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

An aryl radical may be optionally substituted with one to four substituents such as alkyl, substituted alkyl, alkenyl, substituted alkenyl, alkynyl, substituted alkynyl, aryl, substituted aryl, aralkyl, halo, trifluoromethoxy, trifluoromethyl, hydroxy, alkoxy, alkanoyl, alkanoyloxy, aryloxy, aralkyloxy, amino, alkylamino, acylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfenic acid, alkysulfonyl, sulfonamido, aryloxy and the like. A substituent may be further substituted by hydroxy, halo, alkyl, alkoxy, alkenyl, alkynyl, aryl or aralkyl. In aspects of the disclosure an aryl radical is substituted with hydroxyl, alkyl, carbonyl, carboxyl, thiol, amino, and/or halo.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

The term "aryloxy" as used herein refers to aryl radicals, as defined above, attached to an oxygen atom. Exemplary aryloxy groups include napthyloxy, quinolyloxy, isoquiriolizinyloxy, and the like.

The term "aryloxycarbonyl" as used herein refers to an aryl-O—CO— group. Exemplary aryloxycarbonyl groups include phenoxy- and naphthoxy-carbonyl.

The term "aryloxyl" as used herein refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

The term "arylalkoxy" as used herein refers to an aryl group attached to an alkoxy group. Representative examples of arylalkoxy groups include, but are not limited to, 2-phenylethoxy, 3-naphth-2-ylpropoxy, and 5-phenylpentyloxy.

The term "bioluminescence" as used herein refers to a type of chemiluminescent, emission of light by biological molecules, particularly proteins. The essential condition for bioluminescence is molecular oxygen, either bound or free in the presence of an oxygenase, a luciferase, which acts on a substrate, a luciferin in the presence of molecular oxygen and transforms the substrate to an excited state, which upon return to a lower energy level releases the energy in the form of light.

The term "carbocyclic" as used herein includes radicals derived from a saturated or unsaturated, substituted or unsubstituted 5 to 14 member organic nucleus whose ring forming atoms (other than hydrogen) are solely carbon. Examples of carbocyclic radicals are cycloalkyl, cycloalkenyl, aryl, in particular phenyl, naphthyl, norbornanyl, bicycloheptadienyl, toluoyl, xylenyl, indenyl, stilbenzyl, terphenylyl, diphenylethylenyl, phenylcyclohexyl, acenapththylenyi, anthracenyl, biphenyl, bibenzylyl, and related bibenzylyl homologs, octahydronaphthyl, tetrahydronaphthyl, octahydroquinolinyl, dimethoxytetrahydronaphthyl and the like.

The term "carbamoyl" as used herein, alone or in combination, refers to amino, monoalkylamino, dialkylamino, monocycloalkylamino, alkyleycloalkylamino, and dicycloalkylaxaino radicals, attached to one of two unshared bonds in a carbonyl group.

The term "carbamoyl" as used herein refers to an $H_2N$—CO— group.

The term "carbapenem" as used herein refers to a class of β-lactam antibiotics with a broad spectrum of antibacterial activity. are highly resistant to most β-lactamases. Carbapenem antibiotics were originally developed from the carbapenem thienamycin, a naturally derived product of *Streptomyces cattleya*. Carbapenems are one of the antibiotics of last resort for many bacterial infections, such as *Escherichia coli* (*E. coli*) and *Klebsiella pneumoniae*. The spread of drug resistance to carbapenem antibiotics among these coliforms is often due to production of carbapenemases, including the New Delhi metallo-β-lactamase (NDM-1). There are currently no new antibiotics in development to combat bacteria resistant to carbapenems, and worldwide spread of the resistance gene is considered a major problem. These agents have the broadest antibacterial spectrum compared to other β-lactam classes such as penicillins and cephalosporins. Carbapenems circumvent β-lactamase by binding it with high affinity and acylating the enzyme, rendering it inactive. Carbapenems are active against both Gram-positive and Gram-negative bacteria, and anaerobes, with the exception of intracellular bacteria (atypicals), such as the Chlamydiae. Carbapenems also are thus far the only β-lactams capable of inhibiting L,D-transpeptidases. Carbapenems are very similar to the penicillins (penams), but the sulfur atom in position 1 of the structure has been replaced with a carbon atom, and an unsaturation has been introduced.

The term "carbapenemase" as used herein refers to a group of 3-lactamases that are active against the oxyimino-cephalosporins, cephamycins, and but also against the carbapenems. Carbapenemases include such as IMP-type carbapenemases (metallo-6-lactamases), which are plasmid-mediated carbapenemases, and can be found in bacterial species such as enteric Gram-negative organisms, *Pseudomonas* spp. and *Acinetobacter* spp. VIM (Verona integron-encoded metallo-β-lactamase) includes 10 members, which occur mostly in *P. aeruginosa*, also *P. putida* and, very rarely, Enterobacteriaceae. Both IMP and VIM are integron-associated, sometimes within plasmids. Both hydrolyze all β-lactams except monobactams, and evade all β-lactam inhibitors.

The OXA group of β-lactamases occur mainly in *Acinetobacter* species. OXA carbapenemases hydrolyze carbapenems very slowly in vitro, and the high MICs seen for some *Acinetobacter* hosts (greater than 64 mg/L) may reflect secondary mechanisms. OXA carbapenemases also tend to have a reduced hydrolytic efficiency towards penicillins and cephalosporins. KPC (*K. pneumoniae* carbapenemase) is currently the most common carbapenemase of Enterobacteriaceae that produce KPC were becoming common in the United States. CMY was isolated from a virulent strain of *Enterobacter aerogenes*. It is carried on a plasmid, pYMG-1, and is therefore transmissible to other bacterial strains. NDM-1 (New Delhi metallo-β-lactamase) is widespread in *Escherichia coli* and *Klebsiella pneumoniae*.

Bacteria that can be susceptible to the lactamases of the disclosure include Gram-negative bacteria such as, but are not limited to, *E. cloacae, C. freundii, S. marcescens, P. aeruginosa, K. pneumoniae, Proteus mirabilis*, Enterobacteriaceae including *Escherichia* spp., *Salmonella* spp. *H. influenzae, N. gonorrhoeae, Kluyvera* spp., *Salmonella enterica* serovar *Typhimurium* and the like, and Gram-positive bacteria such a *Staphylococci* spp., *Streptococci* spp., *Streptobacilli* spp., *Bacilli* spp., and the like.

The term "carbonyl" as used herein refers to a carbon radical having two of the four covalent bonds shared with an oxygen atom. Carbonyl—The term "carbonyl" as used herein refers to the —(C=O)— group.

The term "carboxamide" as used herein refers to the group —CONH—. Carboxyl—The term "carboxyl" as used herein refers to the —COOH group.

The term "carboxyl" as used herein, alone or in combination, refers to —C(O)OR$_{25}$— or —C(—O)OR$_{25}$ wherein R$_{25}$ is hydrogen, alkyl, alkenyl, alkynyl, cycloalkyl, cycloalkenyl, amino, thiol, aryl, heteroaryl, thioalkyl, thioaryl, thioalkoxy, a heteroaryl, or a heterocyclic, which may optionally be substituted. In aspects of the disclosure, the carboxyl groups are in an esterified form and may contain as an esterifying group lower alkyl groups. In particular aspects of the disclosure, —C(O)OR$_{25}$ provides an ester or an amino acid derivative. An esterified form is also particularly referred to herein as a "carboxylic ester". In aspects of the disclosure a "carboxyl" may be substituted, in particular substituted with allyl which is optionally substituted with one or more of amino, amine, halo, alkylamino, aryl, carboxyl, or a heterocyclic. Examples of carboxyl groups are methoxycarbonyl, butoxycarbonyl, tert.alkoxycarbonyl such as tert.butoxycarbonyl, arylmethyoxycarbonyl having one or two aryl radicals including without limitation phenyl optionally substituted by for example lower alkyl, lower alkoxy, hydroxyl, halo, and/or nitro, such as benzyloxycarbonyl, methoxybenzyloxycarbonyl, diphenylmethoxycarbonyl, 2-bromoethoxycarbonyl, 2-iodoethoxycarbonyltert.butylcarborlyl, 4-nitrobenzyloxycarbonyl, di phenylmethoxycarbonyl, benzhydroxycarbonyl, di-(4-methoxyphenyl-methoxycarbonyl, 2-bromoethoxycarbonyl, 2-iodoethoxycarbonyl, 2-trimethylsilylethoxycarbonyl, or 2-triphenylsilylethoxycarbonyl. Additional carboxyl groups in esterified form are silyloxycarbonyl groups including organic silyloxycarbonyl. The silicon substituent in such compounds may be substituted with lower alkyl (e.g. methyl), alkoxy (e.g. methoxy), and/or halo (e.g. chlorine). Examples of silicon substituents include trimethylsilyi and dimethyltert.butylsilyl. In aspects of the disclosure, the carboxyl group may be an alkoxy carbonyl, in particular methoxy carbonyl, ethoxy carbonyl, isopropoxy carbonyl, t-butoxycarbonyl, t-pentyloxycarbonyl, sir heptyloxy carbonyl, especially methoxy carbonyl or ethoxy carbonyl.

The term "cephalosporin" as used herein refers to beta-lactam compounds in which the beta-lactam ring is fused to a 6-membered dihydrothiazine ring, thus forming the cephem nucleus. Side chain modifications to the cephem nucleus can confer an improved spectrum of antibacterial activity, pharmacokinetic advantages, and additional side effects. Based on their spectrum of activity, cephalosporins can be broadly categorized into four generations.

The terms "cyclic" and "cycloalkyl" as used herein refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur, or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

The term "cycloaliphatic" as used herein refers to a cycloalkane possessing less than 8 carbons or a fused ring system consisting of no more than three fused cycloaliphatic rings. Examples of such groups include, but are not limited to, decalin and the like.

The term "cycloalkenyl" as used herein refers to radicals comprising about 4 to 16, 2 to 15, 2 to 10, 2 to 8, 4 to 10, 3 to 8, 3 to 7, 3 to 6, or 4 to 6 carbon atoms, one or more carbon-carbon double bonds, and one, two, three, or four rings wherein such rings may be attached in a pendant manner or may be fused. In certain aspects of the disclosure the cycloalkenyl radicals are "lower cycloalkenyl" radicals having three to seven carbon atoms. Examples of cycloalkenyl radicals include without limitation cyclobutenyl, cyclopentenyl, cyclohexenyl and cycloheptenyl. A cycloalkenyl radical may be optionally substituted with groups as disclosed herein, in particular 1, 2, or 3 substituents which may be the same or different.

The term "cycloalkoxy" as used herein refers to cycloalkyl radicals (in particular, cycloalkyl radicals having 3 to 15, 3 to 8 or 3 to 6 carbon atoms) attached to an oxy radical. Examples of cycloalkoxy radicals include cyclohexoxy and cyclopentoxy. A cycloalkoxy radical may be optionally substituted with groups as disclosed herein.

The term "cycloalkyl" as used herein refers to radicals having from about 3 to 15, 3 to 10, 3 to 8, or 3 to 6 carbon atoms and containing one, two, three, or four rings wherein such rings may be attached in a pendant manner or may be fused. In aspects of the disclosure, "cycloalkyl" refers to an optionally substituted, saturated hydrocarbon ring system containing 1 to 2 rings and 3 to 7 carbons per ring which may be further fused with an unsaturated C3-C7 carbocylic ring. Examples of cycloalkyl groups include single ring structures such as cyclopropyl, cyclobutyl, cyclopentyl, cyclohexyl, cycloheptyl, cyclooctyl, cyclononyl, cyclodecyl, cyclododecyl, and the like, or multiple ring structures such as adamantanyl, and the like. Tin certain aspects of the disclosure the cycloalkyl radicals are "lower cycloalkyl" radicals having from about 3 to 10, 3 to 8, 3 to 6, or 3 to 4 carbon atoms, in particular cyclopropyl, cyclobutyl, cyclopentyl, cyclohexyl and cycloheptyl. The term "cycloalkyl" also embraces radicals where cycloalkyl radicals are fused with aryl radicals or heterocyclyl radicals. A cycloalkyl radical may be optionally substituted with groups as disclosed herein.

The term "detectable moiety" as used herein refers to various labeling moieties known in the art. Said moiety may be, for example, a radiolabel (e.g., $^3H$, $^{125}I$, $^{35}S$, $^{14}C$, $^{32}P$, etc.), detectable enzyme (e.g., horse radish peroxidase (HRP), alkaline phosphatase etc.), a dye, a colorimetric label such as colloidal gold or colored glass or plastic (e.g., polystyrene, polypropylene, latex, etc.), beads, or any other moiety capable of generating a detectable signal such as a colorimetric, fluorescent, chemiluminescent or electro-chemiluminescent (ECL) signal. Thus, "detectable moiety" is used synonymously with "label molecule". Label molecules, known to those skilled in the art as being useful for detection, include chemiluminescent or fluorescent molecules. Various fluorescent molecules are known in the art which are suitable for use to label a nucleic acid for the method of the present invention. The protocol for such incorporation may vary depending upon the fluorescent molecule used. Such protocols are known in the art for the respective fluorescent molecule.

In the embodiments of the probes of the disclosure, it is contemplated that the detectable moiety may be released from the probe upon hydrolytic cleavage of the cephalosporin by a carbapenemase so that a fluorescent dye, for example, is no longer quenched and, therefore, is detectable. It is further contemplated that a detectable moiety such as a light-absorbing dye or a radioactive label may be released and separated from uncleaved probes for quantitative or qualitative detection indicating the presence of a carbapenemase activity.

The term "detectably labeled" as used herein means that a compound such as a cephalosporin-based probe of the disclosure may contain a moiety that is radioactive, or that is substituted with a fluorophore, or that is substituted with some other molecular species that elicits a physical or chemical response that can be observed or detected by the naked eye or by means of instrumentation such as, without limitation, scintillation counters, colorimeters, UV spectrophotometers and the like.

Spectroscopic, photochemical, biochemical, immunochemical, electrical, optical or chemical means can be used to detect such labels. The detection device and method may include, but is not limited to, optical imaging, electronic imaging, imaging with a CCD camera, integrated optical imaging, and mass spectrometry. Further, the amount of labeled or unlabeled probe bound to the target may be quantified. Such quantification may include statistical analysis.

The term "dialkylamino" as used herein refers to an —NRR' group wherein each of R and R' is independently an alkyl group and/or a substituted alkyl group as previously described. Exemplary alkylamino groups include ethylmethylamino, dimethylamino, and diethylamino.

The term "dialkylcarbamoyl" as used herein refers to a R'RN—CO— group wherein each of R and R' is independently alkyl and/or substituted alkyl as previously described.

The term "diasteriomer" as used herein refers to a compound of the disclosure that can contain one or more asymmetric centers and may give rise to enantiomers, diasteriomers, and other stereoisomeric forms which may be defined in terms of absolute stereochemistry as (R)- or (S)-. Thus, compounds of the disclosure include all possible diasteriomers and enantiomers as well as their racemic and optically pure forms. Optically active (R)- and (S)-isomers may be prepared using chiral synthons or chiral reagents, or resolved using conventional techniques. When a compound of the disclosure contains centers of geometric asymmetry, and unless specified otherwise, it is intended that the compounds include both E and A geometric isomers. All tautomeric forms are also included within the scope of a compound of the disclosure.

The term "dye" as used herein refers to any reporter group whose presence can be detected by its light absorbing or light emitting properties. For example, Cy5 is a reactive water-soluble fluorescent dye of the cyanine dye family. Cy5 is fluorescent in the red region (about 650 to about 670 nm). It may be synthesized with reactive groups on either one or both of the nitrogen side chains so that they can be chemically linked to either nucleic acids or protein molecules. Labeling is done for visualization and quantification purposes. Cy5 is excited maximally at about 649 nm and emits maximally at about 670 nm, in the far red part of the spectrum; quantum yield is 0.28. FW=792. Suitable fluorophores(chromes) for the probes of the disclosure may be selected from, but not intended to be limited to, fluorescein isothiocyanate (FITC, green), cyanine dyes Cy2, Cy3, Cy3.5, Cy5, Cy5.5 Cy7, Cy7.5 (ranging from green to near-infrared), Texas Red, and the like. Derivatives of these dyes for use in the embodiments of the disclosure may be, but are not limited to, Cy dyes (Amersham Bioscience), Alexa Fluors (Molecular Probes Inc.), HILYTE® Fluors (AnaSpec), and DYLITE® Fluors (Pierce, Inc.).

The term "fluorescence" as used herein refers to a luminescence that is mostly found as an optical phenomenon in cold bodies, in which the molecular absorption of a photon triggers the emission of a photon with a longer (less energetic) wavelength. The energy difference between the absorbed and emitted photons ends up as molecular rotations, vibrations or heat. Sometimes the absorbed photon is in the ultraviolet range, and the emitted light is in the visible range, but this depends on the absorbance curve and Stokes shift of the particular fluorophore.

The term "fluorophore" as used herein refers to a component of a molecule that causes a molecule to be fluorescent. The term "fluorophore" as used herein refers to any reporter group whose presence can be detected by its light emitting properties. It is a functional group in a molecule which will absorb energy of a specific wavelength and re-emit energy at a different (but equally specific) wavelength. The amount and wavelength of the emitted energy depend on both the fluorophore and the chemical environment of the fluorophore. Fluorophores for use in the compositions of the disclosure include, but are not limited to, fluorescein isothiocyanate (FITC), a reactive derivative of fluorescein, which has been one of the most common fluorophores chemically attached to other, non-fluorescent, molecules to create new fluorescent molecules for a variety of applications. Other historically common fluorophores are derivatives of rhodamine (TRITC), coumarin, and cyanine. Newer generations of fluorophores such as the ALEXA FLUORS®, DYLIGHT FLUORS® and the green fluorescent fluorophore Tokyo Green are generally more photostable, brighter, and less pH-sensitive than other standard dyes of comparable excitation and emission.

The term "FRET" as used herein refers to fluorescence resonance energy transfer between molecules. In FRET methods, one fluorophore is able to act as an energy donor and the other of which is an energy acceptor molecule. These are sometimes known as a reporter molecule and a quencher molecule respectively. The donor molecule is excited with a specific wavelength of light for which it will normally exhibit a fluorescence emission wavelength. The acceptor molecule is also excited at this wavelength such that it can accept the emission energy of the donor molecule by a variety of distance-dependent energy transfer mechanisms. Generally the acceptor molecule accepts the emission energy of the donor molecule when they are in close proximity (e.g., on the same, or a neighboring molecule). FRET techniques are well known in the art, and can be readily used to detect the titanium oxide-bound peptides of the present disclosure. See for example U.S. Pat. Nos. 5,668,648, 5,707,804, 5,728,528, 5,853,992, and 5,869,255 (for a description of FRET dyes), T Mergny et al., (1994) Nucleic Acid Res. 22:920-928, and Wolf et al., (1988) Proc. Natl. Acad. Sci. USA 85:8790-8794 (for general descriptions and methods for FRET), each of which is hereby incorporated by reference in its entirety.

The term "heteroaryl" as used herein refers to fully unsaturated heteroatom-containing ring-shaped aromatic radicals having at least one heteroatom selected from carbon, nitrogen, sulfur and oxygen. A heteroaryl radical may contain one, two or three rings and the rings may be attached in a pendant manner or may be fused. In aspects of the disclosure the term refers to fully unsaturated heteroatom-containing ring-shaped aromatic radicals having from 3 to 15, 3 to 10, 3 to 8, 5 to 15, 5 to 10, or 5 to 8 ring members selected from carbon, nitrogen, sulfur and oxygen, wherein at least one ring atom is a heteroatom. Examples of "heteroaryl" radicals, include without limitation, an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, tetrazolyl and the like; an unsaturated condensed heterocyclic group containing 1 to 5 nitrogen atoms, in particular, indolyl, isoindolyl, indolizinyl, benzimidazolyl, quinolyl, isoquinolyl, indazolyl, quinazolinyl, pteridinyl, quinolizidinyl, phthalazinyl, naphthyridinyl, quinoxalinyl, cinnolinyl, phenanthridinyl, acridinyl, phenanthrolinyl, phenazinyl, carbazolyl; purinyl, benzimidazolyl, quinolinyl, isoquinolinyl, beazotriazolyl, tetrazolopyridazinyl and the like; an unsaturated 3 to 6-membered heteromonocyclic group containing an oxygen atom, in particular, 2-furyl, pyranyl, and the like; an unsaturated 5 to 6-membered heteromonocyclic group containing a sulfur atom, in particular, thienyl, 2-thienyl, 3-thienyl, and the like; unsaturated 5 to 6-membered heteromonocyclic group containing 1 to 2 oxygen atoms and 1 to 3 nitrogen atoms, in particular, furazanyl, benzofurazanyl, oxazolyl, isoxazolyl, and oxadiazolyl; an unsaturated condensed heterocyclic group containing 1 to 2 oxygen atoms and 1 to 3 nitrogen atoms, in particular benzoxazolyl, benzoxadiazolyl and the like; an unsaturated 5 to 6-membered heteromonocyclic group containing 1 to 2 sulfur atoms and 1 to 3 nitrogen atoms, for example, thiazolyl, isothiazolyl, thiadiazolyl and the like; an unsaturated condensed heterocyclic group containing 1 to 2 sulfur atoms and 1 to 3 nitrogen atoms such as benzothiazolyl, benzothiadiazolyl and the like. The term also includes radicals where heterocyclic radicals are fused with aryl radicals, in particular bicyclic radicals such as benzofuranyl, benzothiophenyl, phthalazinyl, chromenyl, xanthenyl, and the like. A heteroaryl radical may be optionally substituted with groups as disclosed herein, for example with an alkyl, amino, halogen, etc., in particular a heteroarylamine. The term may refer to an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, pyridinyl, pyrimidinyl, pyrazinyl, pyridazinyl, triazolyl, tetrazolyl and the like. A heteroaryl radical may be optionally substituted with groups disclosed herein, for example with an alkyl, amino, halogen, etc., in particular a substituted heteroaryl radical is a heteroarylamine.

The term "heterocyclic" as used herein refers to a cycloalkane and/or an aryl ring system, possessing less than 8 carbons, or a fused ring system consisting of no more than three fused rings, where at least one of the ring carbon atoms is replaced by oxygen, nitrogen or sulfur. Examples of such groups include, but are not limited to, morpholino and the like.

The term "heterocyclic" as used herein refers to saturated and partially saturated heteroatom containing ring-shaped radicals having at least one heteroatom selected from carbon, nitrogen, sulfur and oxygen. A heterocyclic radical may contain one, two or three rings wherein such rings may be attached in a pendant manner or may be fused. In an aspect, the term refers to a saturated and partially saturated heteroatom-containing ring-shaped radicals having from about 3 to 15, 3 to 10, 5 to 15, 5 to 10, or 3 to 8 ring members selected from carbon, nitrogen, sulfur and oxygen, wherein at least one ring atom is a heteroatom. Exemplary saturated heterocyclic radicals include without limitation a saturated 3 to 6-membered heteromonocyclic group containing 1 to 4 nitrogen atoms (e.g. pyrrolidinyl, imidazolidinyl, and piperazinyl); a saturated 3 to 6-membered heteromonocyclic group containing 1 to 2 oxygen atoms and 1 to 3 nitrogen atoms (e.g. morpholinyl; sydnonyl]; and, a saturated 3 to 6-membered heteromonocyclic group containing 1 to 2 sulfur atoms and 1 to 3 nitrogen atoms [e.g., thiazolidinyl) and the like. Examples of partially saturated heterocyclyl radicals include without limitation dihydrothiophene, dihydropyranyl, dihydrofuranyl and dihydrothiazolyl. Illustrative heterocyclic radicals include without limitation aziridinyl, azetidinyl, 2-pyrrolinyl, 3-pyrrolinyl, pyrrolidinyl, azepinyl, 1,3-dioxolanyl, 211-pyranyl, 4H-pyranyl, piperidinyl, 1,4-dioxanyl, morpholinyl, pyrazolinyl, thiomorpholinyl, 1,2,3,6-tetrahydropyridinyl, oxiranyl, oxetanyl, tetrahydrofuranyl, tetrahydropyranyl, tetrahydropyridinyl, tetrahydrothiopyranyl, thioxanyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, quinuelidinyl, quinolizinyl, and the like.

The term "hydroxyalkyl" as used herein refers to an alkyl group substituted with an —OH group.

The term "hydroxyl" or "hydroxy" as used herein refers to the —OH group.

The term "linker" as used herein refers to a functional group (e.g., an amine group) on the cephalosporin backbone of the compounds of the disclosure, or the linker can include a separate moiety attached to the cephalosporin to which a molecule such as a fluorophore or quencher may then be attached. The linker can include functional groups such as, but not limited to, amines, carboxylic acids, hydroxyls, thios, and combinations thereof. The linker can include compounds such as, but not limited to, DTPA, EDTA, DOPA, EGTA, NTA, and combinations thereof. In an embodiment, the linker and the chelator compound are the same, but in other embodiments they can be different.

In advantageous embodiments of the probes of the disclosure, it is contemplated that a label such as, but not limited to, a fluorophore may be attached to the cephalosporin moiety by an —O—, a —N—, or an —S— link.

The term "lower-alkyl-substituted-halogen" as used herein refers to any alkyl chain containing up to and including eight carbon atoms where one of the aliphatic hydrogen atoms is replaced by a halogen. Examples of such include, but are not limited to, chlorethyl and the like.

The term "luciferase" as used herein refers to oxygenases that catalyze a light emitting reaction. For instance, bacterial luciferases catalyze the oxidation of flavin mononucleotide and aliphatic aldehydes, which reaction produces light. Another class of luciferases, found among marine arthropods, catalyzes the oxidation of cypridina luciferin, and another class of luciferases catalyzes the oxidation of coleoptera luciferin. Thus, "luciferase" refers to an enzyme or photoprotein that catalyzes a bioluminescent reaction. The luciferases such as firefly and *Renilla* luciferases are enzymes that act catalytically and are unchanged during the bioluminescence generating reaction. The luciferase photoproteins, such as the aequorin and obelin photoproteins to which luciferin is non-covalently bound, are changed by release of the luciferin, during bioluminescence generating reaction. The luciferase is a protein that occurs naturally in an organism or a variant or mutant thereof, such as a variant produced by mutagenesis that has one or more properties, such as thermal or pH stability, that differ from the naturally-occurring protein. Luciferases and modified mutant or variant forms thereof are well known. Reference, for example, to "*Renilla* luciferase" means an enzyme isolated from member of the genus *Renilla* or an equivalent molecule obtained from any other source, such as from another Anthozoa, or that has been prepared synthetically.

The term "operably linked" as used herein refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

The term "primer" as used herein refers to an oligonucleotide complementary to a DNA segment to be amplified or replicated. Typically primers are used in PCR. A primer hybridizes with (or "anneals" to) the template DNA and is used by the polymerase enzyme as the starting point for the replication/amplification process. By "complementary" it is meant that the primer sequence can form a stable hydrogen bond complex with the template.

The term "probe" as used herein refers to a modified cephalosporin having a 6,7 trans configuration and which is selectively cleaved by a metallo-β-lactamase and may have a side group derived from an alcohol that allows the probe to selectively distinguish between metallo-β-lactamase species.

The term "substituted alkenyl" as used herein includes an alkenyl group substituted by, for example, one to three substituents, preferably one to two substituents, such as alkyl, alkoxy, haloalkoxy, alkylalkoxy, haloalkoxyalkyl, alkanoyl, alkanoyloxy, cycloalkyl, cycloalkoxy, acyl, acylamino, acyloxy, amino, alkylamino, alkanoylamino, aminoacyl, aminoacyloxy, cyano, halogen, hydroxyl, carboxyl, carboxylalkyl, carbamyl, keto, thioketo, thiol, alkylthio, sulfonyl, sulfonamido, thioalkoxy, aryl, nitro, and the like.

The term "substituted alkyl" as used herein can include an alkyl group substituted by, for example, one to five substituents, and preferably 1 to 3 substituents, such as alkyl, alkoxy, oxo, alkanoyl, aryl, aralkyl, aryloxy, alkanoyloxy, cycloalkyl, acyl, amino, hydroxyamino, alkylamino, arylamino, alkoxyamino, aralkylamino, cyano, halogen, hydroxyl, carboxyl, carbamyl, carboxylalkyl, keto, thioketo, thiol, alkylthiol, arylthio, aralkylthio, sulfonamide, thioalkoxy; and nitro.

The term "substituted aryl" as used herein includes an aromatic ring, or fused aromatic ring system consisting of no more than three fused rings at least one of which is aromatic, and where at least one of the hydrogen atoms on a ring carbon has been replaced by a halogen, an amino, a hydroxy, a nitro, a thio, an alkyl, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, hydroxyphenyl, chlorphenyl alkylamino, dialkylamino, sulfate, mercapto, and the like.

The term "substituted cycloaliphatic" as used herein refers to a cycloalkane possessing less than 8 carbons or a fused ring system consisting of no more than three fused rings, and where at least one of the aliphatic hydrogen atoms has been replaced by a halogen, a nitro, a thio, an amino, a hydroxy, a ketone, an aldehyde, an ester, an amide, a lower aliphatic, a substituted lower aliphatic, or a ring (aryl, substituted aryl, cycloaliphatic, or substituted cycloaliphatic). Examples of such groups include, but are not limited to, 1-chlorodecalyl and the like.

The term "substituted cycloalkyl" as used herein includes cycloalkyl groups having from 1 to 5 (in particular 1 to 3) substituents including without limitation alkyl, alkenyl, alkoxy, cycloalkyl, substituted cycloalkyl, acyl, acylamino, acyloxy, amino, aminoacyl, aminoacyloxy, oxyacylamino, cyano, halogen, hydroxyl, carboxyl, carboxylalkyl, keto, thioketo, thiol, thioalkoxy, aryl, aryloxy, heteroaryl, heteroaryloxy, hydroxyamino, alkoxyamino, and nitro.

The term "substituted heterocyclic" as used herein refers to a cycloalkane and/or an aryl ring system, possessing less than 8 carbons, or a fused ring system consisting of no more than three fused rings, where at least one of the ring carbon atoms is replaced by oxygen, nitrogen or sulfur, and where at least one of the aliphatic hydrogen atoms has been replaced by a halogen, hydroxy, a thio, nitro, an amino, a ketone, an aldehyde, an ester, an amid; a lower aliphatic, a substituted lower aliphatic, or a ring (aryl, substituted aryl, cycloaliphatic, or substituted cycloaliphatic). Examples of such groups include, but are not limited to 2-chloropyranyl.

The term "sulfonyl" as used herein used alone or linked to other terms such as alkylsulfonyl or arylsulfonyl, refers to the divalent radicals —$SO_2^-$. In aspects of the disclosure, the sulfonyl group may be attached to a substituted or unsubstituted hydroxyl, alkyl group, ether group, alkenyl group, alkynyl group, aryl group, cycloalkyl group, cycloalkenyl group, cycloalkynyl group, heterocyclic group, carbohydrate, peptide, or peptide derivative.

The term "substituted aliphatic" as used herein refers to an alkyl or an alkane possessing less than 10 carbons. The term "substituted aliphatic" refers to an alkyl or an alkane possessing less than 10 carbons where at least one of the aliphatic hydrogen atoms has been replaced by a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic, etc.). Examples of such groups include, but are not limited to, 1-chloroethyl and the like.

The term "thioalkoxy" as used herein, alone or in combination, refers to a chemical functional group where a sulfur atom (S) is bonded to an alkoxy group with the general chemical formula —$SR_{24}$ where $R_{24}$ is an alkoxy group which may be substituted. A "thioalkoxy group" may have 1-6 carbon atoms i.e. a —S—(O)—$C_1$-$C_6$ alkyl group wherein $C_1$-$C_6$ alkyl have the meaning as defined above. Illustrative examples of a straight or branched thioalkoxy group or radical having from 1 to 6 carbon atoms, also known as a $C_1$-$C_6$ thioalkoxy, include thiomethoxy and thioethoxy.

The term "thioalkyl" as used herein, alone or in combination, refers to a chemical functional group where a sulfur atom (5) is bonded to an alkyl, which may be substituted. Examples of thioalkyl groups are thiomethyl, thioethyl, and thiopropyl. A thioalkyl may be substituted with a substituted or unsubstituted carboxyl, aryl, heterocyclic, carbonyl, or heterocyclic.

The term "thioaryl" as used herein, alone or in combination, refers to a chemical functional group where a sulfur atom (S) is bonded to an aryl group with the general chemical formula —$SR_{23}$ where $R_{23}$ is aryl which may be substituted. Illustrative examples of thioaryl groups and substituted thioaryl groups are thiophenyl, chlorothiophenol, para-chlorothiophenol, thiobenzyl, 4-methoxy-thiophenyl, 4-nitro-thiophenyl, and para-nitrothiobenzyl.

The term "thiol" as used herein means —SH. A thiol may be substituted with a substituent disclosed herein, in particular alkyl (thioalkyl), aryl (thioaryl), alkoxy (thioalkoxy) or carboxyl. A thiol may be substituted with a substituted or unsubstituted heteroaryl or heterocyclic, in particular a substituted or unsubstituted saturated 3 to 6-membered heteromonocyclic group containing 1 to 4 nitrogen atoms (e.g. pyrrolidinyl, imidazolidinyl, piperidinyl, and piperazinyl) or a saturated 3 to 6-membered heteromonocyclic group containing 1 to 2 oxygen atoms and 1 to 3 nitrogen atoms (e.g. morpholinyl; sydrionyl), especially a substituted morpholinyl or piperidinyl.

DISCUSSION

Figure 1A:
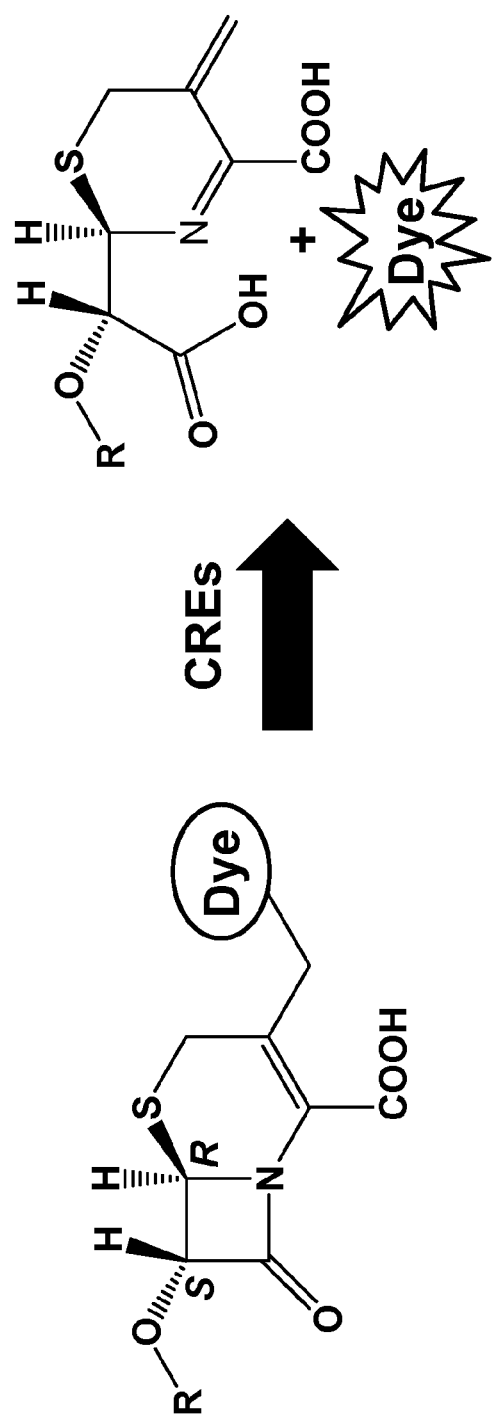
FIG. 1A illustrates the design rationale for embodiments of fluorogenic probes of the disclosure.
Figure 1B:
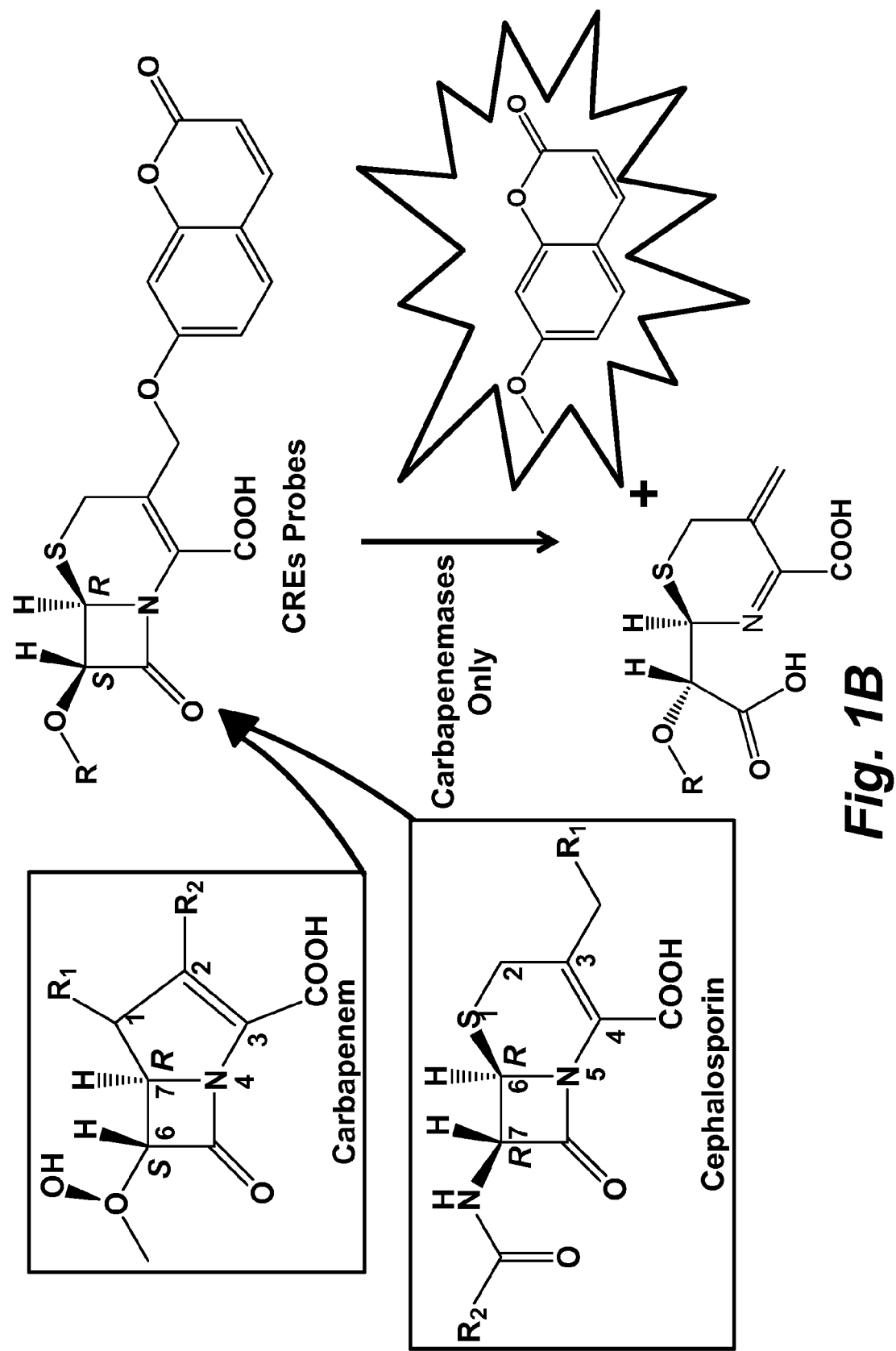
FIG. 1B illustrates the design rationale for fluorogenic probes targeting carbapenemases and their general structures. In these embodiments the fluorophore is linked to the cephalosporin moiety by —O— but such a link can also be, for example, —N— or —S—.

Carbapenem is highly resistant to most β-lactamases, and has an S configuration at its C-6 position and an R configuration at C-5 position, as shown in FIG. 1B. This trans configuration of the β-lactam ring at the C-5 and C-6 positions provides antibiotics with good stability against β-lactamases (Basker et al., (1980) *J. Antibiot.* (Tokyo) 33: 878-884). In comparison, other lactams such as the cephalosporins, a class of β-lactam antibiotics originally derived from the fungus *Acremonium* that has been commonly used as the scaffold to develop probes for β-lactamases (Gao et al., (2003) *J. Am. Chem. Soc.* 125: 11146-11147; Zlokarnic et al., (1998) *Science* 279: 86-88; Xing et al., (2005) *J. Am. Chem. Soc.* 127: 4158-4159; Kong et al., (2010) *Proc. Natl.*

*Acad. Sci. USA* 419: 9-16; Xie et al., (2012) *J. Nat. Chem.* 4: 802-809) generally possess an R configuration at the corresponding C-7 position.

The present disclosure encompasses embodiments of a probe useful for the selective detection of metallo-β-lactamases, in particular carbapenemases, thereby distinguishing those species of bacteria that are carbapenem-resistant from bacterial strains that are sensitive. Cephalosporin-based probes for the detection of antibiotic-resistant bacteria that have the 6,7 R,R configuration are susceptible to cleavage by β-lactamases but cannot distinguish between cleavage by metallo-β-lactamases and other β-lactamases. It has now been found that by modifying the 6,7 position of the β-lactam ring from the R,R configuration to S,R allows cephalosporin to be cleavable by a metallo-β-lactamases, i.e. carbapenemases, but are substantially not cleavable by other lactamases. In addition, it has been found that by modifying a side group of the cephalosporin, selectivity can be introduced that allows the probes of the disclosure to distinguish between various types of metallo-β-lactamases and hence to more narrowly define the strain of bacteria and the type of metallo-β-carbapenemase produced. Accordingly, the disclosure provides probes that are useful for identifying the presence of a carbapenem-resistant bacterial strain and to further characterize the strain to a specific type of enzyme.

In particular, embodiments of the probes of the disclosure can be modified by substitutions at the C-7 position by varying the alcohol used in the synthetic step. The examples of the disclosure thus incorporate side groups that vary in size from a simple methyl moiety to a substituted phenyl group attached to the cephalosporin by an oxy-linkage. It is contemplated, however, that other side-groups may be selected that may allow further definition of the metallo-β-lactamase.

The probes of the disclosure are useful for detecting a bacterial metallo-β-lactamase in a biological sample such as a body fluid, including blood, saliva, urine, and the like, a tissue in a subject human or animal or isolated therefrom, or in a suspension or culture of a cultured population of bacteria.

The probes may be in free solution, or tethered to a solid support for contact with a test sample. Such methods of tethering the probes to such supports as well as the detection system selected and/or adapted for the detection of the released labelling moiety are well-known in the art.

The modified cephalosporins of the disclosure, therefore, have been engineered to include the conversion of the R configuration of the cephalosporin to S configuration to render it specific for carbapenemases, i.e. cleavable by carbapenemases, but not cleavable, or to a substantially lesser extent, by other lactamases.

As shown in FIGS. 1A and 1B, the carbapenemase-specific probes of the disclosure can also comprise a detectable labelling moiety such as, but not limited to, a fluorophore. Suitable fluorophores that may be advantageously incorporated into the probes of the disclosure include, but are not limited to, such as an alkylated umbelliferone (7-hydroxycoumarin) attached to the cephalosporin at the 3'-position thereof. Such attached labelling moieties fluoresce little when excited at 363 nm. However, once the cephalosporin is hydrolyzed by a carbapenemase the fluorophore is released, leading to a detectable fluorescence emission. Other advantageous labels that may be incorporated into the probes of the disclosure are the luciferins. A particularly advantageous luciferin, and derivatives thereof, is the firefly D-luciferin having the formula (4S)-2-(6-hydroxy-1,3-benzothiazol-2-yl)-4,5-dihydrothiazole-4-carboxylic acid that may, for example be linked to the probe through the 6-hydroxy position. It is, however, contemplated that any fluorophore that is detectable after cleavage from the probe may be usefully incorporated into the probes of the disclosure.

Figure 4:
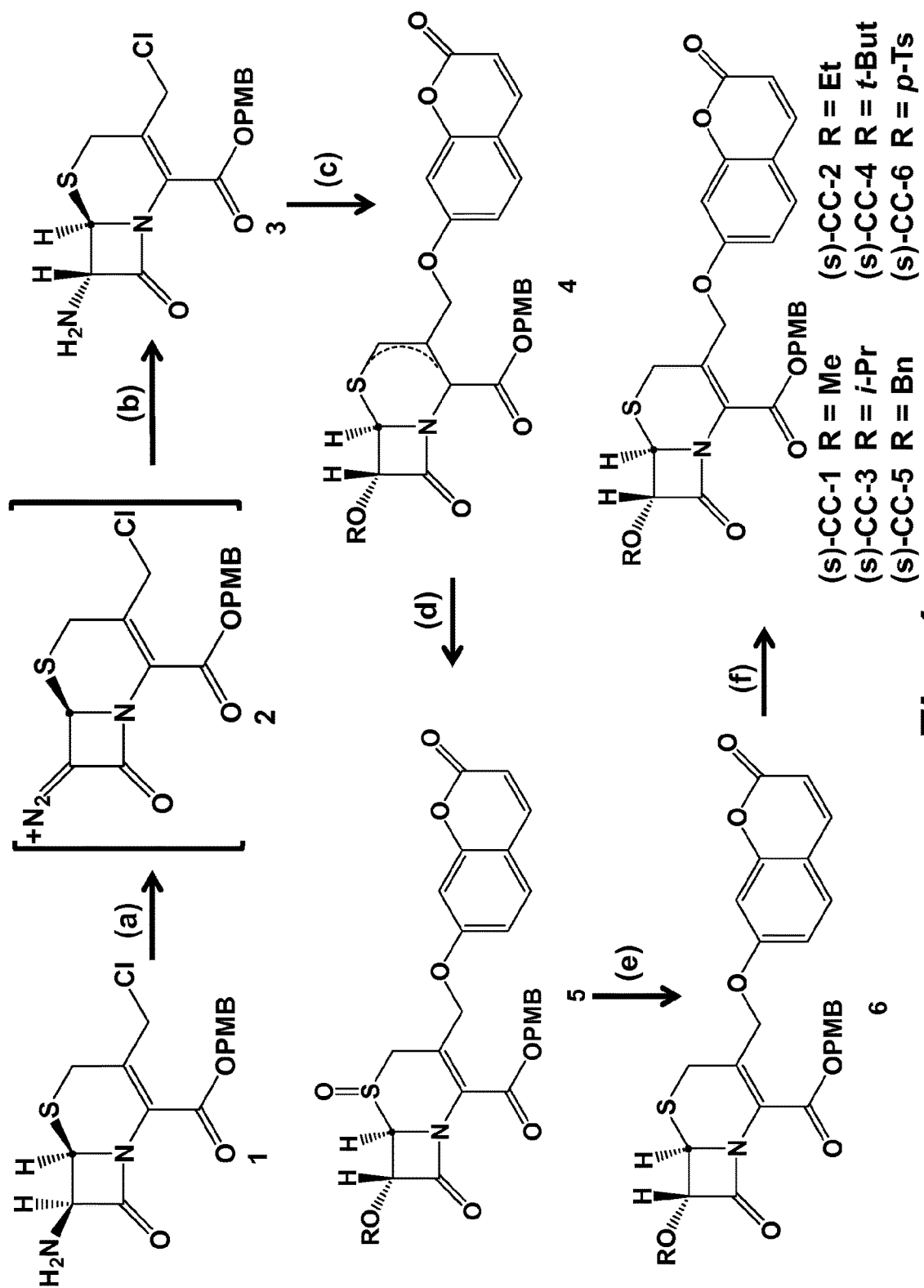
FIG. 4 schematically illustrates the synthesis of fluorogenic probes targeting carbapenemases of the disclosure. (a) $NaNO_2$, 2N $H_2SO_4$, DCM, 0° C., 1 h. (b) ROH, p-TsOH, DCM, 0° C. to room temperature (r.t.) overnight. (c) i): NaI, acetone, r.t, 1 h; ii). 7-hydroxycoumarin, $K_2CO_3$, $CH_3CN$, r.t., 2.5 h. (d) 1.0 eqv. m-CPBA, DCM, 0° C., 0.5 h. (e) NaI, TFAA, acetone, 0° C., 1 h. (f) DCM:TFA:TIPS:$H_2O$=65:30:2.5:2.5, 30 min, 0° C.

Several fluorogenic probes, each comprising a cephalosporin moiety having the S configuration at the C-7 position were synthesized according to a scheme as shown in FIG. 4. The inversion of configuration in cephalosporin was achieved by an SN2 reaction between alcohols and a diazo ketone intermediate, as has been described by Doherty et al., (1990) *J. Med. Chem.* 33: 2513-2521, which is incorporated herein by reference in its entirety, that was prepared from the para-methoxybenzyl (PMB) ester of 7-aminocephalosporanic acid (1) with $NaNO_2$ under acidic conditions in a quantitative yield. The R group of the alcohol can be varied to generate a panel of probe variants useful for determining the substrate preferences of carbapenemases. All the probes were purified by HPLC and structurally characterized by NMR and mass spectra (MS) before use in biological assays.

The specificities of the fluorescent probe embodiments of the disclosure to selectively detect carbapenemases as opposed to other lactamases were examined using recombinant β-lactamases. Four carbapenemases, i.e. the metallo-β-lactamases VIM-27, IMP-1, and NDM-1, and the class A β-lactamase KPC-3 were expressed following the protocol as described in Wang et al., (2006) *Antimicrob. Agents Chemother.* 50: 2762-2771, incorporated herein by reference in its entirety. Two non-carbapenemase class A β-lactamases, TEM-1 Bla and BlaC, were also expressed for use as negative controls.

Figure 5:
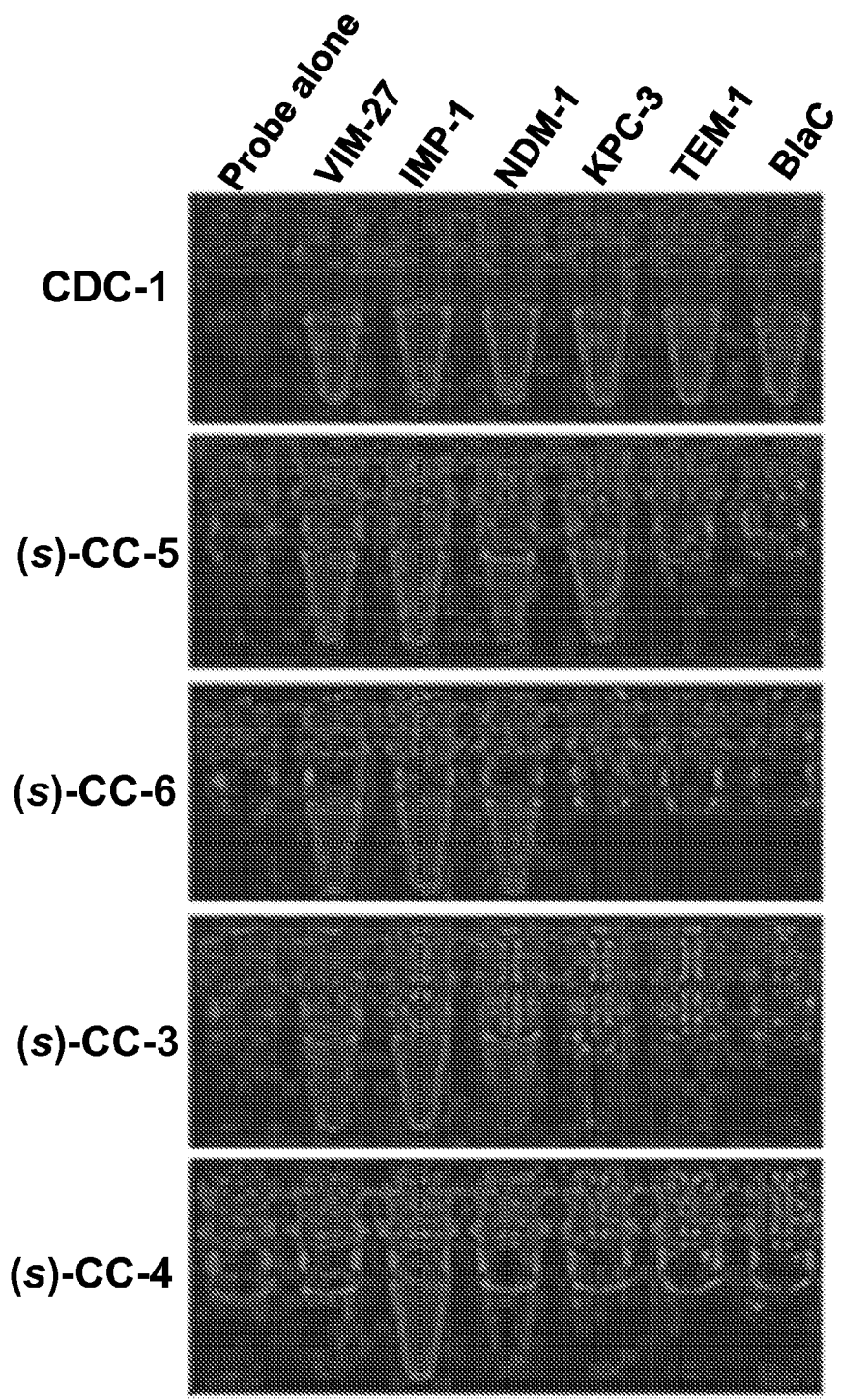
FIG. 5 shows a series of digital images illustrating β-lactamase selectivity of probe (s)-CC-2. Relative fluorescence of indicated amount of β-lactamases after incubation with probes (10 μM) at r. t in 25 μL 1×PBS buffer (pH=7.4) for 2 h. The lactamases are, from left to right in each figure: VIM-27, IMP-1, NDM-1, KPC-3, TEM-1, and BlaC. Relative fluorescence represents the difference in fluorescence intensity with and without β-lactamase incubation. Fluorescence was measured with excitation at 363 nm and emission at 454 nm (band width=5/7.5 nm). Error bars are ±SD.
Figure 6:
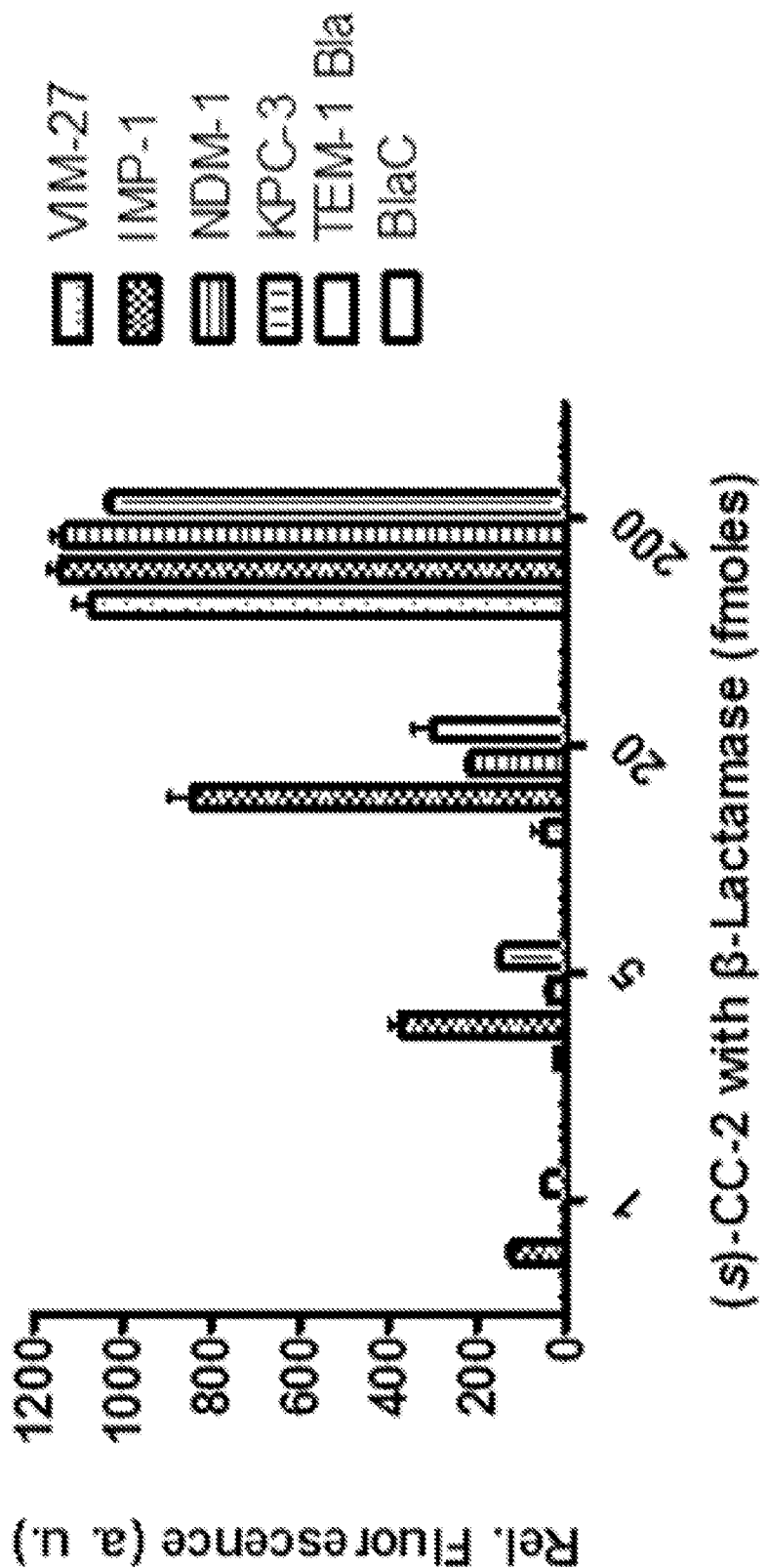
FIG. 6 illustrates imaging of recombinant β-lactamases. Indicated probes (10 μM) in PBS (1×, pH=7.4) were incubated with various β-lactamases (4 nM) for 2 h at room temperature. Picture was obtained with excitation of UV light (360 nm).
Figure 9E:
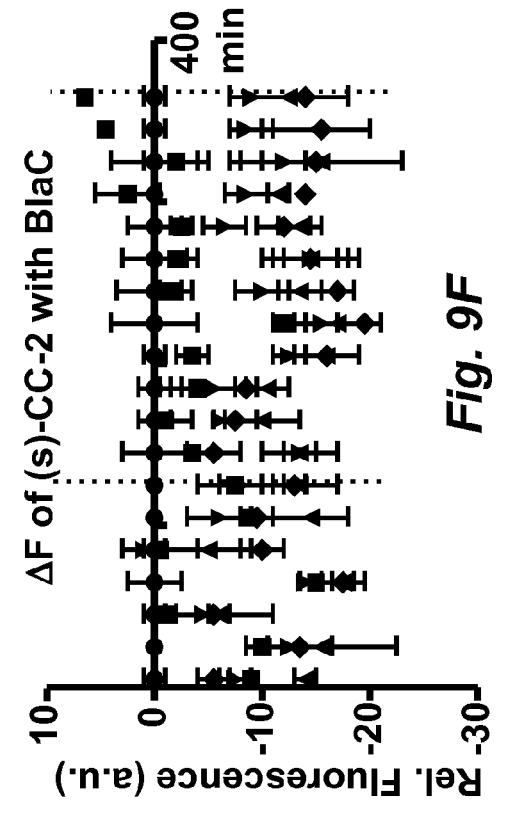
Figure 9F:
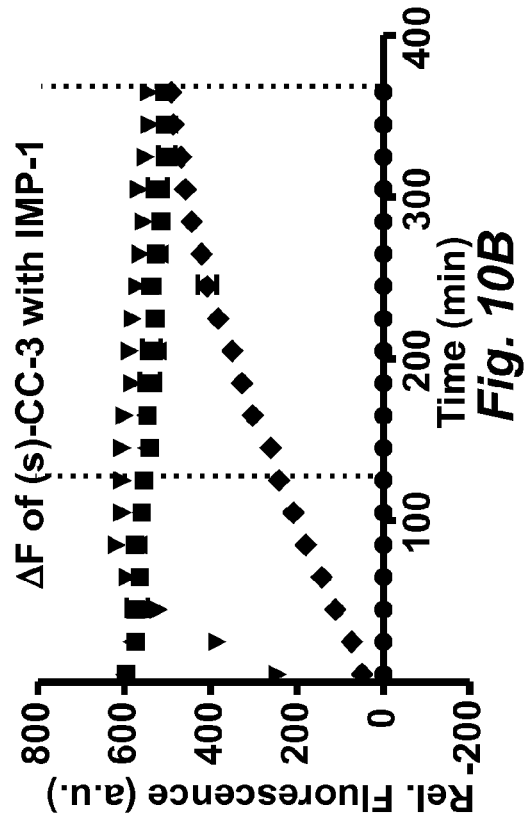
Figure 10A:
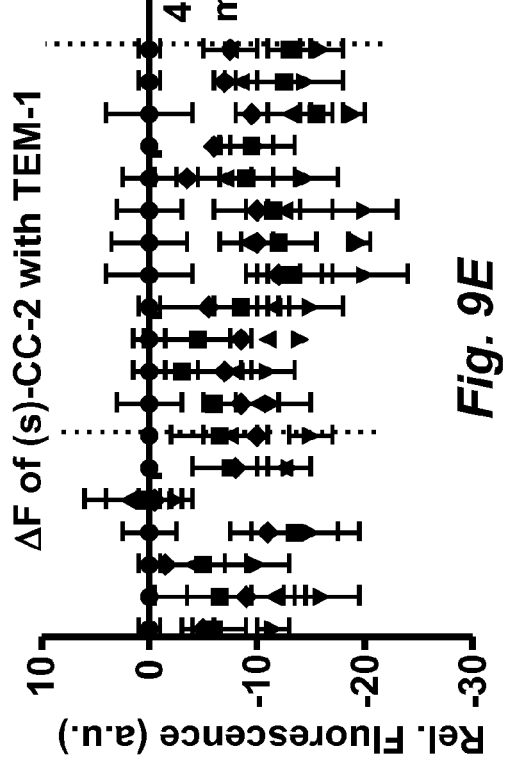
Figure 10B:
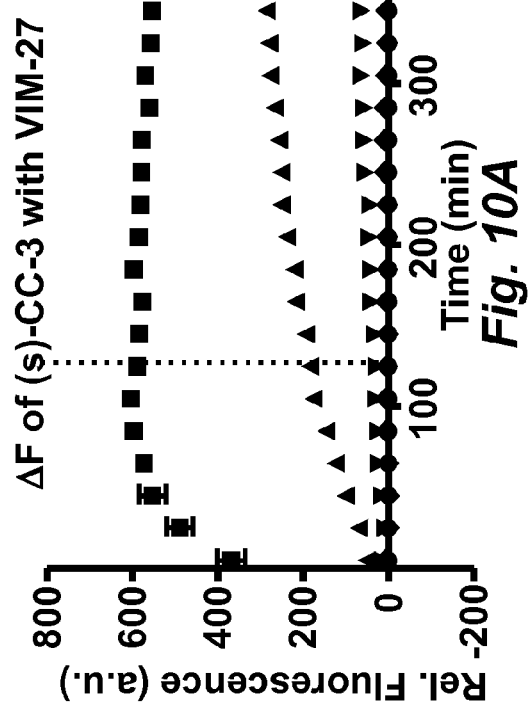
Figure 11A:
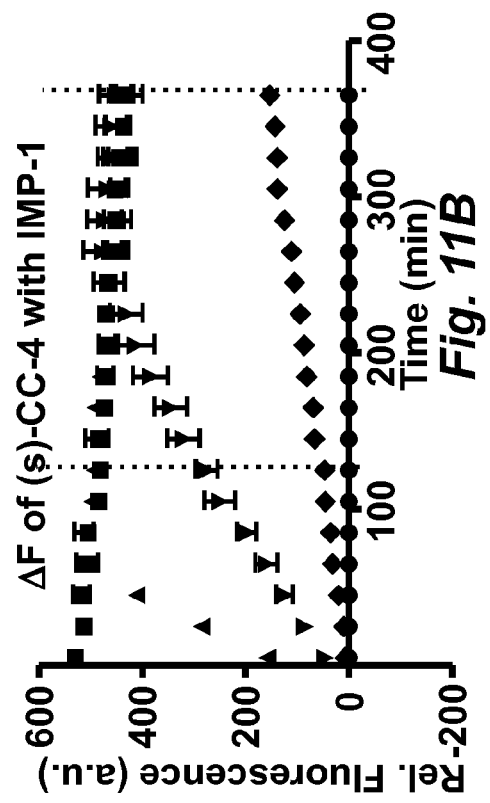
Figure 11B:
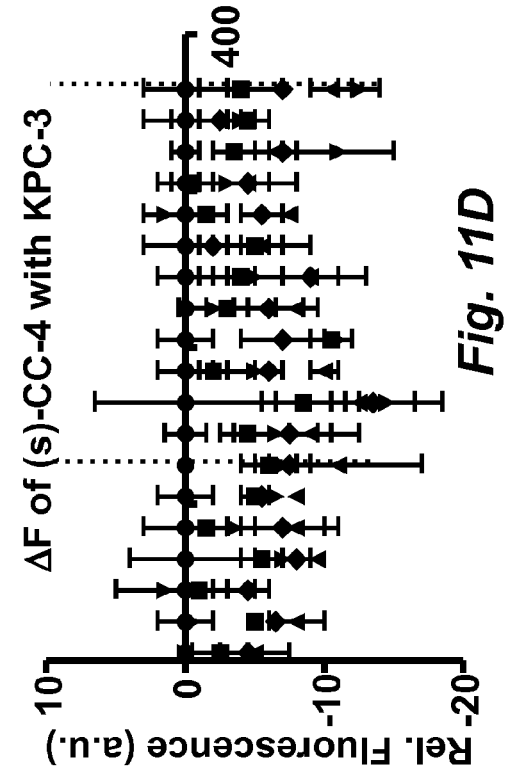
Figure 11C:
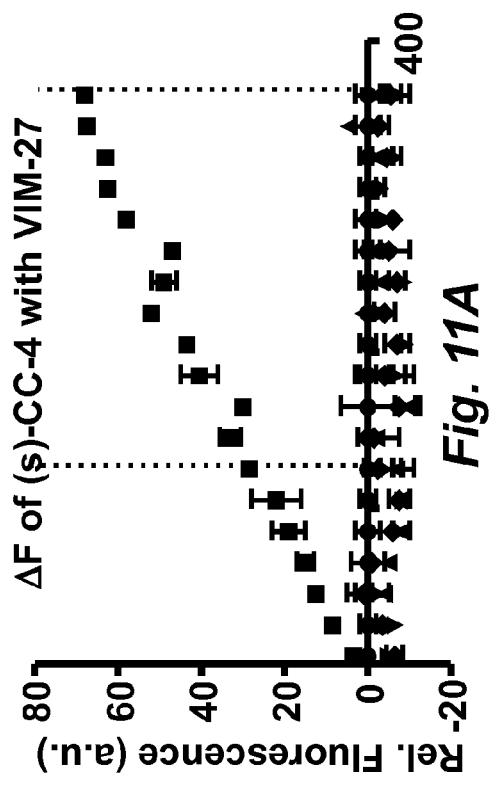
Figure 11D:
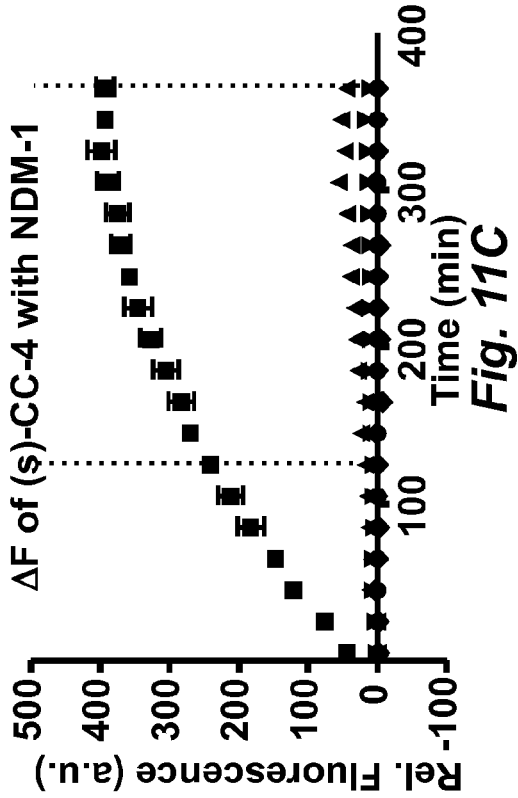
Figure 13A:
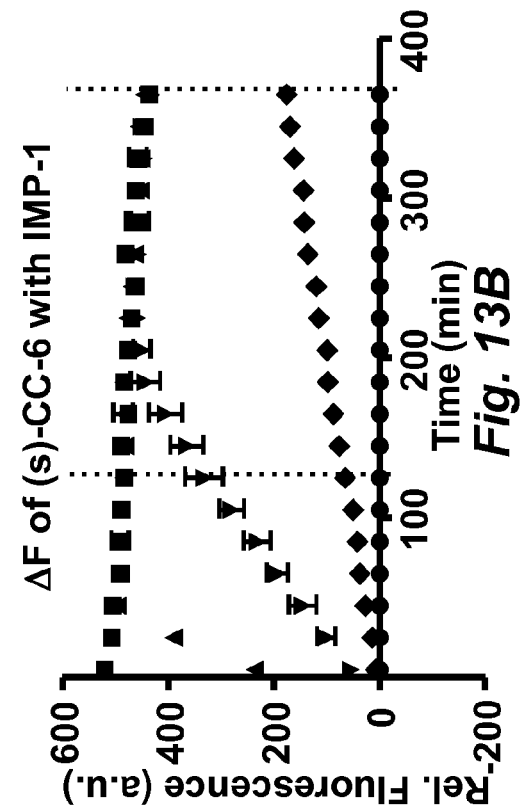
Figure 13B:
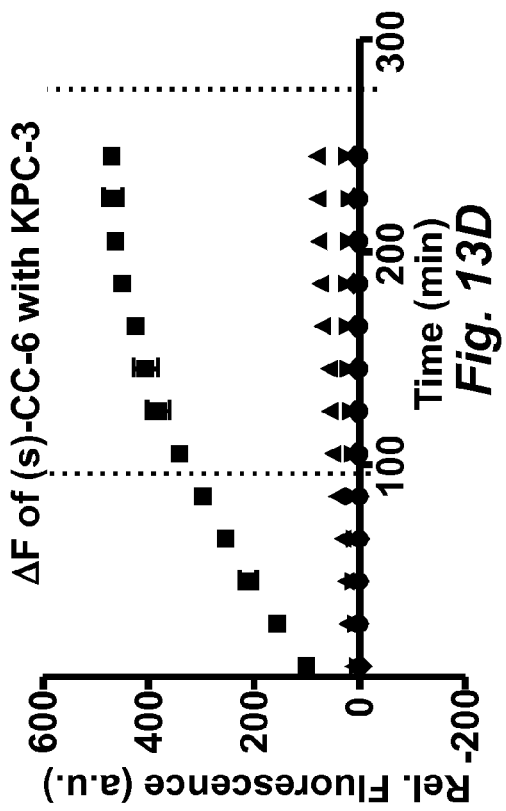
Figure 13C:
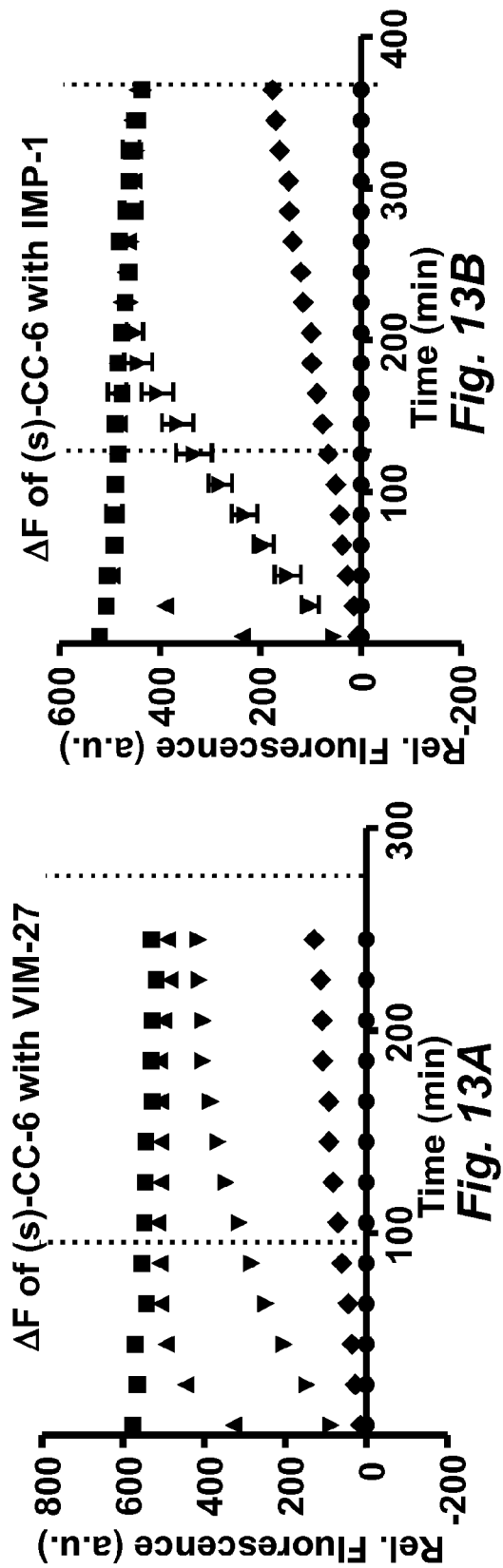
Figure 13D:
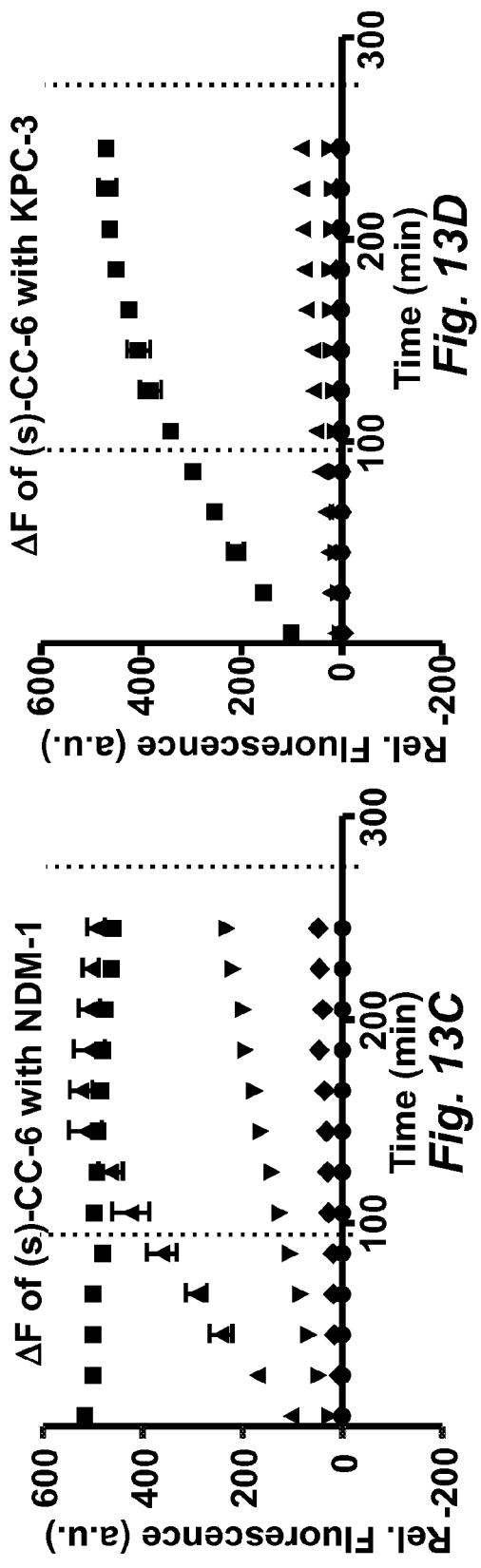
Figure 14B:
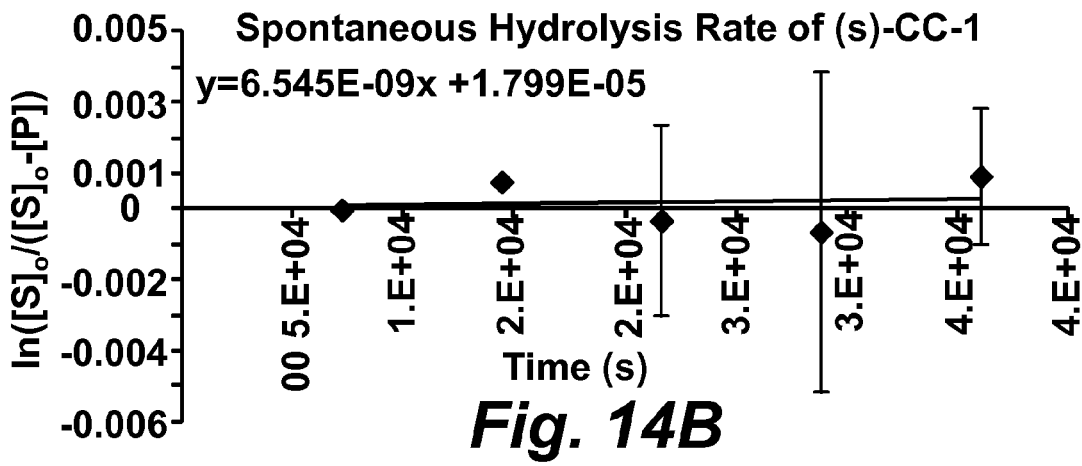
Figure 14C:
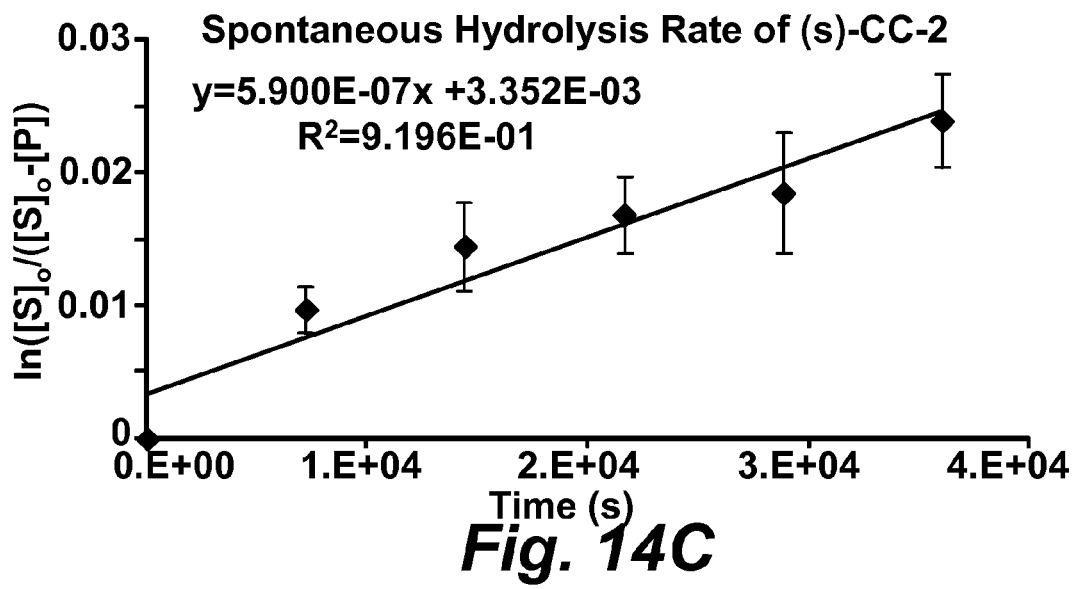
Figure 14D:
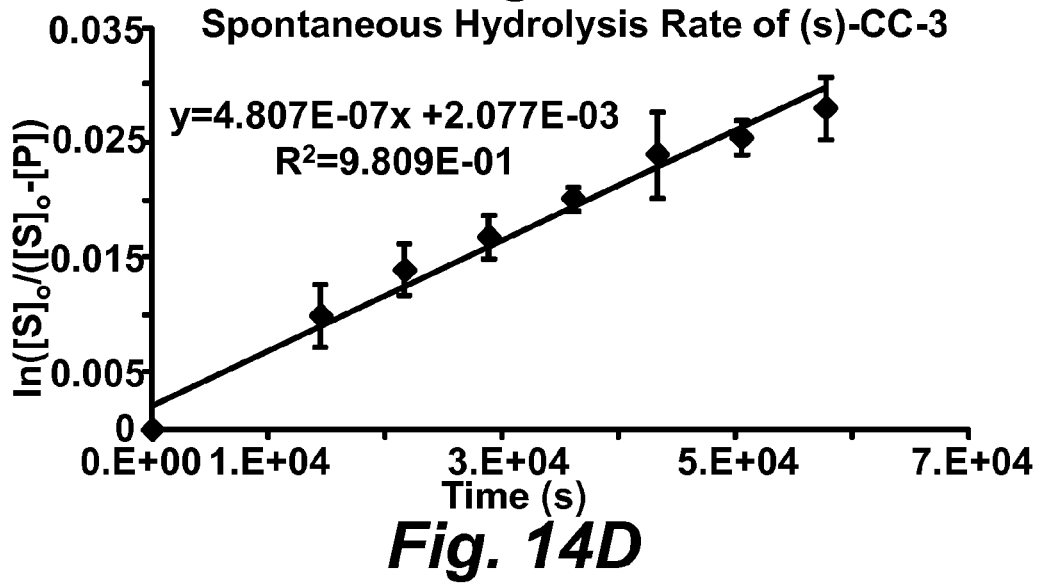
Figure 14E:
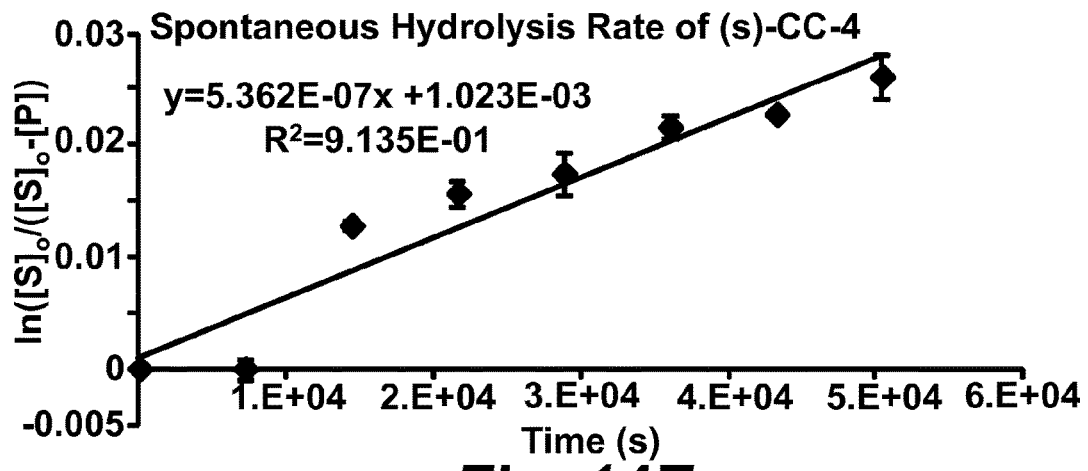
Figure 14F:
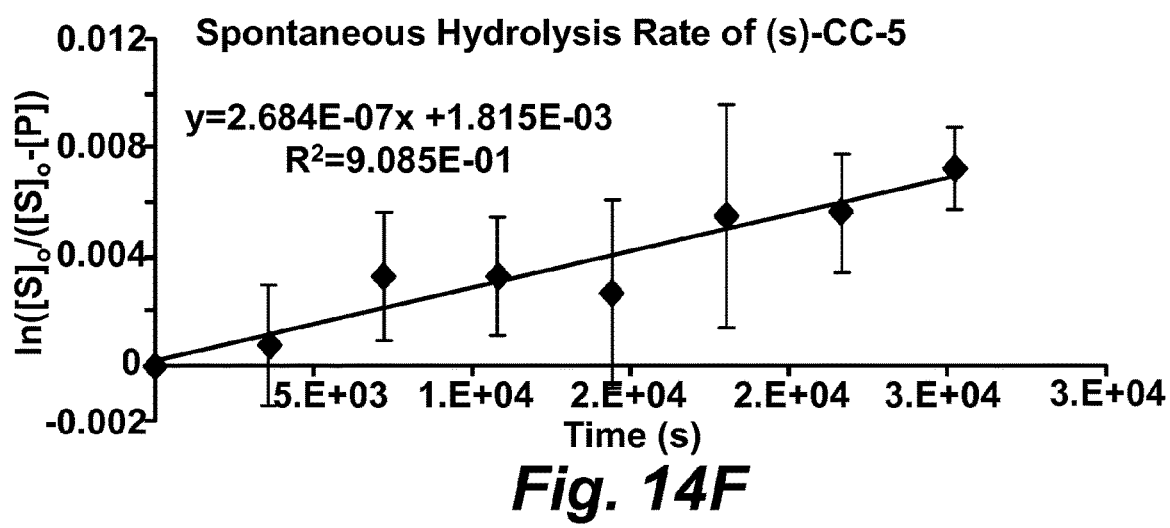
Figure 14G:
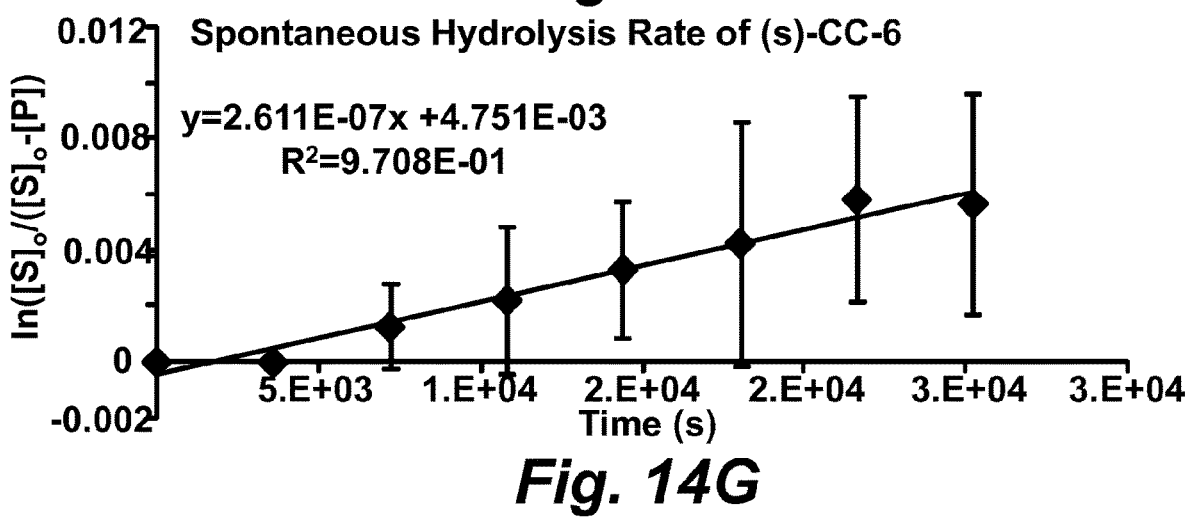

The fluorescence of the probes was measured before and after enzyme treatment using enzyme concentrations in the range of about 1 to about 200 fmols. As shown in FIGS. 2, 5, and 6, the probes showed distinct specificities and sensitivities to the six β-lactamase enzymes VIM-27, IMP-1, and NDM-1, the class A β-lactamase KPC-3 and the non-carbapenemase class A β-lactamases, TEM-1 Bla and BlaC. CDC-1, a previously reported non-specific probe for β-lactamases employed as a positive control, as described by Xie et al., (2012) *J. Nat. Chem.* 4: 802-809, gave positive fluorescence enhancement after exposure to any and all of the enzymes, including the TEM-1 Bla and BlaC controls. However, various modified cephlasporin-based probes of the disclosure exhibited varying degrees of fluorescence when treated with the carbapenemases.

For instance, high fluorescence signals were recorded for (s)-CC-1, (s)-CC-2, and (s)-CC-5 when treated with the carbapenemases VIM-27, IMP-1, NDM-1 and KPC-3, but almost no fluorescence enhancement was observed when the probes were treated with the lactamases TEM-1 Bla and BlaC. Accordingly, the probes (s)-CC-1, (s)-CC-2 and (s)-CC-5 can be said to be specific substrates for, i.e. can specifically detect, carbapenemases. In comparison, (s)-CC-1 and (s)-CC-5 showed greater sensitivity than (s)-CC-2 by providing detectable fluorescence when treated with as low as 1 fmol of all four carbapenemases, indicating (s)-CC-1 and (s)-CC-5 can be specific probes for carbapenemases in general but not for other lactamases.

Figure 2A:
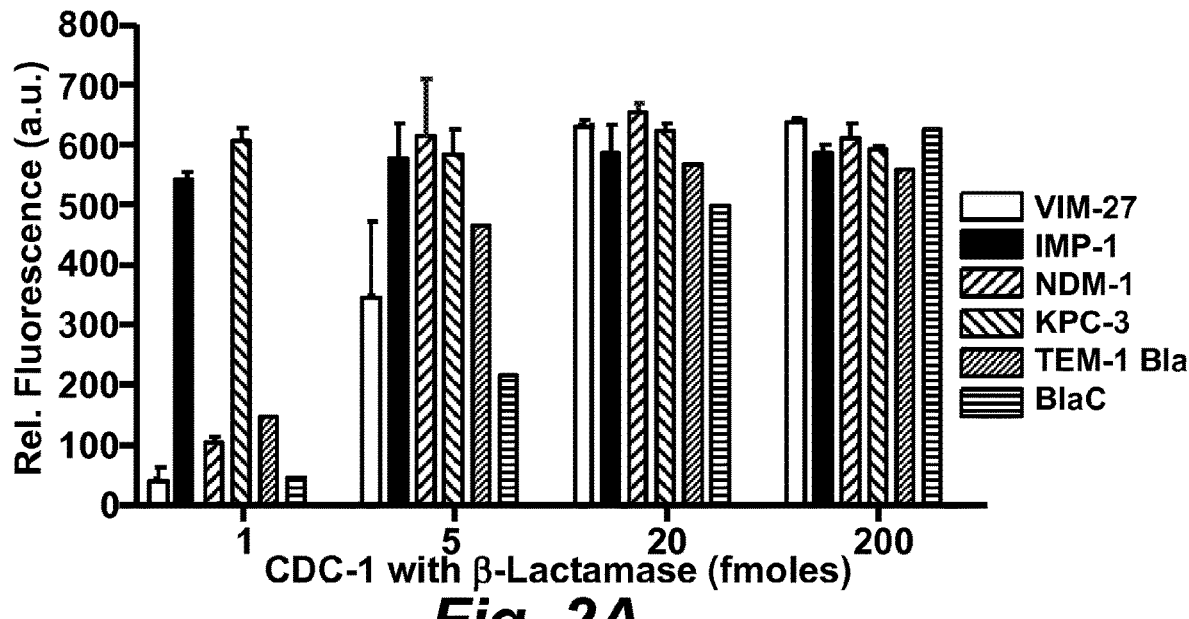
FIGS. 2A-2F is a series of graphs that illustrate β-lactamase selectivity of the probes of the disclosure. Relative fluorescence of indicated amounts of β-lactamases after incubation with probes (10 μM) at room temperature in 25 μL of 1×PBS buffer (pH=7.4) for 2 h.
Figure 2B:
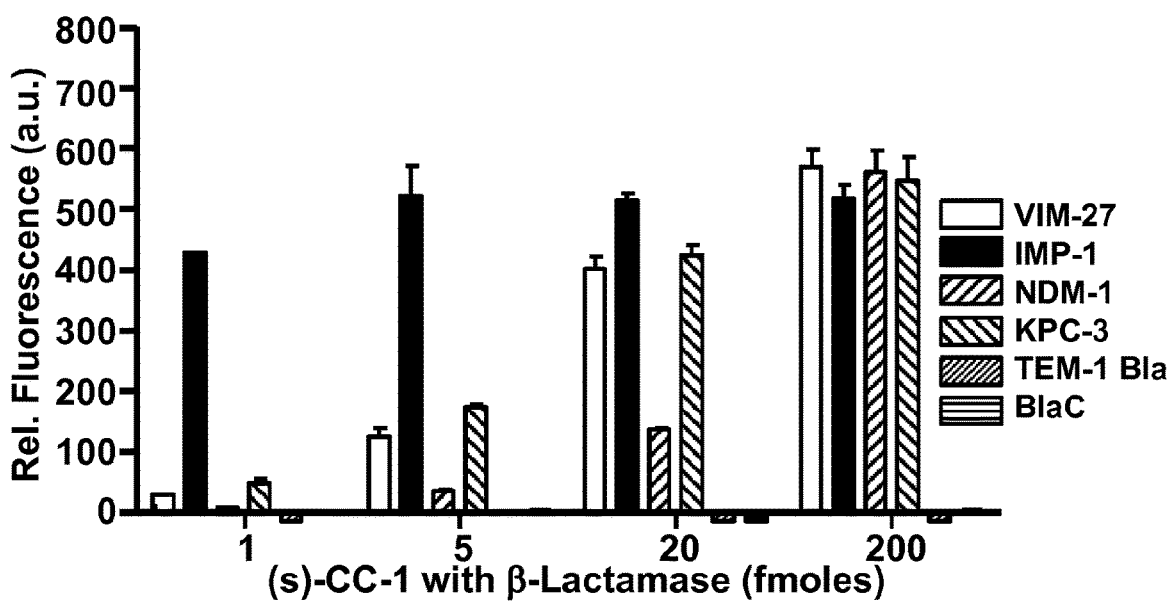
Figure 2C:
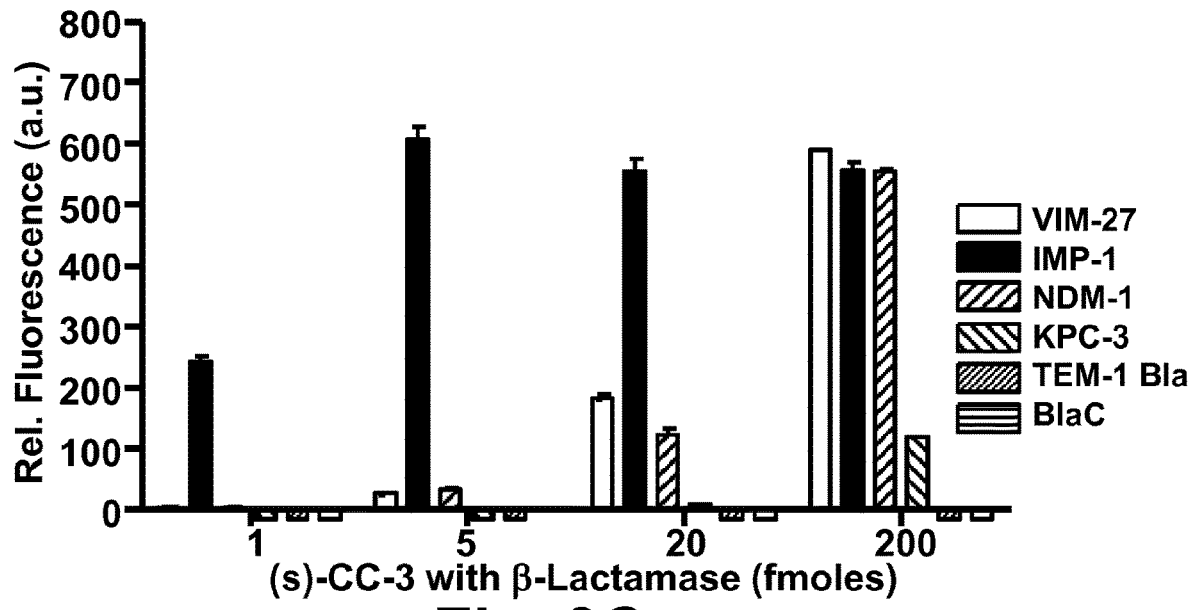

The probes (s)-CC-3 and (s)-CC-6 showed fluorescence enhancement only for the three MBLs VIM-27, IMP-1, and NDM-1, suggesting a general specificity of (s)-CC-3 and (s)-CC-6 for metallo-β-lactamases. Probe (s)-CC-6, however, showed better sensitivity than did (s)-CC-3 since fluorescence enhancement was clearly observed for (s)-CC-6 with as low as 1.0 fmol of the enzymes. When the amount of KPC-3 used in the assay went up to 200 fmols, both probes produced fluorescence signals, as shown in FIGS. 2C and 2F.

Figure 2D:
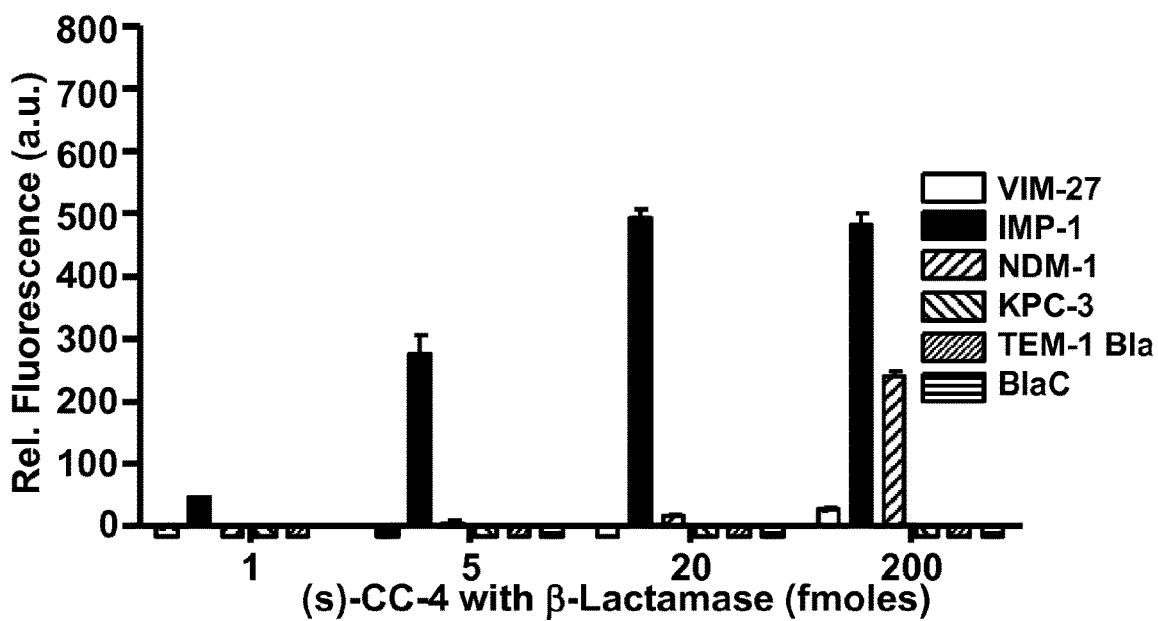
Figure 2E:
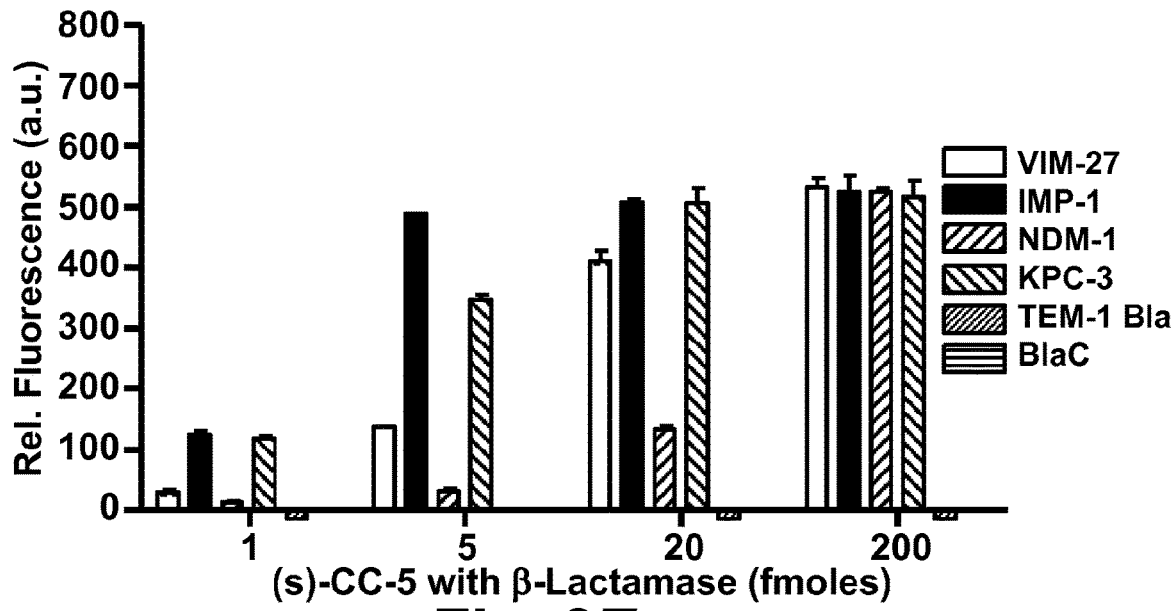
Figure 2F:
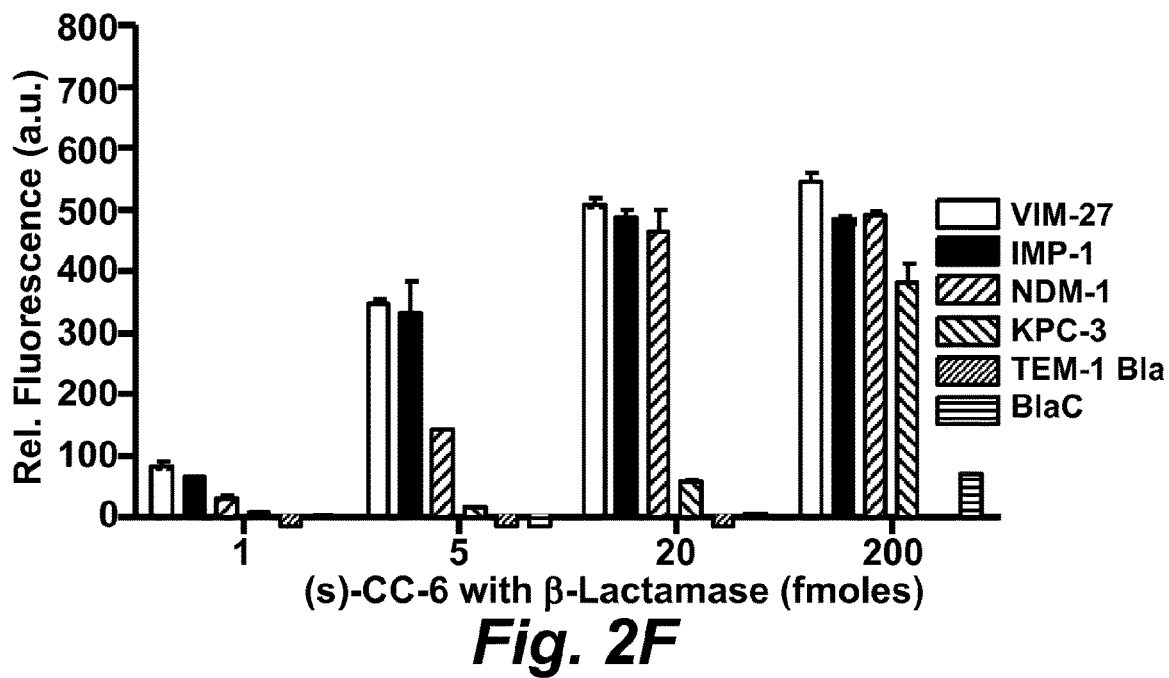
Figure 3A:
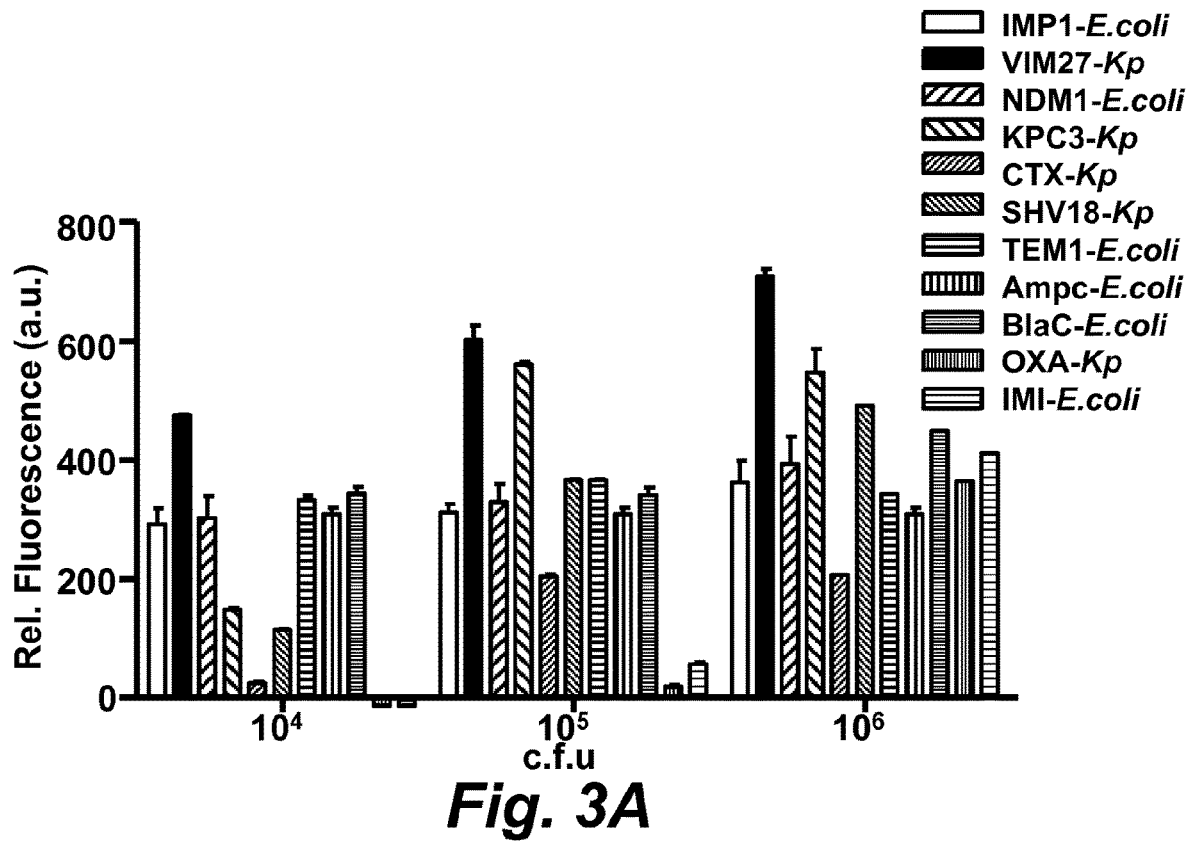
FIGS. 3A-3F is a series of graphs that illustrate the relative fluorescence of β-lactamase-expressing bacteria after incubation with CRE-specific probes (10 μM) at room temperature in 1×PBS buffer (pH=7.4) for 2 h.
Figure 3B:
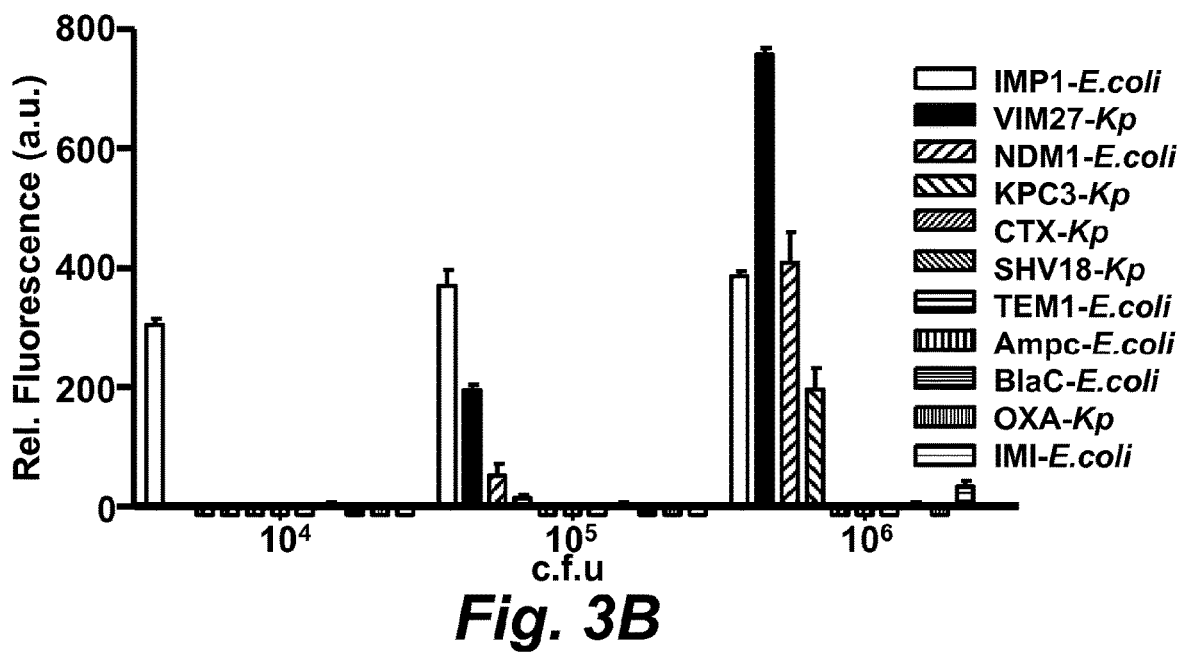
Figure 3C:
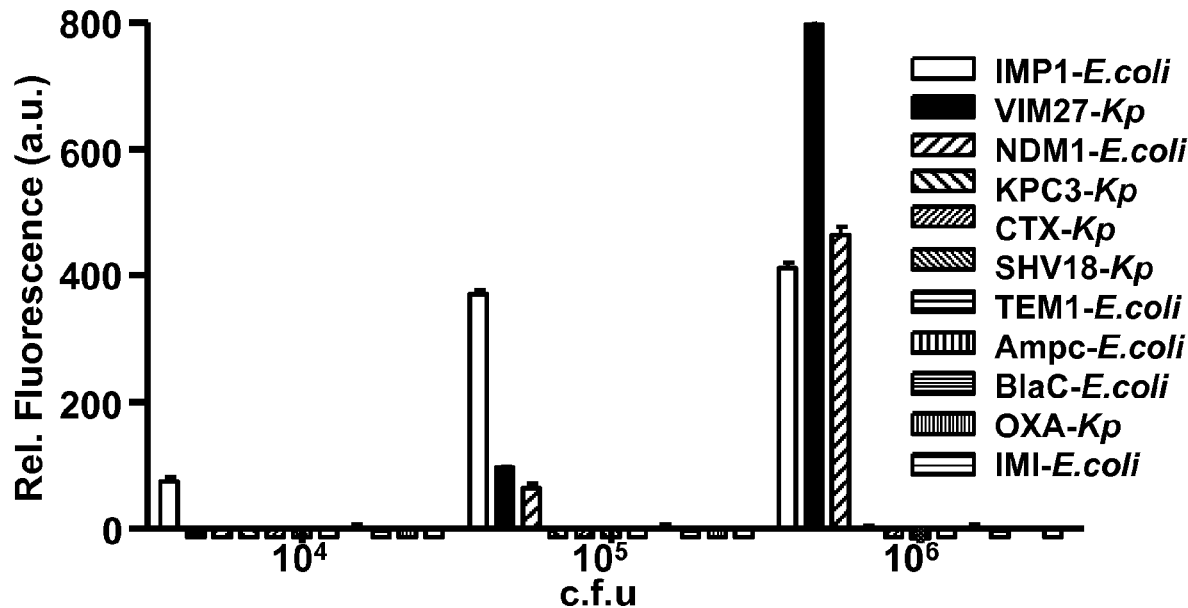
Figure 3D:
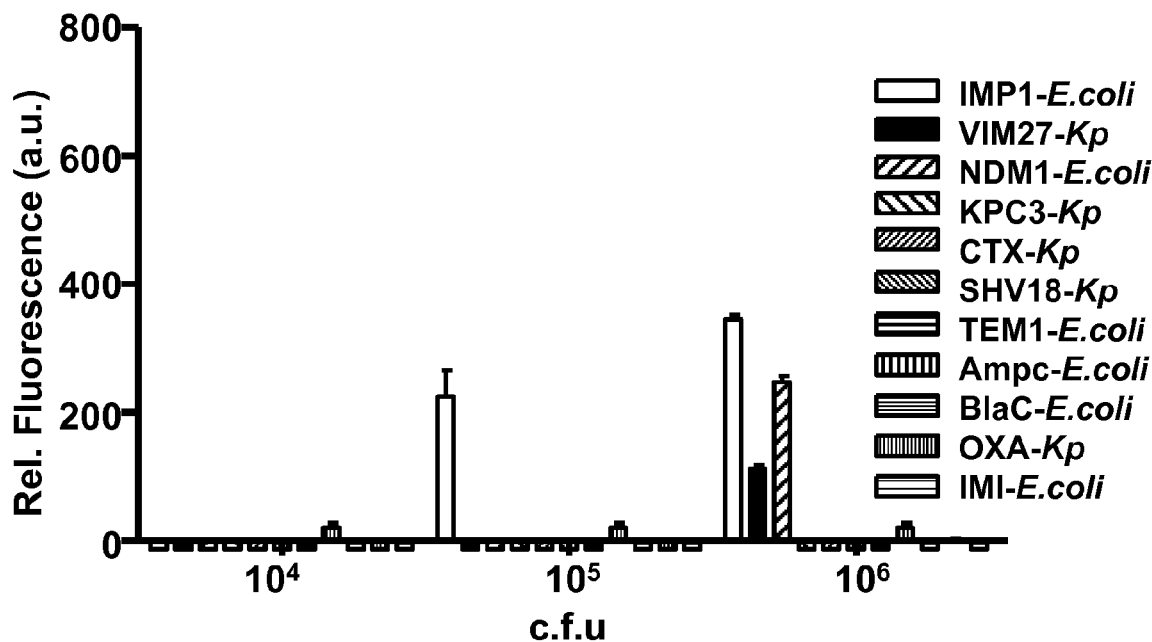
Figure 3E:
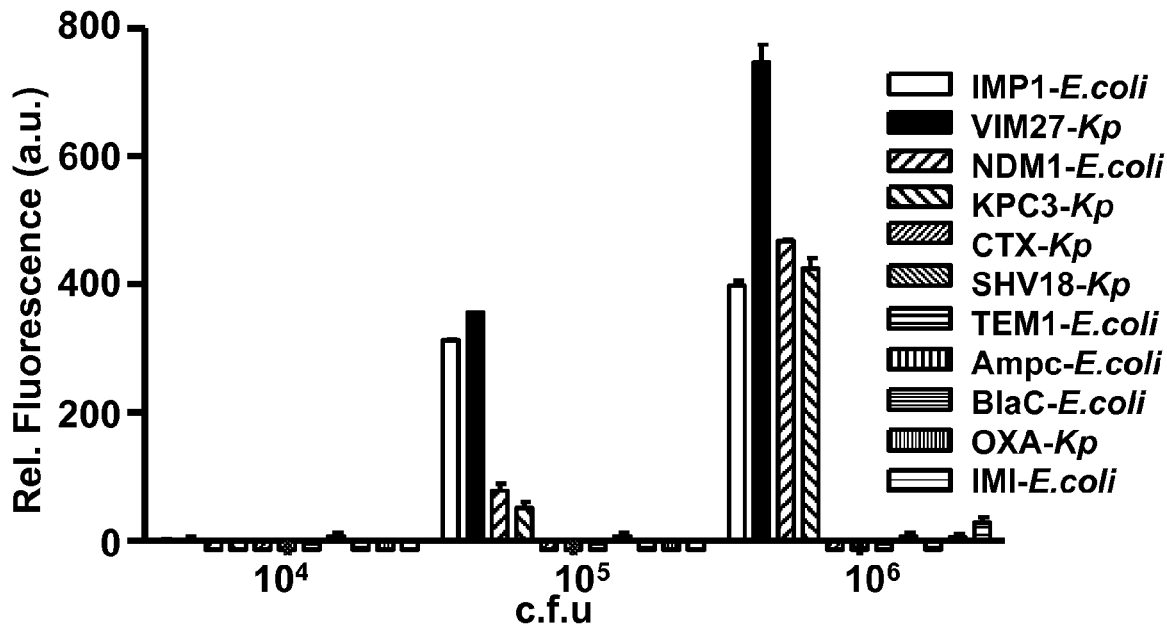
Figure 3F:
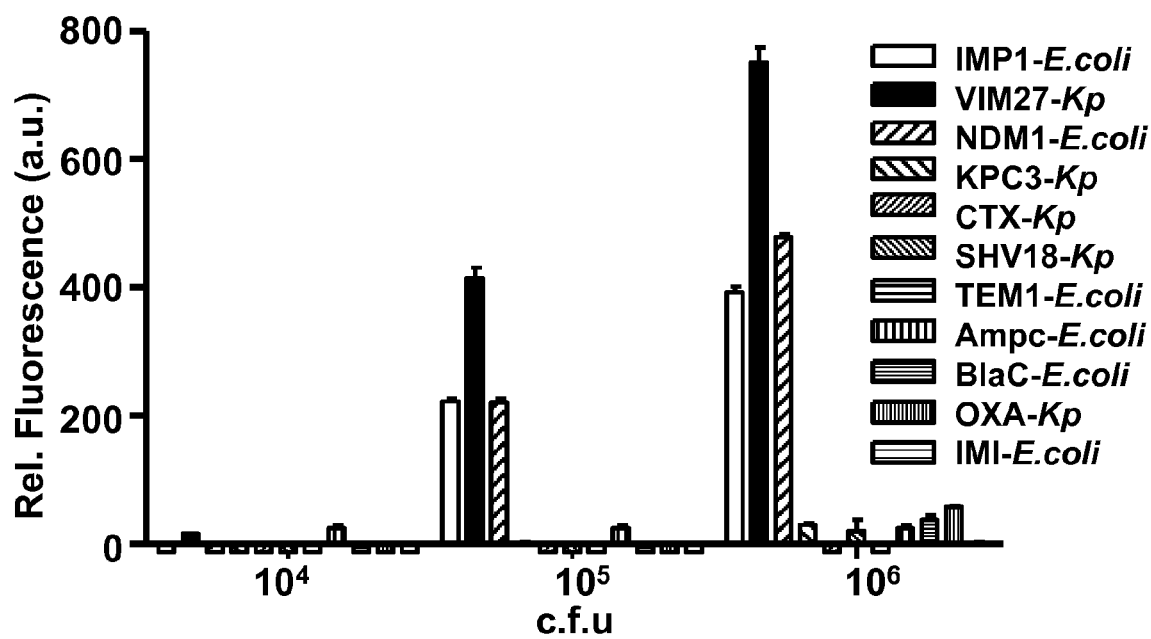

Fluorescent probe (s)-CC-4, as shown in FIG. 2D displayed high specificity for IMP-1 and the fluorescence signal gradually increased in a concentration-dependent manner. A fluorescence increase was only detectable with exposure to NDM-1 at the amount of about 200 fmols. Results indicate that reversing the stereochemistry of the C-7 position of cephalosporin from the R configuration to the S configuration is sufficient to increase the probe specificity to be selective for carbapenemases as opposed to other lactamase species.

The kinetic parameters of the probes of the disclosure with different β-lactamases were determined from Lineweaver-Burk plots and summarized in FIGS. 7A-13F and Table 1.

The usefulness of these probes for detecting carbapenemase-expressing live bacteria has also been demonstrated. Eleven bacteria strains that produced carbapenemases or other clinically prevalent β-lactamases were evaluated, including the class A β-lactamases KPC-3 and IMI, class B MBLs VIM-27, IMP-1, and NDM-1, the class D β-lactamase OXA-48, and the clinically important non-carbapenamases CTX-M, SHV-18, TEM-1, BlaC, and AmpC. The fluorescence response of the probes (10 μM each unless indicated) to varying numbers of live bacteria in a range from $10^4$ to $10^6$ c.f.u., is shown in FIGS. 3A-3F. As a positive control, CDC-1 was consistently positive for all of the bacteria strains, indicating that all the bacteria are β-lactamase active.

Probes (s)-CC-1 and (s)-CC-5 showed high fluorescence enhancement with VIM-27, IMP-1, NDM-1 and KPC-3-expressing bacteria ($>=10^5$ c.f.u.). However, with $10^4$ c.f.u

TABLE 1

| Name | $K_m$ (μM) | $k_{cat}$ (s$^{-1}$) | $k_{cat}/K_m$ (s$^{-1}$M$^{-1}$) | $K_m$ (μM) | $k_{cat}$ (s$^{-1}$) | $k_{cat}/K_m$ (s$^{-1}$M$^{-1}$) | Spontaneous hydrolysis rate (×10$^{-7}$s$^{-1}$) |
|---|---|---|---|---|---|---|---|
| | VIM-27a | | | IMP-1a | | | |
| CDC-1 | 3.8 ± 2.7 | 2.3 ± 0.3 | 7.5 × 10$^5$ | 4.0 ± 0.1 | 7.9 ± 0.1 | 2.0 × 10$^6$ | 2.4[b] |
| (s)-CC-1 | 29.2 ± 7.0 | 1.1 ± 0.1 | 3.8 × 10$^4$ | 7.8 ± 0.2 | 12.2 ± 0.1 | 1.6 × 10$^6$ | 0.7 |
| (s)-CC-2 | 23.0 ± 0.0 | 0.71 ± 0.0 | 3.0 × 10$^4$ | 12.9 ± 1.0 | 16.6 ± 0.1 | 1.3 × 10$^6$ | 5.9 |
| (s)-CC-3 | 61.3 ± 8.8 | 0.5 ± 0.04 | 7.8 × 10$^3$ | 3.2 ± 0.07 | 8.0 ± 0.04 | 2.5 × 10$^6$ | 4.8 |
| (s)-CC-4 | 91.6 ± 10.1 | 0.2 ± 0.01 | 2.6 × 10$^3$ | 9.4 ± 1.3 | 2.1 ± 0.01 | 2.2 × 10$^5$ | 5.4 |
| (s)-CC-5 | 145.1 ± 100.1 | 3.4 ± 1.5 | 2.6 × 10$^4$ | 3.6 ± 0.1 | 4.2 ± 0.03 | 1.2 × 10$^6$ | 2.7 |
| (s)-CC-6 | 14.1 ± 1.2 | 3.9 ± 0.1 | 2.8 × 10$^5$ | 3.4 ± 0.4 | 2.2 ± 0.02 | 6.6 × 10$^5$ | 2.6 |
| | NDM-1a | | | KPC-3a | | | |
| CDC-1 | 5.04 ± 3.2 | 4.6 ± 0.3 | 1.1 × 10$^6$ | 21.0 ± 1.34 | 35.4 ± 0.04 | 1.7 × 10$^6$ | 2.4[b] |
| (s)-CC-1 | 12.0 ± 0.7 | 0.2 ± 0.02 | 2.0 × 10$^4$ | 67.7 ± 4.9 | 1.5 ± 0.05 | 2.3 × 10$^4$ | 0.7 |
| (s)-CC-2 | 14.9 ± 2.7 | 0.3 ± 0.01 | 1.7 × 10$^4$ | 39.1 ± 1.3 | 0.3 ± 0.05 | 6.9 × 10$^3$ | 5.9 |
| (s)-CC-3 | 6.0 ± 3.5 | 0.1 ± 0.01 | 2.0 × 10$^4$ | 250 ± 235 | 0.2 ± 0.17 | 1.1 × 10$^3$ | 4.8 |
| (s)-CC-4 | 58.6 ± 16.0 | 0.3 ± 0.04 | 5.1 × 10$^3$ | 121 ± 85 | 0.2 ± 0.1 | 2.2 × 10$^3$ | 5.4 |
| (s)-CC-5 | 26.7 ± 0.2 | 0.3 ± 0.0 | 1.0 × 10$^4$ | 5.2 ± 0.5 | 1.1 ± 0.01 | 2.2 × 10$^5$ | 2.7 |
| (s)-CC-6 | 4.7 ± 0.3 | 1.9 ± 0.06 | 4.0 × 10$^5$ | 18.7 ± 7.8 | 0.3 ± 0.05 | 2.0 × 10$^4$ | 2.6 |

All probes exhibited high stability with low spontaneous hydrolysis rates ranging from 0.7 to 5.9×10$^{-7}$ s$^{-1}$, as shown in FIGS. 14B-14G. Comparison of the kinetic parameters indicated that all of the probes displayed the best kinetic efficiency (kcat/$K_m$=0.2-2.5×10$^6$ s$^{-1}$M$^{-1}$) with IMP-1, which is the most common metallo-β-lactamase and has a worldwide distribution (Oelschlaeger et al., (2010) *J. Med. Chem.* 53: 3013-3027; Griffin et al., (2011) *Biochemistry* 50: 9125-9134).

Probe (s)-CC-4 with the bulky t-butyl side group showed high specificity and kinetic efficiency (kcat/Km) for IMP-1 (2.2×10$^5$ s$^{-1}$M$^{-1}$), compared to 50 to 100 times that with other carbapenemases. No hydrolysis by non-carbapenemase lactamases was detected. A smaller R group is preferred for hydrolysis by VIM-27 and KPC-3, but less so for IMP-1 and NDM-1.

Probe (s)-CC-5 exhibited much higher kinetic efficiency with IMP-1 and KPC-3 (1.2×10$^6$ s$^{-1}$M$^{-1}$, and 2.2×10$^5$ s$^{-1}$M$^{-1}$, respectively) compared with VIM-27 and NDM-1 (2.6×10$^4$ s$^{-1}$M$^{-1}$, and 1.0×10$^4$ s$^{-1}$M$^{-1}$, respectively). There was no hydrolysis by non-carbapenemase lactamases observed. However, probe (s)-CC-6 showed high kinetic efficiency for IMP-1, NDM-1, and VIM-27 (6.6×10$^5$ s$^{-1}$M$^{-1}$, 4.0×10$^5$ s$^{-1}$M$^{-1}$ and 2.8×10$^5$ s$^{-1}$M$^{-1}$, respectively), levels from about 14 to about 33 times higher than KPC-3 (2.0×10$^4$ s$^{-1}$M$^{-1}$). These kinetic measurements are consistent with the specificity/sensitivity results with recombinant β-lactamases, as shown in FIGS. 2A-2F.

of bacteria, only IMP-1-expressing bacteria could be detected by the probe (s)-CC-1. Probes (s)-CC-3 and (s)-CC-6 had intense fluorescence responses only with VIM-27, IMP-1 and NDM-1, in agreement with the results obtained from recombinant enzyme studies, as shown in FIGS. 2A-2F. In contrast, at least 1.0×10$^5$ to about 1.0×10$^6$ c.f.u. bacteria were required to reliably detect MBL bacteria using the (s)-CC-3 and (s)-CC-6 probes and after a 2 h incubation. Additionally, (s)-CC-4 showed a specific preference for IMP-producing strains with a detection limit of about 1×10$^5$c.f.u. bacteria.

Accordingly, by reversing the stereochemistry at the C7 position of cephalosporin, fluorescent probes have been developed that can specifically detect carbapenemases, and in particular metallo-β-lactamases, produced by CRE bacteria. The substituting group at the C7 position can further modulate the selectivity among carbapenemases to further distinguish between types of the carbapenemases. Thus (s)-CC-3 and (s)-CC-6 demonstrate specificity and sensitivity for MBLs in general as opposed to other lactamases. The probe (s)-CC-4, however, shows high specificity for IMP-1.

While the probes (s)-CC-1 to (s)-CC-6 of the disclosure use the blue fluorophore coumarin, it is contemplated that other fluorophores including, but not limited to, those with a longer emission wavelength, may be used as the fluorophore of the disclosure to improve sensitivity, as reported as reported (Xie et al., (2012) *J. Nat. Chem.* 4: 802-809). It is contemplated that the probes of the disclosure, including with variation in the fluorophore, are useful for the rapid and accurate detection of Carbapenem-Resistant Enterobacteriaceae (CRE) for an early diagnosis and treatment of patients with CRE infections.

It is further contemplated that a variety of detectable labelling moieties may be incorporated into the modified cephalosporin probes of the disclosure such that more than one bacterial strain, each producing a distinguishable species of metallo-3-carbapenemase, may be detectable at the same time. Most advantageously, such detectable moieties provide a detectable signal increase upon hydrolysis of the cephalosporin by a carbapenemase. In some embodiments of the probes of the disclosure, the label is a fluorescent label. By attachment of the label to the cephalosporin, there is quenching of the fluorescence induced by an excitation radiation. In other embodiments, the label can be a dye, or even a radioactive label, that is released from the probe and into a surrounding liquid medium. The released dye may then be separated from the uncleaved probe for detection.

One aspect of the disclosure, therefore encompasses embodiments of a composition comprising a detectable probe selectively cleavable by a metallo-β-lactamase, said probe comprising a cephalosporin having a 6,7-trans configuration and a detectable label attached thereto.

In some embodiments of this aspect of the disclosure the probe can have the formula I or formula II:

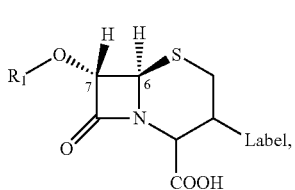

I

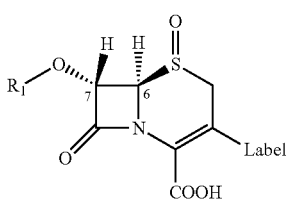

II wherein $R_1$ can be selected from the group consisting of: an alkyl, a substituted alkyl, an aromatic group, a substituted aromatic group, a fluorophore, and a fluorescent quencher.

In some embodiments of this aspect of the disclosure, $R_1$ can be selected from the group consisting of: methyl, ethyl, isopropyl, tert-butyl, benzyl-, and tosyloxy-.

In some embodiments of this aspect of the disclosure the detectable label can be attached to the cephalosporin by an —O—, a —N—, or an —S— link.

In some embodiments of this aspect of the disclosure the detectable label is (2-oxo-2H-chromen-7-yl) (III) or (4S)-2-(6-oxo-1,3-benzothiazol-2-yl)-4,5-dihydrothiazole-4-carboxylic acid (IV) and can have the structures:

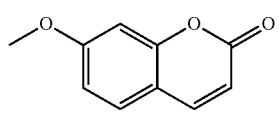

III or

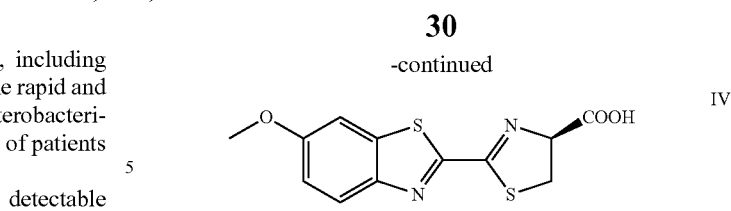

IV

In some embodiments of this aspect of the disclosure the probe can be selected from the group consisting of:

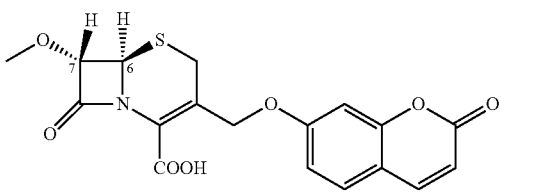

(s)-CC-1

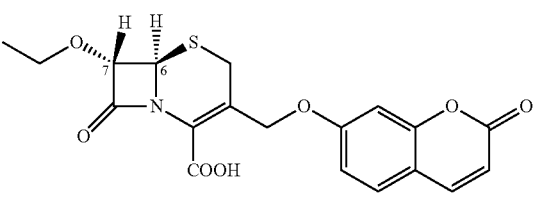

(s)-CC-2

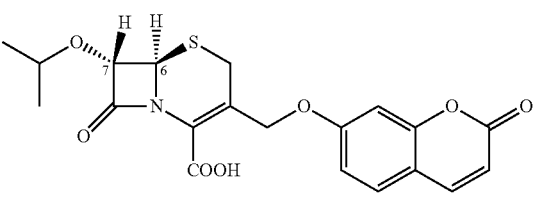

(s)-CC-3

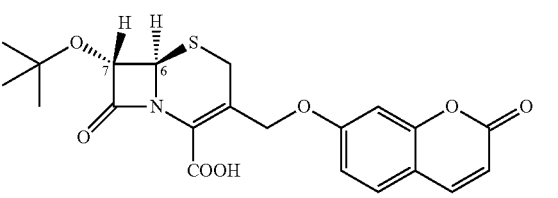

(s)-CC-4

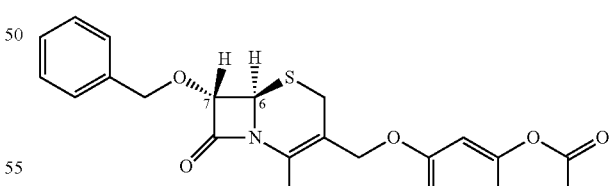

(s)-CC-5

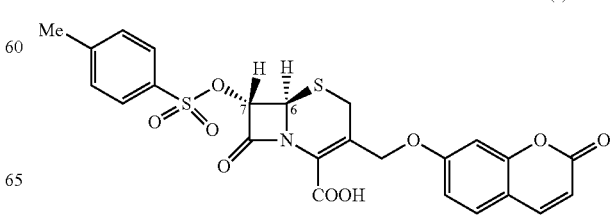

(s)-CC-6

-continued (s)-CC-7
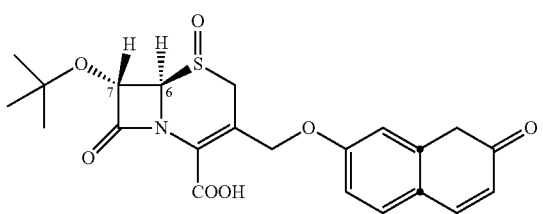

(s)-CL-3
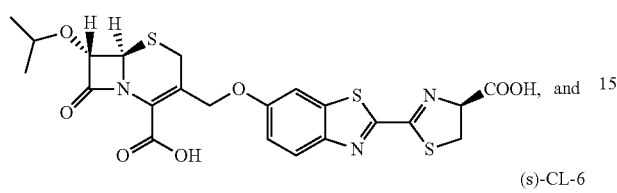

(s)-CL-6
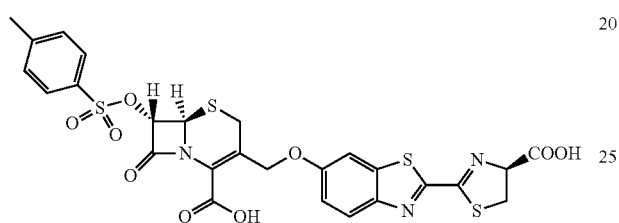

Another aspect of the disclosure encompasses embodiments of a method of selectively detecting a metallo-β-lactamase activity, said method comprising contacting a sample suspected of having a metallo-β-lactamase activity with a composition comprising a detectable probe selectively cleavable by a metallo-β-lactamase, said probe comprising a cephalosporin moiety having a 6,7 trans configuration and a detectable label; allowing an effective period for a metallo-β-lactamase activity to cleave the cephalosporin moiety, thereby releasing the detectable label from the cephalosporin moiety, whereby a detectable signal is generated; and detecting the signal, wherein a detectable signal indicates that the sample contains a metallo-3-lactamase activity or a source of a metallo-β-lactamase activity.

In some embodiments of this aspect of the disclosure the probe has the formula I or formula II:

I
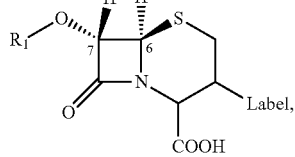

II
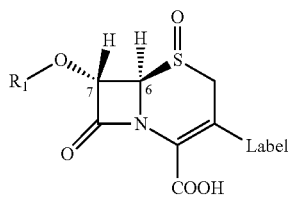

wherein $R_1$ can be selected from the group consisting of: an alkyl, a substituted alkyl, an aromatic group, a substituted aromatic group, a fluorophore, a luciferase substrate, and a fluorescent quencher.

In some embodiments of this aspect of the disclosure $R_1$ is selected from the group consisting of: methyl, ethyl, isopropyl, tert-butyl, benzyl-, and tosyloxy-.

In some embodiments of this aspect of the disclosure the detectable label can be a dye, fluorescent label, a radiolabel or a quencher.

In some embodiments of this aspect of the disclosure the detectable label can be attached to the probe by an —O—, a —N—, or an —S— link.

In some embodiments of this aspect of the disclosure the detectable label is (2-oxo-2H-chromen-7-yl) (III) or (4S)-2-(6-oxo-1,3-benzothiazol-2-yl)-4,5-dihydrothiazole-4-carboxylic acid (IV) and can have the structures:

III
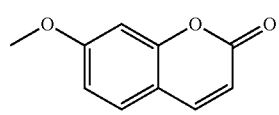

or

IV
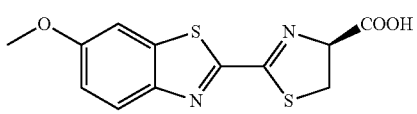

In some embodiments the probe can be selected from the group consisting of:

(s)-CC-1
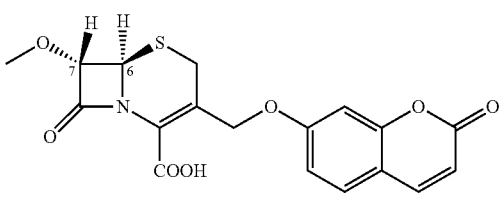

(s)-CC-2
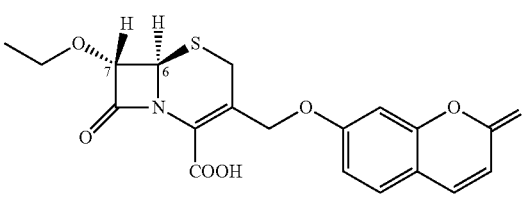

(s)-CC-3
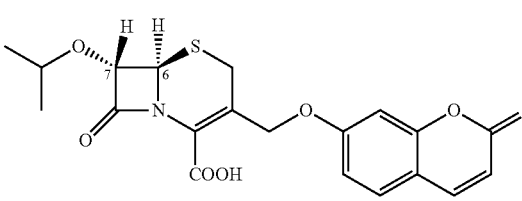

(s)-CC-4
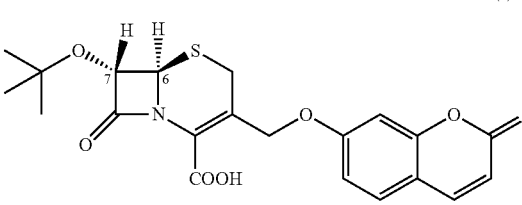

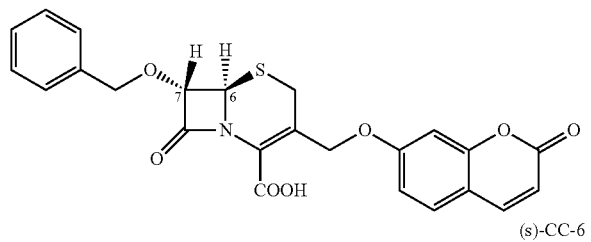
(s)-CC-5

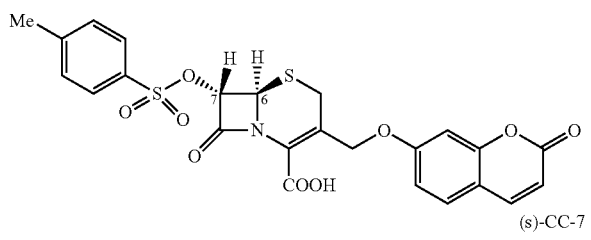
(s)-CC-6

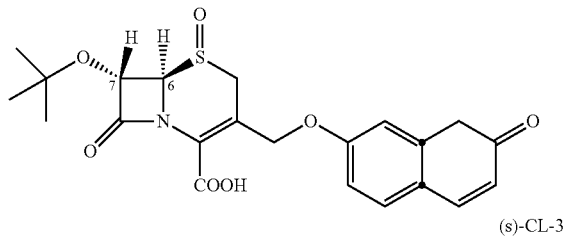
(s)-CC-7

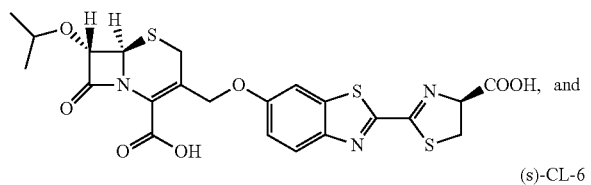
(s)-CL-3

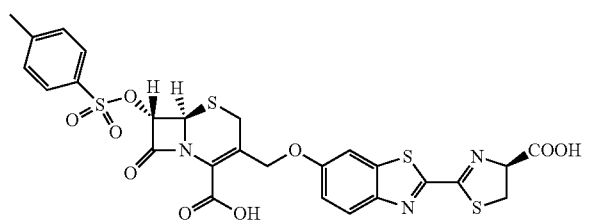
(s)-CL-6

In some embodiments of this aspect of the disclosure the sample can be a bacterial culture.

In some embodiments of this aspect of the disclosure the sample can be isolated from an animal or human subject.

In some embodiments of this aspect of the disclosure the sample can be a bacterial culture generated from a sample from a human or animal subject.

In some embodiments of this aspect of the disclosure the sample can comprise at least one of a *Klebsiella* sp. or an *Escherichia* sp.

In some embodiments of this aspect of the disclosure the detectable label can be a luciferase substrate and said method can further comprise contacting the reaction mix with a luciferase thereby generating a detectable bioluminescent signal in the presence of released luciferase substrate.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure. The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

Example 1

Cloning of Carbapenemases and Non-Carbapenemase Lactamases

Primers used for cloning of full-length β-lactamases into pBAD/Myc-His vector (Invitrogen), as shown in Table 2.

TABLE 2

Primers for cloning of β-lactamases

| Primer | Sequences |
|---|---|
| NDM-1 F | atttccatggaattgcccaatattatgcaccc (SEQ ID NO: 7) |
| NDM-1 R | aaaagcttgtcgacgcgcagcttgtcggccat (SEQ ID NO: 8) |
| KPC-3 F | atttccatggaatcactgtatcgccgtctagttc (SEQ ID NO: 9) |
| KPC-3 R | aaaagcttgtcgacctgcccgttgacgcccaatc (SEQ ID NO: 10) |
| VIM-27 F | atttccatgggattaaaagttattagtagtttattggtc tacatgaccg (SEQ ID NO: 11) |
| VIM-27 R | aaaagcttgtcgacctcggcgactgagcgattttttgtg (SEQ ID NO: 12) |

TABLE 2-continued

Primers for cloning of β-lactamases

| Primer | Sequences |
|---|---|
| IMP-1 F | atttccatgggaagcaagttatctgtattcttttatattt ttgttttgtagc (SEQ ID NO: 13) |
| IMP-1 R | aaaagcttgtcgacgttgcttggttttgatggttttta ctttc (SEQ ID NO: 14) |
| OXA-48 F | atttccatgggacgtgtattagccttatcggctgtg (SEQ ID NO: 15) |
| OXA-48 R | aaaagcttgtcgacgggaataatttttcctgtttgagc acttc (SEQ ID NO: 16) |
| TEM-1 F | atttccatgggccatcatcatcatcatagtattcaa catttccgtgtcgcccttatt (SEQ ID NO: 17) |
| TEM-1 R | aaaagcttgtcgacttaccaatgcttaatcagtgaggc (SEQ ID NO: 18) |

Genomic or plasmid DNAs were purified from each bacterial strain (*Klebsiella pneumonia* or *Escherichia coli*) over-expressing a specific enzyme as a template for PCR. PCR was carried out using Pfx50 DNA polymerase and the manufacturer's protocol (Invitrogen) with F (Forward), R (Reverse) primers and template DNA (the sequences of which are shown in FIG. 16 and Table 2) for each enzyme. Purified PCR products were digested with NcoI and SalI restriction enzymes and cloned into the pBAD/Myc-His vector using T4 DNA ligase (Invitrogen). The ligated plasmid DNA was transformed into bacterial BL21 or Top10 cells. Inserted DNA sequences were confirmed by sequencing analysis.

Example 2

Purification of the Enzymes from Bacterial Cells

Figure 15:
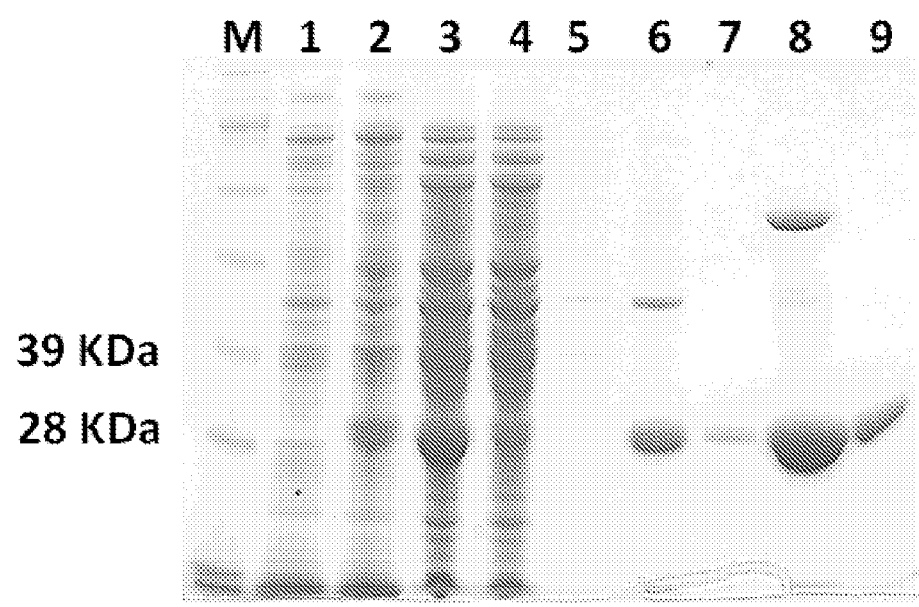
FIG. 15 is a digital image illustrating a typical SDS-PAGE analysis showing the purity of a preparation of an expressed recombinant enzyme. Purified VIM-27 (29.1 KDa) is shown as the representative example. Molecular weights of other enzymes are also about 30 KDa (BlaC, 29.5 KDa; TEM-1, 32.4 KDa; NDM-1, 29.5 KDa; KPC-3, 32.3 KDa; IMP-1, 28.2 KDa), and they showed comparable purities and yields, to that with VIM-27. M, protein standard; 1, lysate before induction; 2, lysate after induction; 3, soluble fraction after cell lysis; 4, flow-through after Ni-NTA binding; 5, washing 1; 6, washing 2; 7, washing 5; 8, eluted by 250 mM imidazole in PBS; 9, purified enzyme by PD-10 column.
Figure 17:
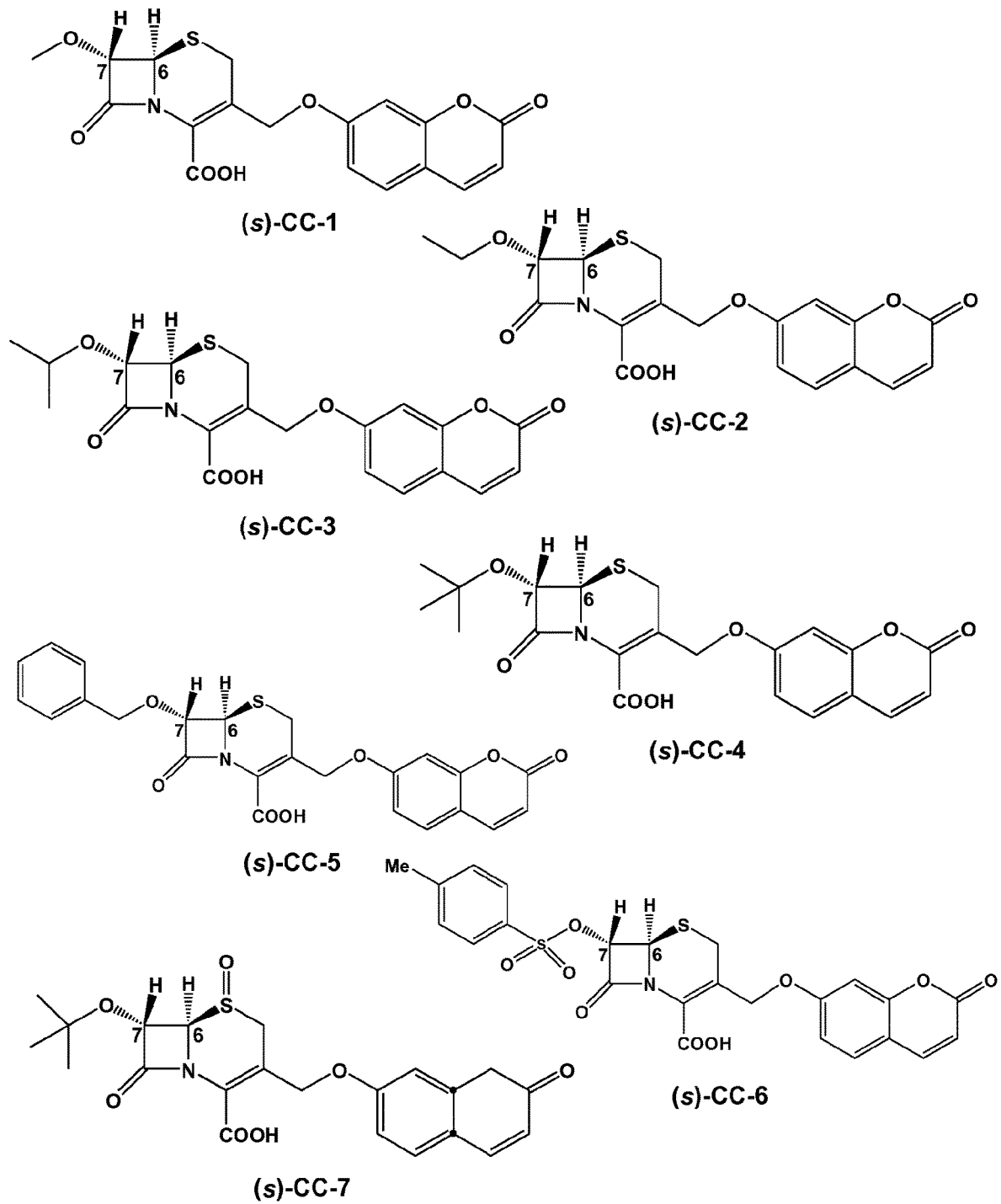
FIG. 17 illustrates the formulas of the probes (s)-CC-1, (s)-CC-2, (s)-CC-3, (s)-CC-4, (s)-CC-5, (s)-CC-6, and (s)-CC-7.
Figure 18:
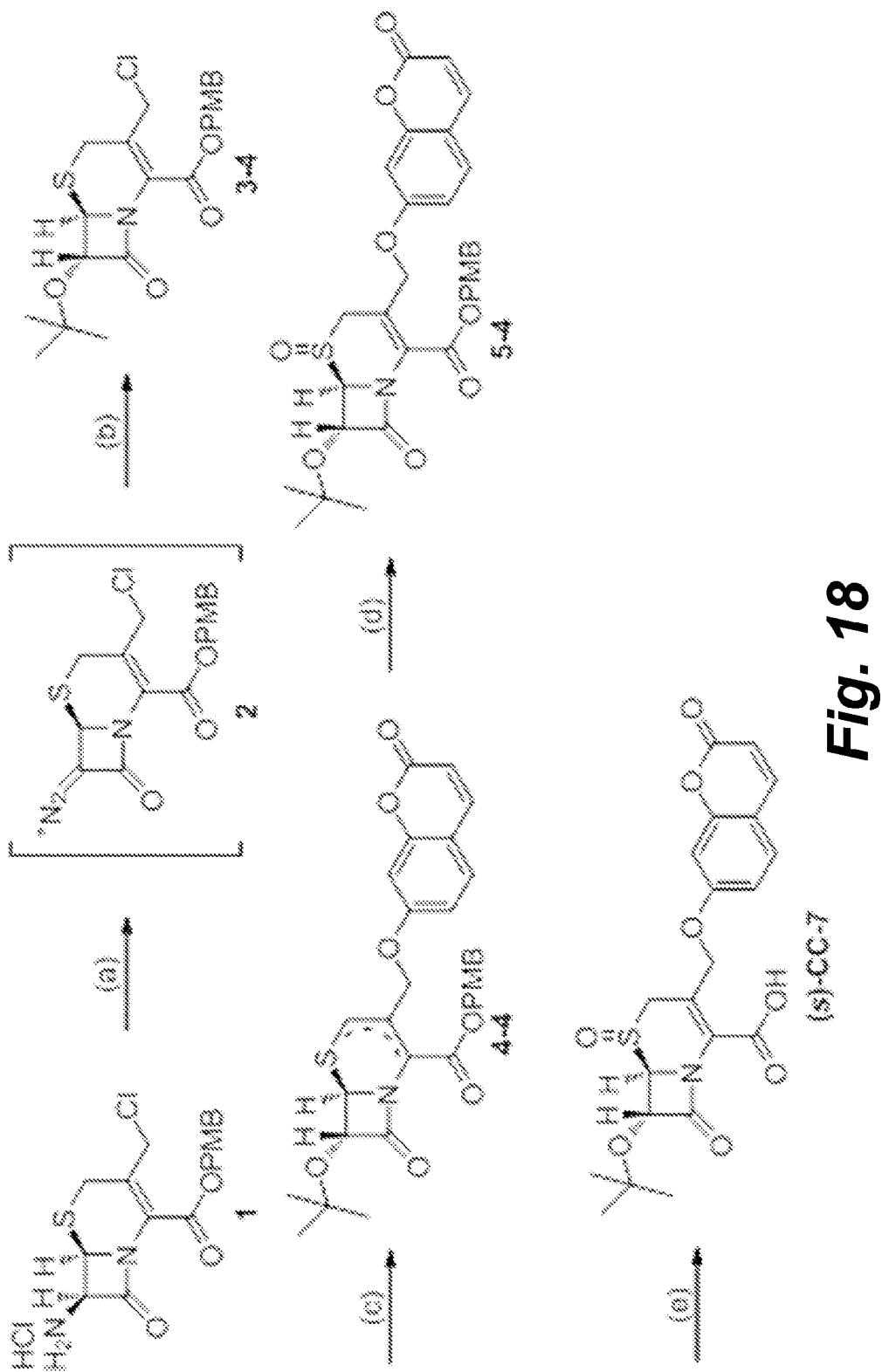
FIG. 18 illustrates the scheme for the synthesis of the fluorogenic probe (s)-CC-7 targeting carbapenemases. (a) NaNO$_2$, 2N H$_2$SO$_4$, DCM, 0° C., 1 h. (b) t-BuOH, p-TsOH, DCM, 0° C. to r.t, overnight. (c) (i): NaI, acetone, r.t, 1 h; (ii). 7-hydroxycoumarin, K$_2$CO$_3$, CH$_3$CN, r.t, 2.5 h. (d) 1.0 eqv m-CPBA, DCM, 0° C., 0.5 h. (e) DCM:TFA:TIPS: H$_2$O=65:30:2.5:2.5, 30 min, 0° C.
Figure 19A:
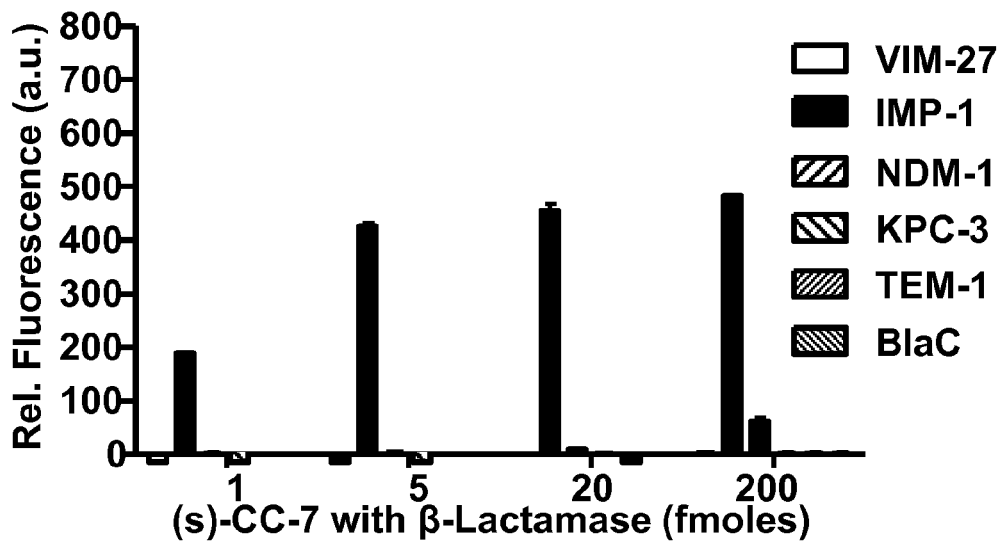
FIGS. 19A and 19B are graphs that illustrate the recombinant β-lactamases selectivity and CRE specificity of probe (s)-CC-7. The relative fluorescence of indicated amounts of β-lactamases (FIG. 19A) and β-lactamase-expressing bacteria (FIG. 19B) after incubation with probes (10 μM) at room temperature in 25 μL of 1×PBS buffer (pH=7.4) for 2 h.
Figure 19B:
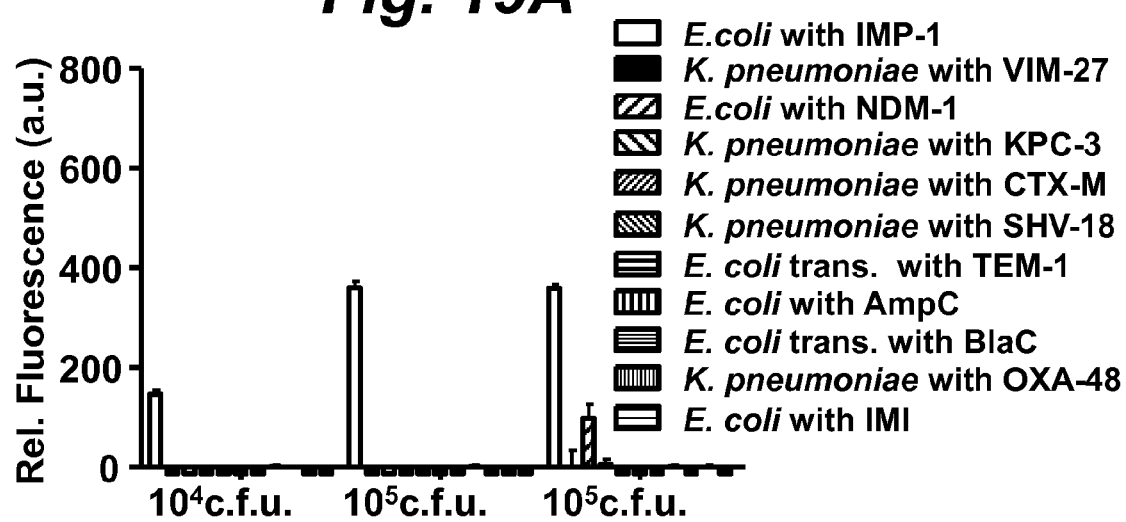
Figure 20:
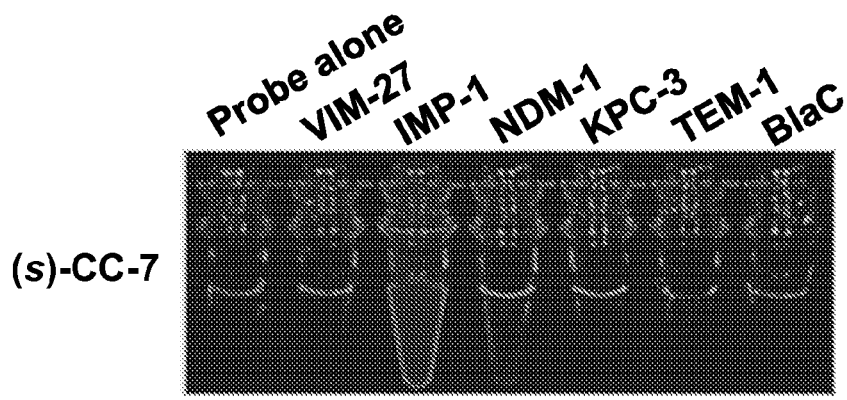
FIG. 20 is a digital image of recombinant β-lactamases (4 nM) with (s)-CC-7 (10 μM) in 1×PBS (pH=7.4) with 2 h incubation at room temperature. Image was generated with excitation of UV light (360 nm).
Figure 21A:
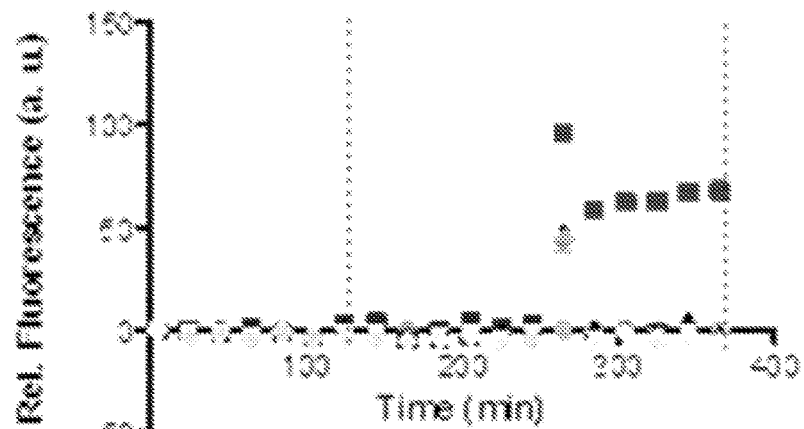
FIGS. 21A-21F are graphs illustrating the time-courses of fluorescent activation of indicated probes with VIM-27, IMP-1, NDM-1, KPC-3, TEM-1 and BlaC. Error bars are SD.
Figure 21B:
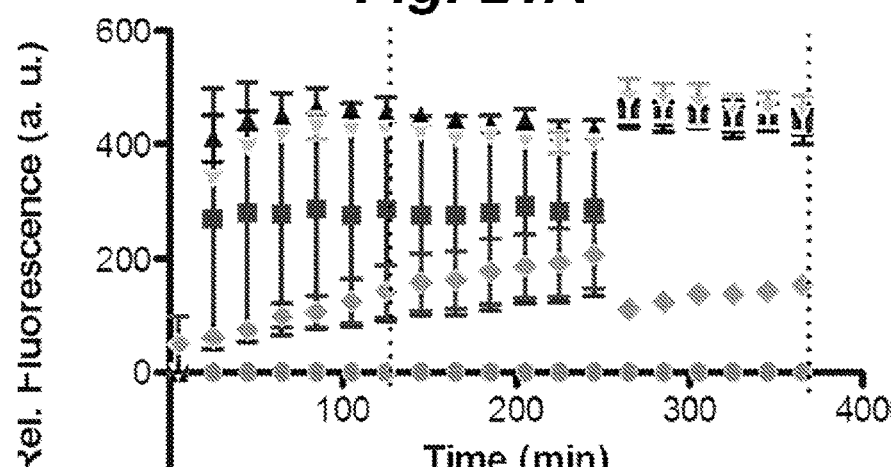
Figure 21C:
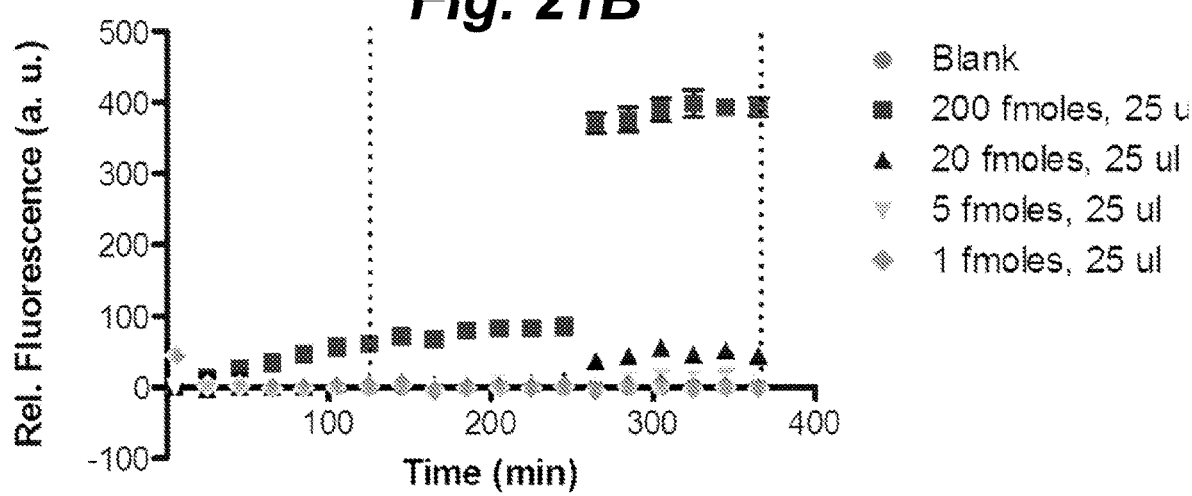
Figure 21D:
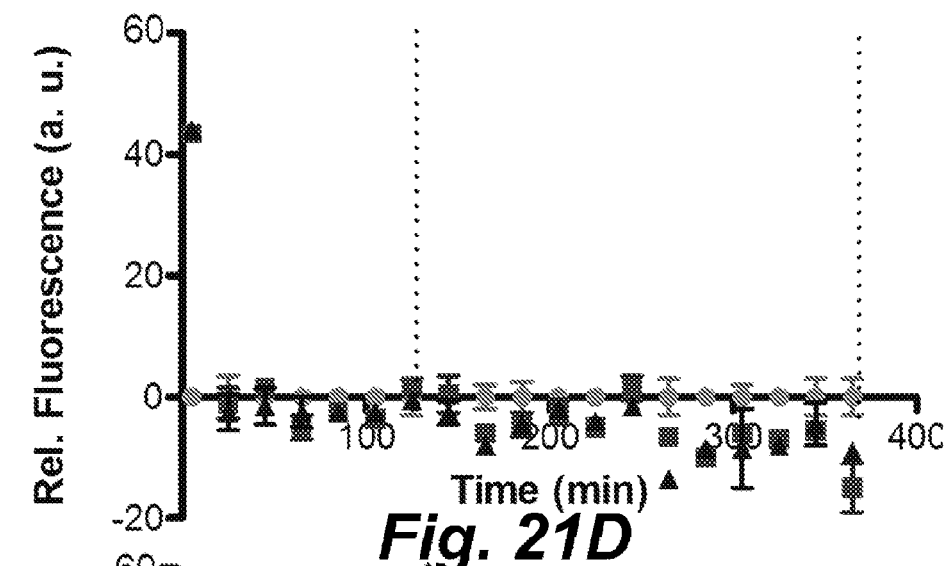
Figure 21E:
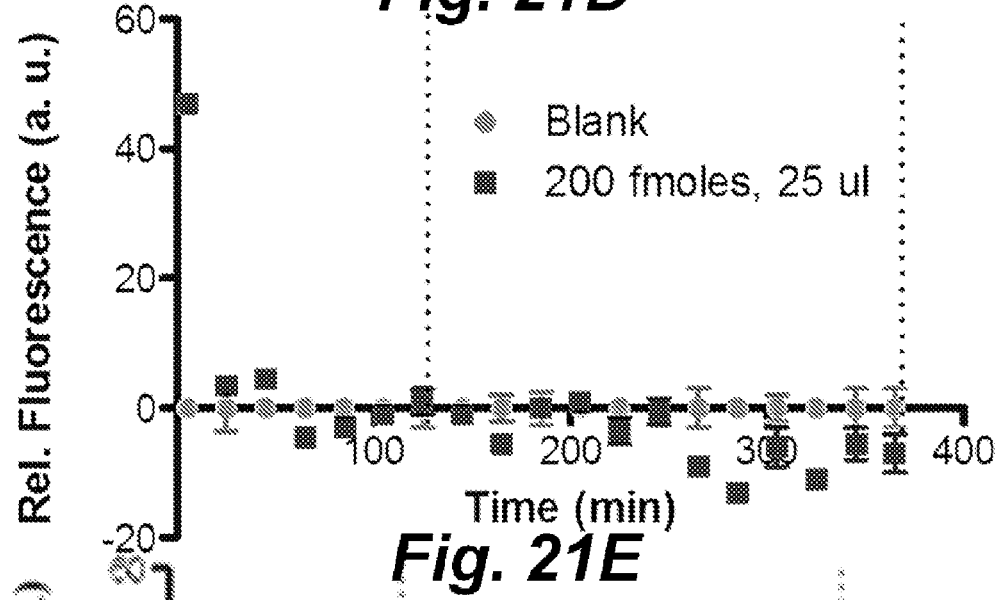
Figure 21F:
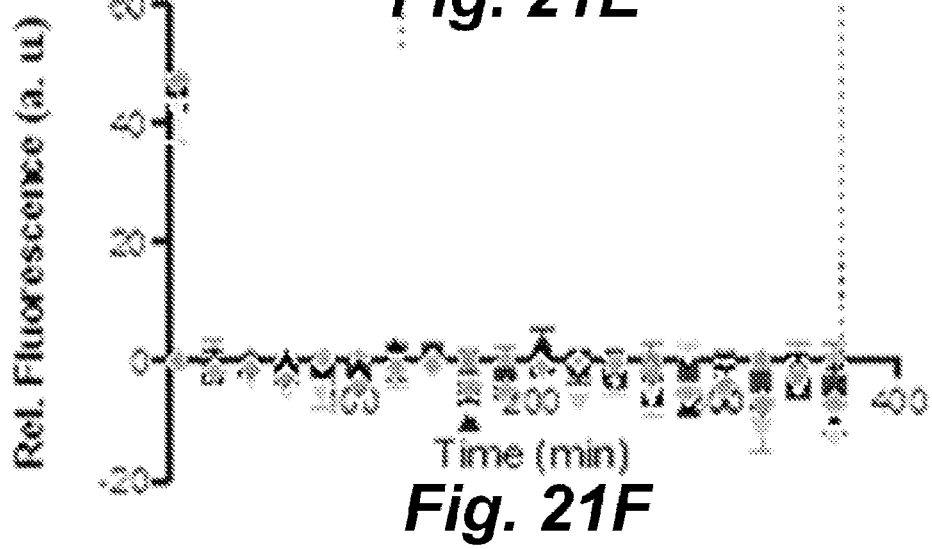
Figure 22:
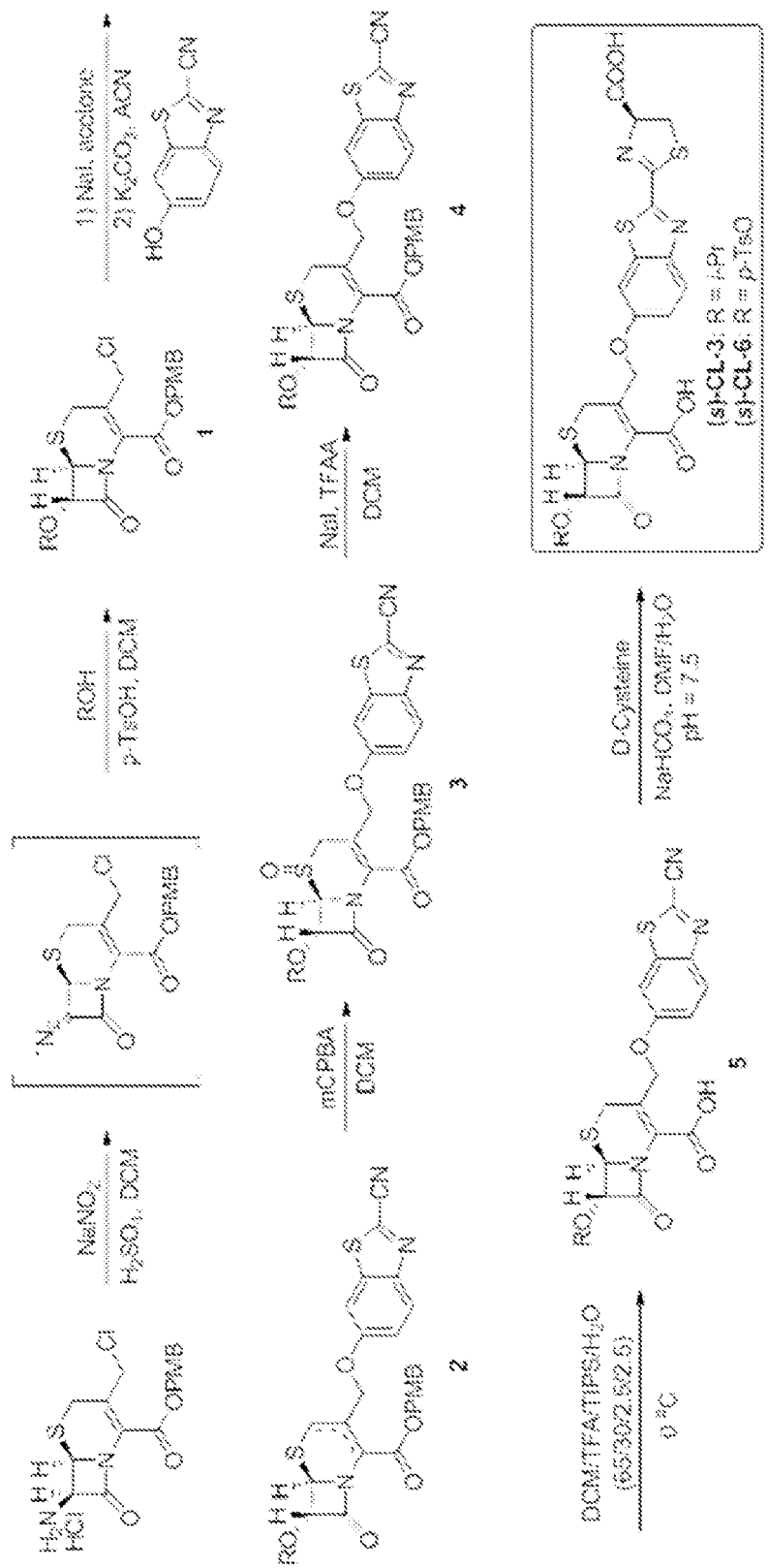
FIG. 22 illustrates a scheme for the synthesis of the bioluminogenic probes (s)-CL-3 and (s)-CL-6 targeting carbapenemases.
Figure 23:
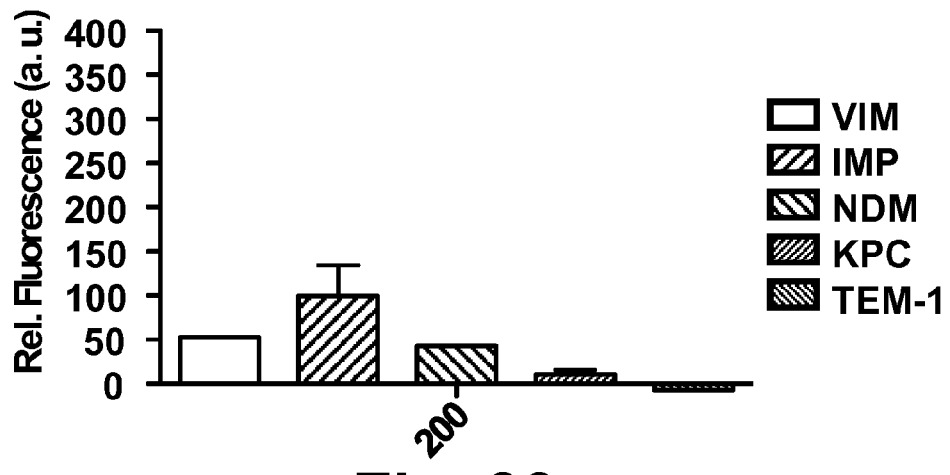
FIG. 23 is a graph illustrating β-Lactamase selectivity of probe (s)-CL-3. Relative fluorescence of indicated amounts of β-lactamases after incubated with probes (1 μM) at room temperature in 25 μL of 1×PBS buffer (pH=7.4) for 2 h. Relative fluorescence represents the difference in the fluorescence intensity with and without β-lactamase incubation. Fluorescence was measured with excitation at 350 nm (band width 5 nm) and emission at 550 nm (band width 7.5 nm). Error bars are ±SD.
Figure 24:
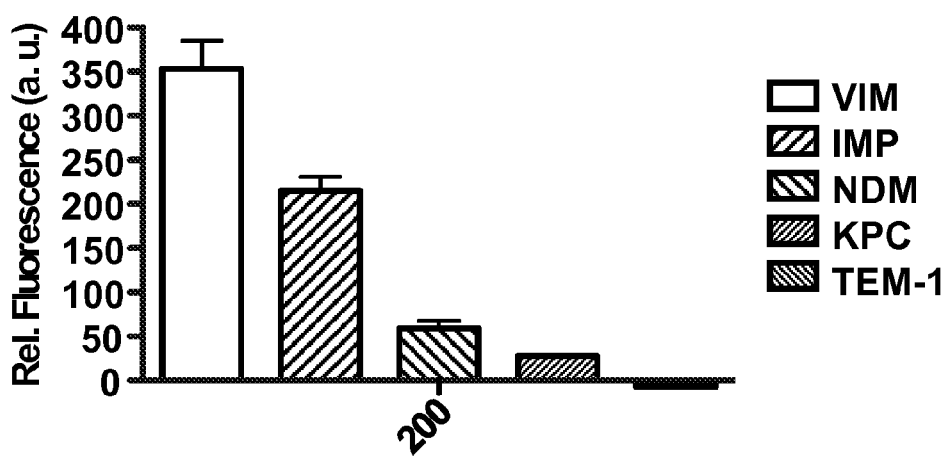
FIG. 24 is a graph illustrating β-Lactamase selectivity of probe (s)-CL-6. Relative fluorescence of indicated amounts of β-lactamases after incubated with probes (1 μM) at room temperature in 25 μL of 1×PBS buffer (pH=7.4) for 2 h. Relative fluorescence represents the difference in the fluorescence intensity with and without β-lactamase incubation. Fluorescence was measured with excitation at 350 nm (band width 5 nm) and emission at 550 nm (band width 7.5 nm). Error bars are ±SD.
Figure 25:
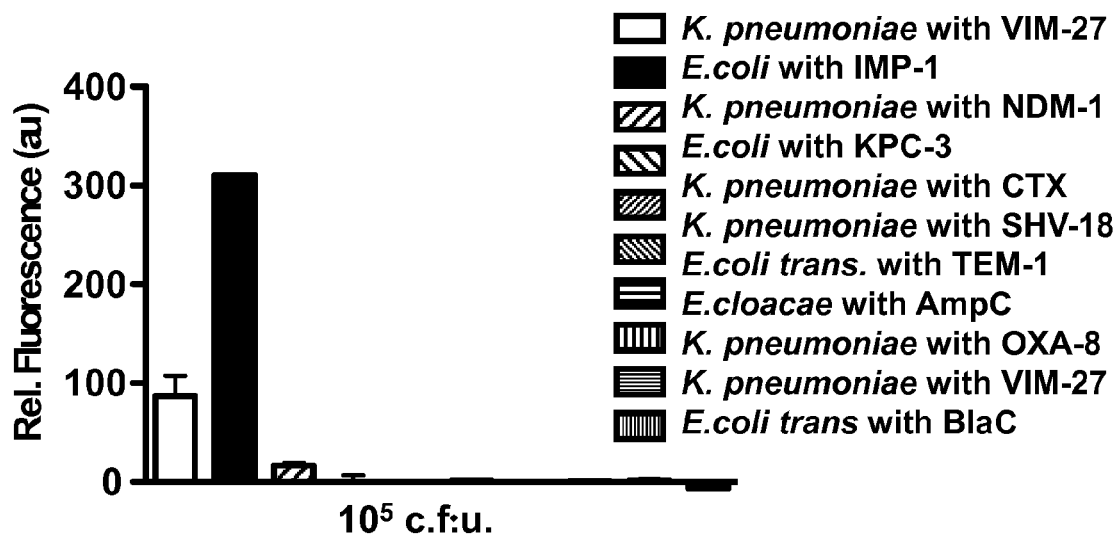
FIG. 25 is a graph illustrating the relative fluorescence of 3-lactamase-expressing bacteria lysates after incubation with the probe (s)-CL-3 (1 μM) at room temperature in 1×PBS buffer (pH=7.4) for 2 h. All bacteria numbers are as indicated except for E. coli expressing AmpC which was at 10$^7$ c.f.u. Relative fluorescence represents the difference in fluorescence intensity with and without β-lactamase incubation. Fluorescence was measured with excitation at 350 nm (band width 5 nm) and emission at 550 nm (band width 7.5 nm). Error bars are ±SD.
Figure 26:
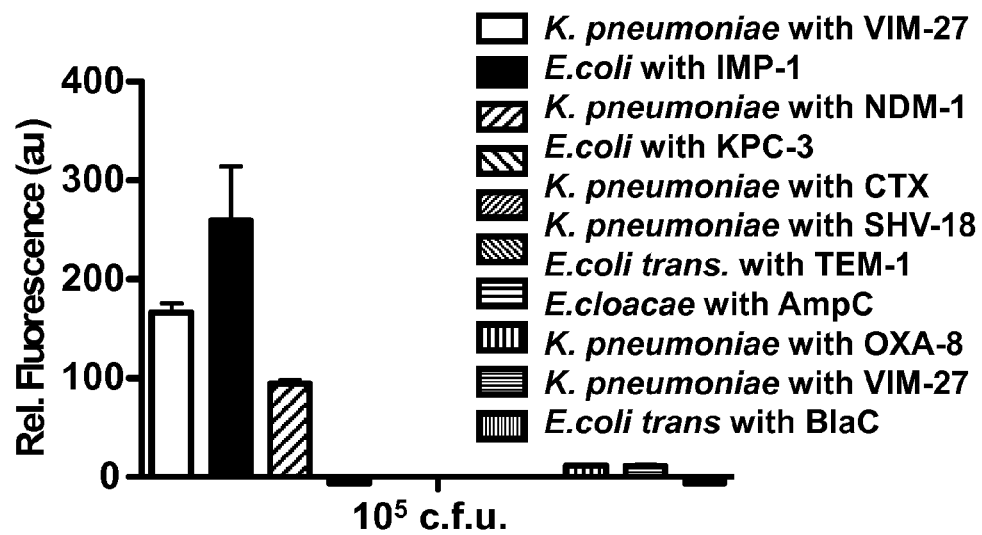
FIG. 26 is a graph illustrating the relative fluorescence of 3-lactamase-expressing bacteria lysates after incubation with the probe (s)-CL-6 (1 μM) at room temperature in 1×PBS buffer (pH=7.4) for 2 h. All bacteria numbers are as indicated except for E. coli expressing AmpC which was at 10$^7$ c.f.u. Relative fluorescence represents the difference in fluorescence intensity with and without β-lactamase incubation. Fluorescence was measured with excitation at 350 nm (band width 5 nm) and emission at 550 nm (band width 7.5 nm). Error bars are ±SD.
Figure 27:
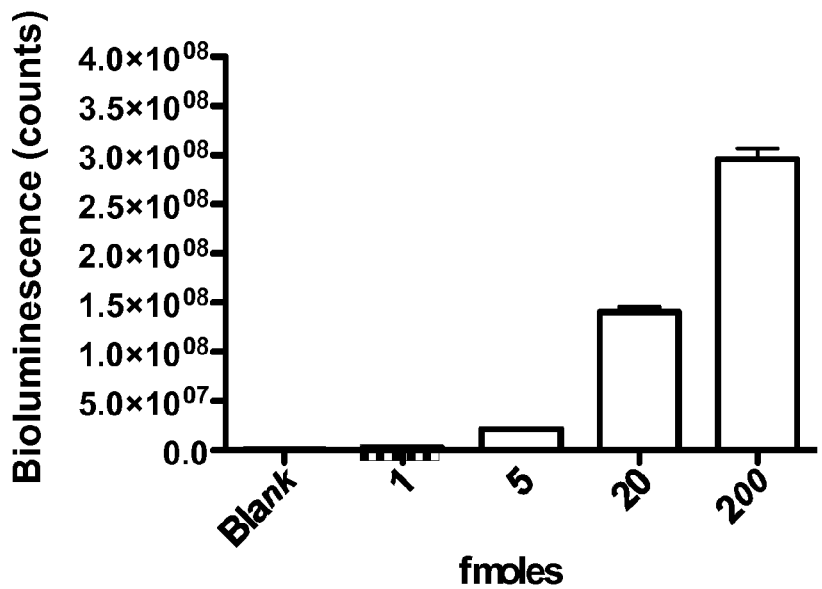
FIG. 27 is a graph illustrating the dependence of bioluminescence emission on different amounts of purified NDM-1+fLuc. (s)-CL-6] at 1 μM.
Figure 28:
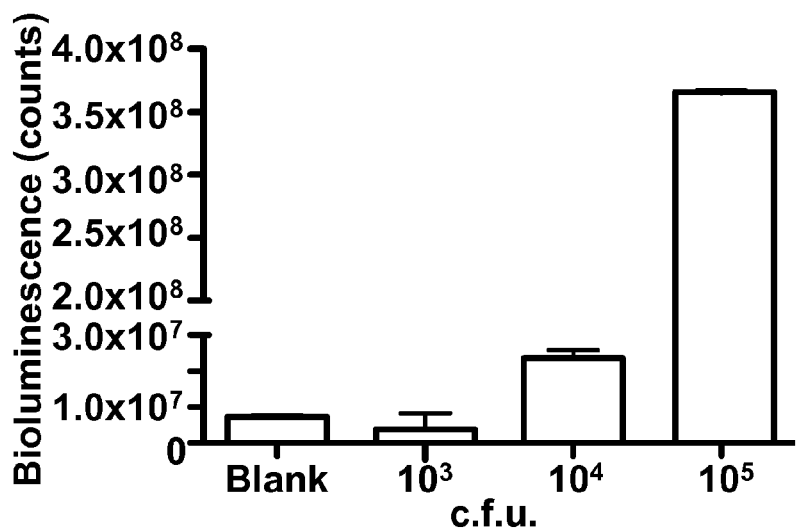
FIG. 28 is a graph illustrating dependence of bioluminescence emission on different concentrations of NDM-1 lysates+fLuc. [(s)-CL-6] at 1 μM.
Figure 29:
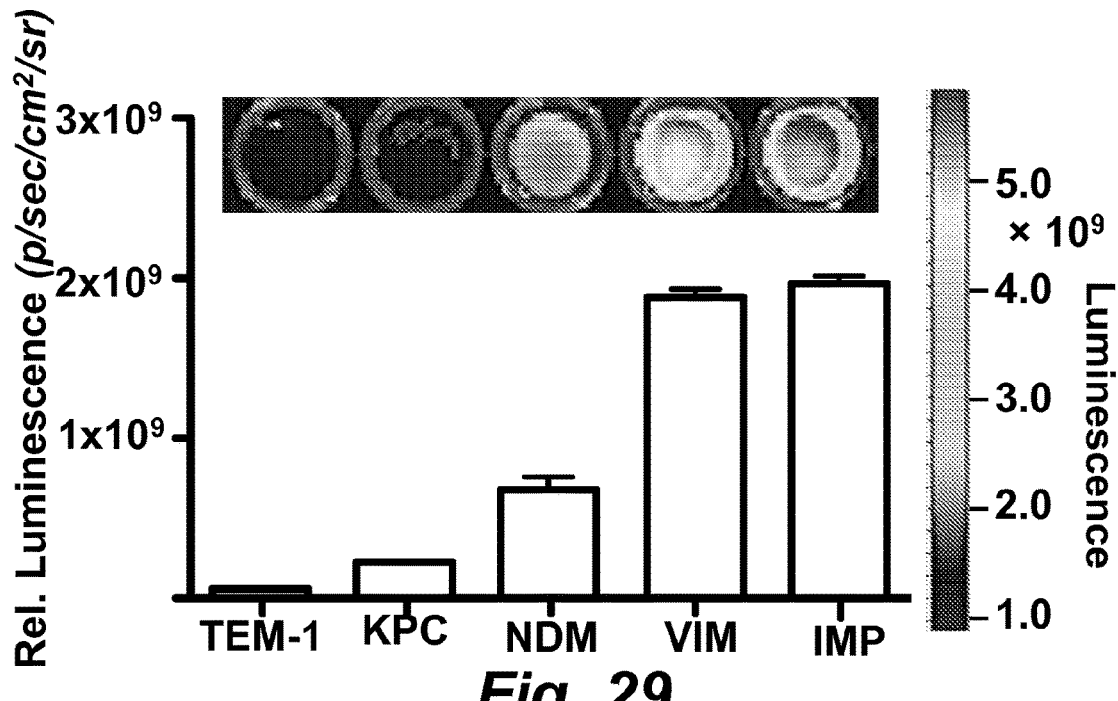
FIG. 29 illustrates β-lactamase selectivity of (s)-CL-6. Relative luminescence of 400 fmoles β-lactamases after incubated with probe (1 μM) at room temperature in 100 μL of 1×PBS buffer (pH=7.4) for 2 h followed by addition of 50 ng fLuc. Relative luminescence represents the difference in the luminescence intensity with and without β-lactamase incubation. Luminescence was measured with IVIS 200. Error bars are ±SD.

All enzymes were purified as described in Doherty et al., (1990) *J. Med. Chem.* 33: 2513-2521, incorporated herein by reference in its entirety. In brief, 6×His-containing β-lactamase (pBAD/Myc-His vector in BL21 or Top10 bacteria) was over-expressed by 0.2% arabinose induction for more than 6 h at 30° C. until the optical density at 600 nm ($OD_{600}$) reached to 0.8. Proteins were then purified using BUG-BUSTER® protein extraction reagent (Novagen) and Ni-NTA agarose bead (Qiagen) with manufacturer's protocols (Wash buffer 1: 0.01 M PBS, 150 mM NaCl at pH 7.4; wash buffer 2 for 3-times washing: 20 mM imidazole in 0.01 M PBS at pH 7.4; elution buffer, 250 mM imidazole in 0.01 M PBS at pH 7.4). After purification, eluted protein was purified using a PD-10 column (GE healthcare). Purity was determined by 12% sodium dodecyl sulfate-polyacrylamide gel electrophoresis (SDS-PAGE, as shown in FIG. 15) and then the concentration was determined by Bradford assay kit (BioRad).

Example 3

Experimental Section

All chemicals were purchased from commercial sources (e.g. Aldrich, Alfa Aesar and TCI America) and used without further purification. Analytical TLC was performed with 0.25 mm silica gel 60F plates with fluorescent indicator (254 nm). Plates were visualized by ultraviolet light. HPLC was performed on a Dionex HPLC System (Dionex Corporation) equipped with a GP50 gradient pump and an inline diode array UV-Vis detector. A reversed-phase C18 (Phenomenax, 5 µm, 4.6×250 mm or Dionex, 5 µm, 21.2×250 mm) column was used with a MeCN/$H_2O$ gradient mobile phase containing 0.1% trifluoroacetic acid at a flow of 1 or 12 mL/min for the analysis or purification. The $^1H$ and $^{13}C$ NMR spectra were taken on Varian 400 MHz magnetic resonance spectrometer. Data for $^1H$ NMR spectra are reported as follows: chemical shifts are reported as δ in units of parts per million (ppm) relative to chloroform-d (δ 7.26, s); multiplicities are reported as follows: s (singlet), d (doublet), t (triplet), q (quartet), dd (doublet of doublets), m (multiplet), or br (broadened); coupling constants are reported as a J value in Hertz (Hz); the number of protons (n) for a given resonance is indicated nH, and based on the spectral integration values. Kinetic experiments were conducted in a M1000 microplate reader (TECAN, research triangle park, NC).

Example 4

Preparation of 4-methoxybenzyl 3-(chloromethyl)-7-diazo-8-oxo-5-thia-1-azabicyclo[4.2.0]oct-2-ene-2-carboxylate Compound 2

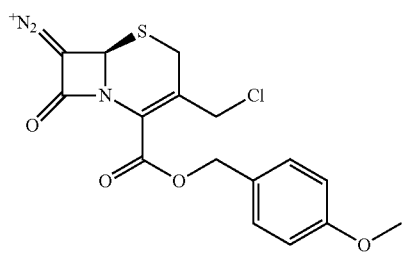

Compound 2 was prepared according to previous published procedures (Doherty et al., (1990) *J. Med. Chem.* 33: 2513-2521, incorporated herein by reference in its entirety). To a solution of ACLE (2.0 g, 5 mmol) in 20 mL $CH_2Cl_2$ was added a mixture of $NaNO_2$ (0.35 g, 5 mmol) in water (20 mL). The resulting two-phase mixture was cooled to 0° C., 2N aqueous $H_2SO_4$ (3.8 mL) was then added dropwise over 30 min with vigorous stirring. The reaction was continually stirred for 1 h at 0° C. Subsequently, the organic layers were separated, and the aqueous layer was washed with $CH_2Cl_2$ for two times. The organic layers were combined, washed with brine, dried over $MgSO_4$, and filtered to give a yellow solution of 2. This solution was used immediately in the next step.

Example 5

Preparation of (6R,7S)-4-methoxybenzyl 3-(chloromethyl)-7-alkoxy-8-oxo-5-thia-1-azabicyclo[4.2.0]oct-2-ene-2-carboxylate (3)

To a solution of compound 2 in $CH_2Cl_2$ was added various alcohols (about 10 to about 100 eqv) at 0° C. Tosic acid (1 eqv) was subsequently added in portion over 20 min with stirring (gas evolution). The ice bath was then removed and the reaction was continually stirred overnight at room temperature. The reactions were monitored by TLC. After the completion of reactions, the reaction mixture was concentrated and diluted with ethyl acetate, and subsequently extracted with aqueous saturated NaHCO₃, water and brine. The organic layers were dried over anhydrous MgSO₄ and concentrated in vacuo. The residue was finally chromatographed on a flash column with hexane/EtOAc (4:1) to give the desired compound 3. Examples of the compound 3 synthesized by using the alcohols methanol, ethanol, isopropanol, tert-butanol, benzyl alcohol, and tosyl acid are the compounds 3-1 to 3-6, respectively:

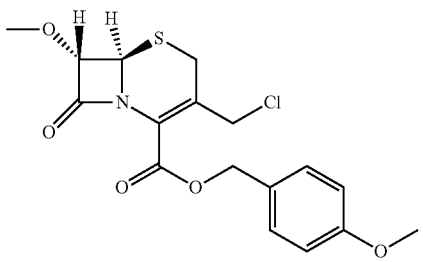

(6R,7S)-4-methoxybenzyl 3-(chloromethyl)-7-methoxy-8-oxo-5-thia-1-azabicyclo[4.2.0]oct-2-ene-2-carboxylate (3-1)

Yield=38%. ¹H NMR (400 MHz, CDCl₃) δ 7.37 (d, J=8.6 Hz, 2H), 6.89 (d, J=8.7 Hz, 2H), 5.30 (d, J=11.8 Hz, 1H), 5.22 (d, J=11.8 Hz, 1H), 4.69 (d, J=1.6 Hz, 1H), 4.52 (d, J=1.8 Hz, 1H), 4.42 (d, J=11.9 Hz, 1H), 4.31 (d, J=11.7 Hz, 1H), 3.81 (s, 3H), 3.65 (d, J=18.1 Hz, 1H), 3.56-3.49 (m, 3H), 3.40 (d, J=18.1 Hz, 1H). ¹³C NMR (101 MHz, CDCl₃) δ 161.32, 161.25, 160.15, 130.96, 127.09, 126.92, 122.48, 114.20, 90.18, 68.52, 58.50, 56.41, 55.52, 43.62, 28.69.

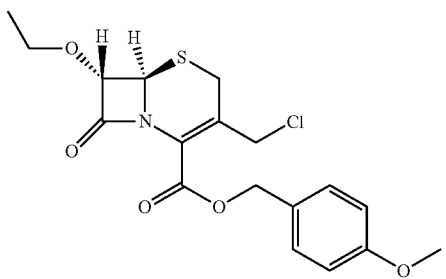

(6R,7S)-4-methoxybenzyl 3-(chloromethyl)-7-ethoxy-8-oxo-5-thia-1-azabicyclo[4.2.0]oct-2-ene-2-carboxylate (3-2)

Yield=20%. ¹H NMR (400 MHz, CDCl₃) δ 7.37 (d, J=8.4 Hz, 2H), 6.89 (d, J=8.6 Hz, 2H), 5.30 (d, J=11.8 Hz, 1H), 5.21 (d, J=11.8 Hz, 1H), 4.67 (d, J=1.8 Hz, 1H), 4.55 (dd, J=1.8, 0.4 Hz, 1H), 4.41 (d, J=11.8 Hz, 1H), 4.31 (d, J=11.8 Hz, 1H), 3.81 (s, 3H), 3.77-3.68 (m, 2H), 3.64 (d, J=18.0 Hz, 1H), 3.40 (d, J=18.0 Hz, 1H), 1.29-1.23 (m, 4H). ¹³C NMR (101 MHz, CDCl₃) δ 161.56, 161.35, 160.14, 130.98, 127.17, 126.95, 122.31, 114.19, 89.02, 68.51, 67.27, 57.12, 55.52, 43.65, 28.71, 15.34.

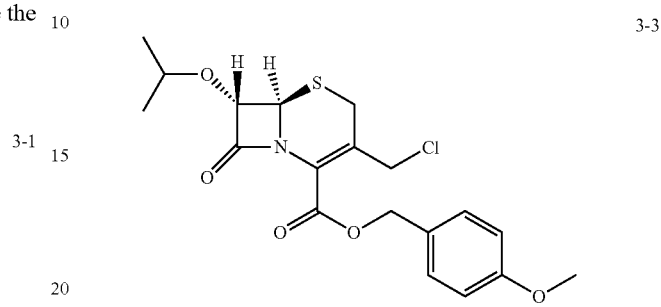

(6R,7S)-4-methoxybenzyl 3-(chloromethyl)-7-isopropoxy-8-oxo-5-thia-1-azabicyclo[4.2.0]oct-2-ene-2-carboxylate (3-3)

Yield=23%. ¹H NMR (400 MHz, CDCl₃) δ 7.34 (d, J=8.6 Hz, 2H), 6.87 (d, J=8.6 Hz, 2H), 5.26 (d, J=5.6 Hz, 1H), 5.20 (d, J=4.4 Hz, 1H), 4.73 (d, J=1.7 Hz, 1H), 4.68 (d, J=1.8 Hz, 1H), 4.40 (d, J=11.8 Hz, 1H), 4.33 (d, J=11.8 Hz, 1H), 3.77 (s, 3H), 3.60 (d, J=18.1 Hz, 1H), 3.42 (d, J=22.2 Hz, 1H), 1.21 (dd, J=17.6, 6.1 Hz, 6H). ¹³C NMR (101 MHz, CDCl₃) δ 167.94, 160.92, 158.69, 130.95, 130.90, 126.84, 124.72, 122.25, 114.23, 114.19, 87.81, 74.69, 68.55, 61.17, 59.24, 55.51, 43.29, 28.67, 22.58.

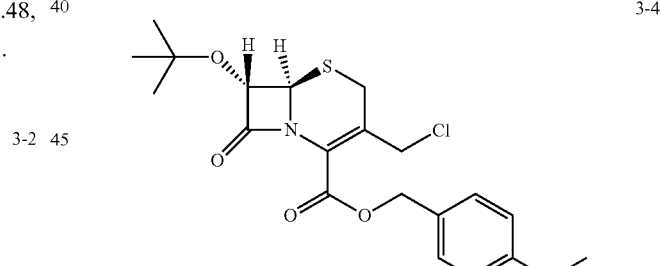

(6R,7S)-4-methoxybenzyl 7-(tert-butoxy)-3-(chloromethyl)-8-oxo-5-thia-1-azabicyclo[4.2.0]oct-2-ene-2-carboxylate (3-4)

Yield=33%. ¹H NMR (400 MHz, CDCl₃) δ 7.36 (d, J=2.1 Hz, 2H), 6.89 (d, J=3.9 Hz, 2H), 5.30 (d, J=11.8 Hz, 1H), 5.20 (d, J=11.8 Hz, 1H), 4.74 (d, J=1.9 Hz, 1H), 4.68 (d, J=1.9 Hz, 1H), 4.42 (d, J=11.8 Hz, 1H), 4.33 (d, J=18.2 Hz, 1H), 3.78 (s, 3H), 3.61 (d, J=18.1 Hz, 1H), 3.42 (d, J=23.2 Hz, 1H), 1.25 (s, 9H). ¹³C NMR (101 MHz, CDCl₃) δ 168.01, 162.66, 158.68, 130.97, 130.91, 126.84, 124.70, 122.02, 114.24, 83.09, 76.69, 68.57, 61.19, 55.52, 43.30, 28.70, 28.10.

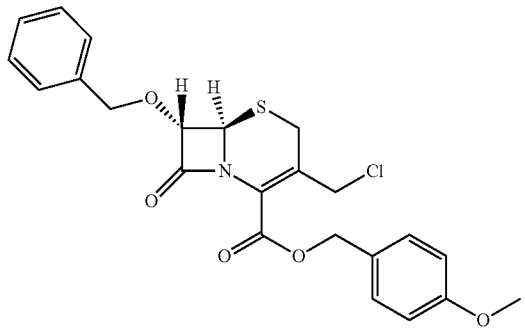

(6R,7S)-4-methoxybenzyl 7-(benzyloxy)-3-(chloromethyl)-8-oxo-5-thia-1-azabicyclo[4.2.0]oct-2-ene-2-carboxylate (3-5)

Yield=18%. $^1$H NMR (400 MHz, CDCl$_3$) δ 7.82 (d, J=8.4 Hz, 2H), 7.41-7.31 (m, 5H), 6.88 (d, J=8.8 Hz, 2H), 5.22 (dd, J=34.3, 11.8 Hz, 2H), 5.11 (d, J=1.8 Hz, 1H), 4.74 (d, J=1.8 Hz, 1H), 4.67 (s, 1H), 4.36 (dd, J=27.1, 11.9 Hz, 2H), 3.79 (s, 3H), 3.59 (d, J=18.1 Hz, 1H), 3.38 (d, J=18.1 Hz, 1H). $^{13}$C NMR (101 MHz, CDCl$_3$) δ 160.85, 160.19, 156.85, 146.53, 131.82, 131.00, 130.54, 128.76, 128.55, 127.80, 127.20, 126.73, 126.67, 125.12, 114.25, 83.70, 68.63, 65.45, 57.31, 55.53, 28.52, 22.04.

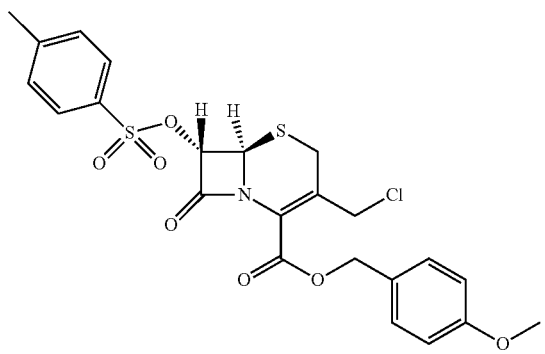

(6R,7S)-4-methoxybenzyl3-(chloromethyl)-8-oxo-7-(tosyloxy)-5-thia-1-azabicyclo[4.2.0]oct-2-ene-2-carboxylate (3-6)

Yield=20%. $^1$H NMR (400 MHz, CDCl$_3$) δ 7.83 (d, J=8.2 Hz, 1H), 7.36 (dd, J=22.4, 8.3 Hz, 3H), 7.02 (d, J=8.1 Hz, 1H), 6.89 (d, J=8.6 Hz, 2H), 6.74 (d, J=8.4 Hz, 1H), 5.23 (dd, J=35.8, 11.7 Hz, 2H), 5.11 (dd, J=1.8, 1.2 Hz, 1H), 4.79-4.73 (m, 1H), 4.37 (dd, J=34.3, 11.9 Hz, 2H), 3.81 (s, 3H), 3.61 (d, J=18.1 Hz, 1H), 3.40 (d, J=18.1 Hz, 1H), 2.47 (s, 3H). $^{13}$C NMR (101 MHz, CDCl$_3$) δ 171.44, 160.84, 160.16, 156.87, 146.56, 131.78, 130.97, 130.56, 128.81, 128.50, 126.66, 125.21, 114.14, 83.68, 68.58, 64.97, 57.25, 55.49, 43.19, 28.46, 22.01.

Example 6

Preparation of (6R,7S)-4-methoxybenzyl 7-alkoxy-8-oxo-3-(((2-oxo-2H-chromen-7-yl)oxy)methyl)-5-thia-1-azabicyclo[4.2.0]oct-2-ene-2-carboxylate (6)

Compound 6 was synthesized according to Bradley et al., (1999) *Int. J. Antimicrob. Agents* 11: 93-100 and Papp-Wallace et al., (2011) *Antimicrob. Agents Chemother.* 55: 4943-4960, incorporated herein by reference in their entireties. To a solution of 3 (1.0 eqv) in acetone was added sodium iodide (1.0 eqv). The resulting mixture was stirred at room temperature for one hour and then the solvent was removed under reduced pressure. Water was added and extracted with ethyl acetate for three times. The combined organic layers were then washed with Na$_2$S$_2$O$_3$ aqueous solution and brine, dried over MgSO$_4$. The crude product was directly used for next step. A mixture of above product (1.0 eqv), K$_2$CO$_3$ (3.0 eqv) and 7-hydroxycoumarin (2.0 eqv) in acetonitrile was stirred at room temperature for 2.5 hrs. Solvent was subsequently removed under reduced pressure and the residue was dissolved in water and extracted with ethyl acetate. The combined organic layers were washed with Na$_2$S$_2$O$_3$ aqueous solution and brine, dried over MgSO$_4$. Flash chromatography on a short silica gel column was used to remove inorganic impurities and most of the excess 7-hydroxycoumarin. The resulting compound 4, which contains two isomers, was dissolved in CH$_2$Cl$_2$ and 3-chloroperoxybenzoic acid (m-CPBA, 68%, 1.0 eqv) was then added in several ports at 0° C. After being stirred at 0° C. for 30 min (monitored with TLC), the reaction mixture was diluted with CH$_2$Cl$_2$ and washed with Na$_2$S$_2$O$_3$ (aq.), NaHCO$_3$ (aq.) and brine subsequently. Drying over MgSO$_4$ was followed by purification with flash chromatography on a short silica gel column to afford compound 5. To a mixture of compound 5 (1.0 eqv) and NaI (5.0 eqv) in anhydrous acetone at 0° C. was added dropwise trifluoroacetic anhydride (TFAA) (5.0 eqv). The resulting mixture was stirred at 0° C. for 1 h and then the solvent and volatile reagent was removed under reduced pressure. The residue was dissolved in NaHCO$_3$ (aq.) and extracted with ethyl acetate. After purification with flash chromatography on a silica gel column, the title compound 6 was obtained as solid. Embodiments of the compound 6 (compounds 6-1 to 6-6) were synthesized by using the alcohols methanol, ethanol, isopropanol, tert-butanol, benzyl alcohol, and tosyl acid, respectively, respectively:

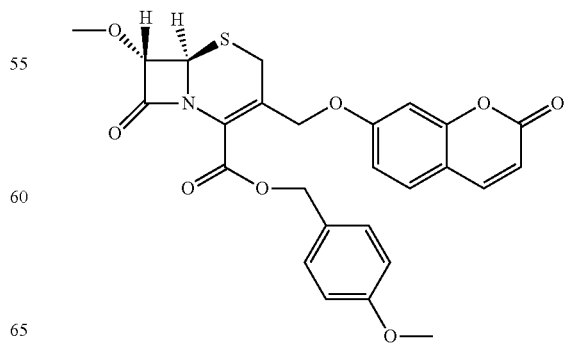

(6R,7S)-4-methoxybenzyl 7-methoxy-8-oxo-3-(((2-oxo-2H-chromen-7-yl)oxy)methyl)-5-thia-1-azabicyclo[4.2.0]oct-2-ene-2-carboxylate (6-1)

Yield=33%. $^1$H NMR (400 MHz, CDCl$_3$) 7.61 (d, J=9.5 Hz, 1H), 7.32 (d, J=8.2 Hz, 3H), 6.82 (d, J=8.7 Hz, 2H), 6.75 (dd, J=8.6, 2.4 Hz, 1H), 6.70 (d, J=2.3 Hz, 1H), 6.24 (d, J=9.5 Hz, 1H), 5.24 (s, 2H), 4.81 (q, J=12.4 Hz, 2H), 4.68 (d, J=1.7 Hz, 1H), 4.52 (d, J=1.7 Hz, 1H), 3.75 (s, 3H), 3.63 (d, J=18.3 Hz, 2H), 3.52 (s, 3H), 3.46 (d, J=18.3 Hz, 2H). $^{13}$C NMR (101 MHz, CDCl$_3$) δ 161.34, 160.15, 155.88, 143.50, 131.00, 129.19, 126.94, 122.72, 114.20, 113.81, 113.34, 112.79, 102.09, 90.32, 68.47, 67.29, 58.47, 56.29, 55.51, 27.82.

(6R,7S)-4-methoxybenzyl 7-isopropoxy-8-oxo-3-(((2-oxo-2H-chromen-7-yl)oxy)methyl)-5-thia-1-azabicyclo[4.2.0]oct-2-ene-2-carboxylate (6-3)

Yield=29%. $^1$H NMR (400 MHz, CDCl$_3$) δ 7.64 (d, J=9.5 Hz, 1H), 7.43-7.27 (m, 3H), 6.86 (dd, J=10.8, 5.4 Hz, 2H), 6.80-6.69 (m, 2H), 6.28 (dd, J=9.5, 2.6 Hz, 1H), 5.26 (dt, J=16.6, 8.4 Hz, 2H), 4.96-4.79 (m, 2H), 4.74 (dd, J=25.3, 1.8 Hz, 1H), 4.58 (dd, J=21.2, 1.8 Hz, 1H), 3.78 (s, 3H), 3.64 (d, J=7.3 Hz, 1H), 3.58 (d, J=17.2 Hz, 1H), 3.46 (d, J=18.3 Hz, 1H), 1.24 (dd, J=18.7, 6.1 Hz, 6H). $^{13}$C NMR (101 MHz, CDCl$_3$) δ 167.89, 162.69, 161.47, 160.14, 155.66, 144.40, 131.08, 131.01, 129.33, 127.08, 126.87, 123.25, 114.27, 114.23, 113.48, 113.38, 113.29, 102.15, 87.76, 74.92, 68.58, 67.31, 58.40, 55.52, 27.84, 22.63, 22.52.

6-2

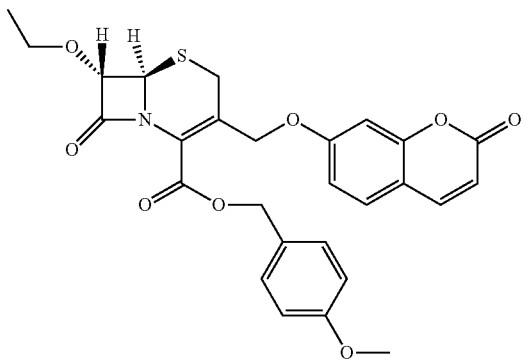

6-4

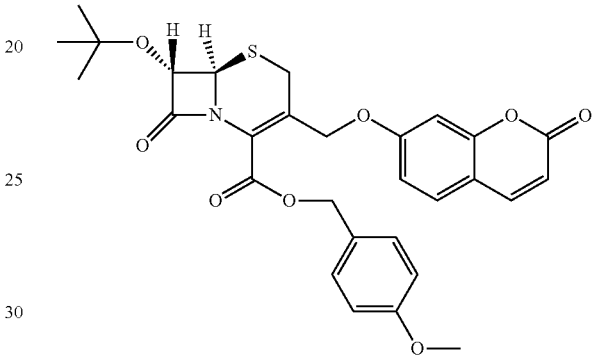

(6R,7S)-4-methoxybenzyl 7-ethoxy-8-oxo-3-(((2-oxo-2H-chromen-7-yl)oxy)methyl)-5-thia-1-azabicyclo[4.2.0]oct-2-ene-2-carboxylate (6-2)

Yield=30%. $^1$H NMR (400 MHz, CDCl$_3$) δ 7.63 (d, J=9.6 Hz, 1H), 7.34 (dd, J=8.6, 3.1 Hz, 3H), 6.84 (d, J=8.7 Hz, 2H), 6.76 (dd, J=8.6, 2.5 Hz, 1H), 6.72 (d, J=2.3 Hz, 1H), 6.27 (d, J=9.5 Hz, 1H), 5.25 (d, J=1.8 Hz, 2H), 4.82 (q, J=12.5 Hz, 2H), 4.67 (d, J=1.8 Hz, 1H), 4.56 (d, J=1.8 Hz, 1H), 3.77 (s, 3H), 3.76-3.62 (m, 2H), 3.62 (d, J=18.3 Hz, 1H), 3.46 (d, J=18.3 Hz, 1H), 1.26 (t, J=7.0 Hz, 3H). $^{13}$C NMR (101 MHz, CDCl$_3$) δ 171.30, 161.71, 161.62, 161.23, 160.17, 155.91, 143.45, 131.04, 129.15, 126.92, 122.53, 114.21, 113.87, 113.35, 112.77, 102.16, 89.19, 68.48, 67.32, 67.25, 60.65, 57.03, 55.51, 27.83, 15.34.

(6R,7S)-4-methoxybenzyl 7-(tert-butoxy)-8-oxo-3-(((2-oxo-2H-chromen-7-yl)oxy)methyl)-5-thia-1-azabicyclo[4.2.0]oct-2-ene-2-carboxylate (6-4)

Yield=33%. $^1$H NMR (400 MHz, CDCl$_3$) δ 7.62 (d, J=9.5 Hz, 1H), 7.34 (t, J=8.0 Hz, 3H), 6.84 (d, J=8.5 Hz, 2H), 6.79-6.71 (m, 2H), 6.26 (d, J=9.5 Hz, 1H), 5.28-5.19 (m, 2H), 4.85-4.75 (m, 2H), 4.65 (d, J=1.4 Hz, 1H), 4.55 (d, J=1.4 Hz, 1H), 3.77 (s, 3H), 3.61 (d, J=18.1 Hz, 1H), 3.46 (dd, J=9.4, 8.8 Hz, 2H), 1.26 (s, 9H). $^{13}$C NMR (101 MHz, CDCl$_3$) δ 171.37, 167.94, 162.76, 161.74, 161.18, 161.09, 160.17, 158.79, 155.89, 143.45, 131.02, 129.19, 127.34, 126.89, 126.57, 125.21, 122.18, 114.22, 113.86, 113.38, 112.74, 102.15, 83.25, 68.57, 67.12, 61.35, 59.11, 55.51, 28.09, 21.29.

6-3

6-5

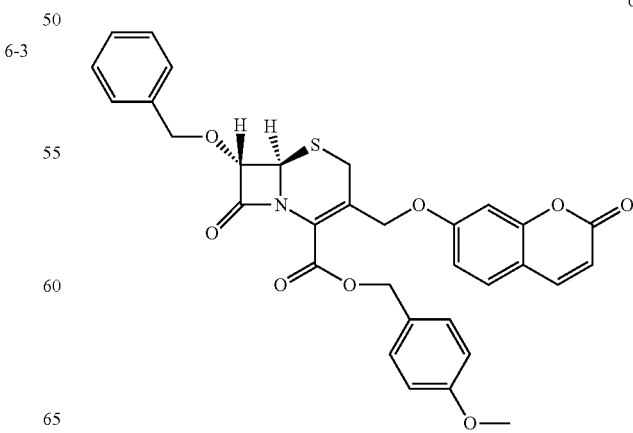

(6R,7S)-4-methoxybenzyl 7-(benzyloxy)-8-oxo-3-(((2-oxo-2H-chromen-7-yl)oxy)methyl)-5-thia-1-azabicyclo[4.2.0]oct-2-ene-2-carboxylate (6-5)

Yield=23%. ¹H NMR (400 MHz, CDCl₃) δ 7.62 (d, J=9.5 Hz, 1H), 7.36 (d, J=0.5 Hz, 4H), 7.33 (s, 1H), 7.33 (d, J=3.2 Hz, 1H), 6.85 (d, J=8.7 Hz, 3H), 6.80-6.64 (m, 3H), 6.27 (d, J=9.5 Hz, 1H), 5.26 (d, J=1.5 Hz, 2H), 4.87 (t, J=3.8 Hz, 1H), 4.83 (d, J=4.1 Hz, 1H), 4.80 (d, J=3.1 Hz, 1H), 4.79-4.76 (m, 1H), 4.64 (d, J=1.8 Hz, 1H), 4.59 (d, J=1.8 Hz, 1H), 3.77 (s, 3H), 3.58 (d, J=18.2 Hz, 1H), 3.42 (d, J=18.3 Hz, 1H). ¹³C NMR (101 MHz, CDCl₃) δ 161.59, 161.50, 161.22, 161.16, 160.18, 155.91, 143.42, 136.23, 131.05, 129.14, 128.94, 128.79, 128.60, 126.92, 122.93, 114.26, 114.22, 113.88, 113.36, 112.74, 102.17, 88.52, 83.92, 73.55, 68.49, 67.28, 57.12, 55.51, 27.75.

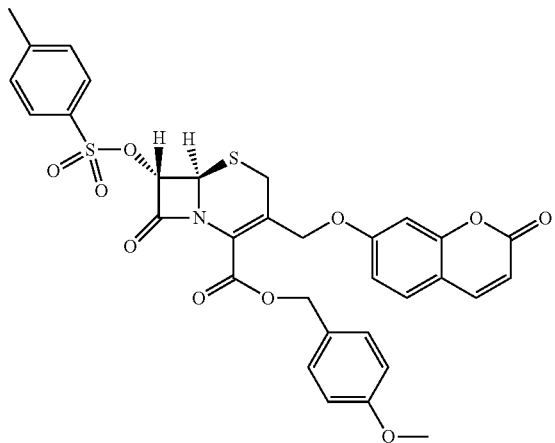

(6R,7S)-4-methoxybenzyl 8-oxo-3-(((2-oxo-2H-chromen-7-yl)oxy)methyl)-7-(tosyloxy)-5-thia-1-azabicyclo[4.2.0]oct-2-ene-2-carboxylate (6-6)

Yield=12%. ¹H NMR (400 MHz, CDCl₃) δ 8.01 (s, 1H), 7.84 (d, J=8.5 Hz, 2H), 7.63 (d, J=9.6 Hz, 1H), 7.42-7.27 (m, 5H), 6.85 (d, J=8.7 Hz, 2H), 6.76 (dd, J=8.6, 2.5 Hz, 1H), 6.72 (d, J=2.4 Hz, 1H), 6.28 (d, J=9.5 Hz, 1H), 5.28-5.17 (m, 2H), 5.12 (d, J=1.8 Hz, 1H), 4.86 (q, J=12.7 Hz, 2H), 4.78 (d, J=1.7 Hz, 1H), 4.62 (s, 1H), 3.78 (s, 3H), 3.62 (d, J=18.3 Hz, 1H), 3.46 (d, J=18.3 Hz, 1H), 2.47 (s, 3H).

Example 7

Preparation of Final Fluorescent Probes

To a solution of CH₂Cl₂:TFA:TIPS:H₂O=30:65:2.5:2.5 (4 mL) was added compound 6 and the mixture was stirred at 0° C. for 30 min (monitored with HPLC). RP-HPLC purification on a C18 column afforded the desired final probes.

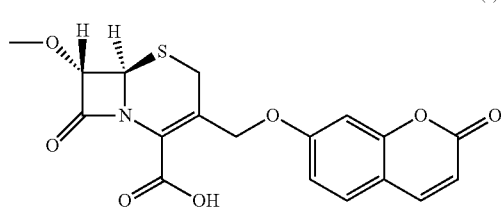

(6R,7S)-7-methoxy-8-oxo-3-(((2-oxo-2H-chromen-7-yl)oxy)methyl)-5-thia-1-azabicyclo[4.2.0.]oct-2-ene-2-carboxylic Acid ((s)-CC-1)

Yield=77%. ¹H NMR (400 MHz, d₆-DMSO) δ 7.97 (d, J=9.6 Hz, 1H), 7.62 (d, J=8.6 Hz, 1H), 7.01 (d, J=2.2 Hz, 1H), 6.95 (dd, J=8.6, 2.4 Hz, 1H), 6.28 (d, J=9.5 Hz, 1H), 5.01 (d, J=1.6 Hz, 1H), 4.86 (dd, J=26.5, 11.9 Hz, 2H), 4.75 (d, J=1.7 Hz, 1H), 3.70 (d, J=18.1 Hz, 1H), 3.55 (d, J=18.1 Hz, 1H), 3.43 (s, 3H). ¹³C NMR (101 MHz, d₆-DMSO) δ 163.45, 161.94, 161.80, 160.89, 155.93, 144.93, 132.96, 130.26, 128.14, 121.16, 113.46, 102.18, 89.60, 67.80, 57.99, 55.90, 27.65. MS: Calculated for C₁₈H₁₅NNaO₇S⁺ ([M−H]⁺): 412.37. Found: 412.06.

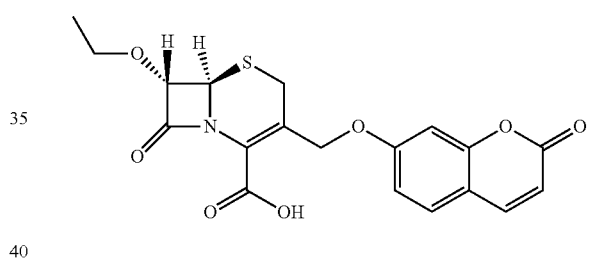

(6R,7S)-7-ethoxy-8-oxo-3-(((2-oxo-2H-chromen-7-yl)oxy)methyl)-5-thia-1-azabicyclo[4.2.0]oct-2-ene-2-carboxylic Acid ((s)-CC-2)

Yield=80%. ¹H NMR (400 MHz, d₆-DMSO) δ 7.98 (d, J=9.6 Hz, 1H), 7.63 (d, J=8.6 Hz, 1H), 7.01 (d, J=2.4 Hz, 1H), 6.96 (dd, J=8.6, 2.4 Hz, 1H), 6.29 (d, J=9.5 Hz, 1H), 4.95 (d, J=1.6 Hz, 1H), 4.85 (d, J=15.7 Hz, 2H), 4.77 (d, J=1.4 Hz, 1H), 3.74-3.65 (m, 2H), 3.62 (d, J=7.0 Hz, 1H), 3.55 (d, J=18.1 Hz, 1H), 1.16 (t, J=7.0 Hz, 3H). MS: Calculated for C₁₉H₁₆NO₇S⁻ ([M−H]⁻): 402.41. Found: 402.00.

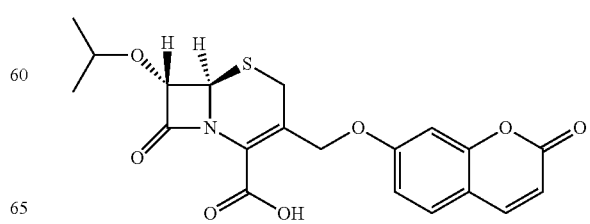

(6R,7S)-7-isopropoxy-8-oxo-3-(((2-oxo-2H-chromen-7-yl)oxy)methyl)-5-thia-1-azabicyclo[4.2.0]oct-2-ene-2-carboxylic Acid ((s)-CC-3)

Yield=83%. $^1$H NMR (400 MHz, d$_6$-DMSO) δ 7.98 (d, J=9.2 Hz, 1H), 7.62 (d, J=8.7 Hz, 1H), 7.01 (d, J=2.4 Hz, 1H), 6.95 (dd, J=8.6, 2.5 Hz, 1H), 6.29 (d, J=9.5 Hz, 1H), 4.89 (d, J=11.9 Hz, 1H), 4.84 (d, J=1.7 Hz, 1H), 4.81 (d, J=11.9 Hz, 1H), 4.77 (d, J=1.7 Hz, 1H), 3.82 (dd, J=12.2, 6.1 Hz, 1H), 3.70 (d, J=18.0 Hz, 1H), 3.54 (d, J=18.1 Hz, 1H), 1.15 (dd, J=9.3, 6.1 Hz, 6H). $^{13}$C NMR (101 MHz, d$_6$-DMSO) δ 163.48, 162.50, 161.81, 160.90, 155.94, 144.95, 130.26, 128.23, 121.00, 113.48, 102.19, 87.32, 74.02, 67.80, 58.05, 40.81, 40.60, 40.39, 40.18, 39.97, 39.77, 39.56, 27.67, 22.97, 22.89. MS: Calculated for $C_{20}H_{18}NO_7S^-$ ([M–H]$^-$): 416.43. Found: 416.03.

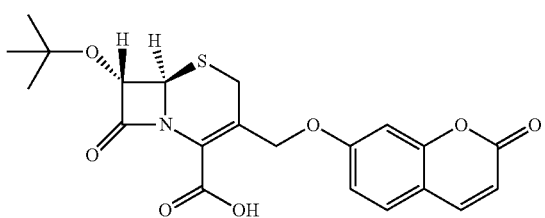

(s)-CC-4

(6R,7S)-7-(tert-butoxy)-8-oxo-3-(((2-oxo-2H-chromen-7-yl)oxy)methyl)-5-thia-1-azabicyclo[4.2.0]oct-2-ene-2-carboxylic Acid ((s)-CC-4)

Yield=75%. $^1$H NMR (400 MHz, d$_6$-DMSO) δ 7.98 (d, J=9.2 Hz, 1H), 7.62 (d, J=8.7 Hz, 1H), 7.01 (d, J=2.4 Hz, 1H), 6.95 (dd, $^1$H NMR (400 MHz, DMSO) δ 7.98 (d, J=9.6 Hz, 1H), 7.62 (d, J=8.7 Hz, 1H), 7.01 (d, J=2.3 Hz, 1H), 6.98-6.92 (m, 1H), 6.29 (d, J=9.5 Hz, 1H), 4.89 (d, J=12.0 Hz, 1H), 4.83 (d, J=1.7 Hz, 1H), 4.80 (s, 1H), 4.76 (d, J=1.6 Hz, 1H), 3.68 (d, J=18.0 Hz, 1H), 3.53 (d, J=18.0 Hz, 1H), 1.19 (s, 9H). $^{13}$C NMR (101 MHz, d$_6$-DMSO) δ 163.53, 163.14, 161.81, 160.91, 155.93, 144.96, 130.26, 121.16, 113.50, 102.19, 82.72, 76.56, 67.79, 59.09, 28.16, 27.61. MS: Calculated for $C_{21}H_{20}NO_7S^-$ ([M–H]$^-$): 430.46. Found: 430.00.

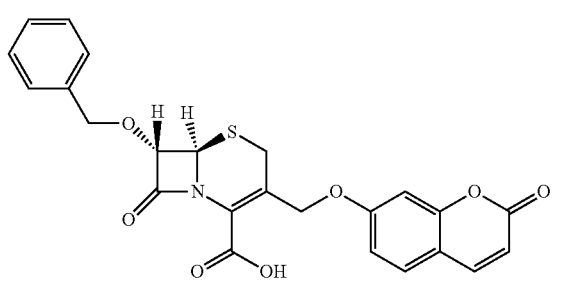

(s)-CC-5

(6R,7S)-7-(benzyloxy)-8-oxo-3-(((2-oxo-2H-chromen-7-yl)oxy)methyl)-5-thia-1-azabicyclo[4.2.0]oct-2-ene-2-carboxylic Acid ((s)-CC-5)

Yield=72%. $^1$H NMR (400 MHz, d$_6$-DMSO) δ 7.98 (d, J=9.4 Hz, 1H), 7.63 (d, J=8.4 Hz, 1H), 7.36 (dd, J=12.8, 4.2 Hz, 4H), 7.01 (s, 1H), 6.95 (d, J=8.9 Hz, 1H), 6.29 (d, J=9.5 Hz, 1H), 4.94 (s, 1H), 4.91 (s, 1H), 4.87 (d, J=1.7 Hz, 1H), 4.82 (d, J=11.9 Hz, 1H), 4.73 (d, J=11.4 Hz, 1H), 4.63 (d, J=11.5 Hz, 1H), 3.60 (dd, J=52.7, 18.1 Hz, 2H). $^{13}$C NMR (101 MHz, CD$_3$OD) δ 162.23, 146.95, 144.47, 143.24, 129.39, 128.46, 128.31, 128.24, 126.45, 124.31, 113.02, 112.59, 101.55, 88.27, 72.94, 67.09, 56.94, 26.94. MS: Calculated for $C_{24}H_{18}NO_7S^-$ ([M–H]$^-$): 464.48. Found: 464.17.

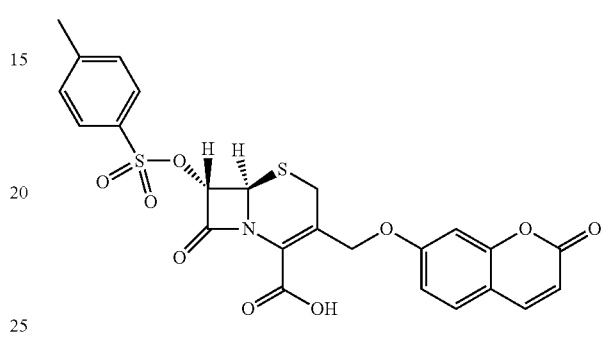

(s)-CC-6

(6R,7S)-8-oxo-3-(((2-oxo-2H-chromen-7-yl)oxy)methyl)-7-(tosyloxy)-5-thia-1-azabicyclo[4.2.0]oct-2-ene-2-carboxylic Acid ((s)-CC-6)

Yield=70%. $^1$H NMR (400 MHz, d$_6$-DMSO) δ 7.98 (d, J=9.5 Hz, 1H), 7.88 (d, J=8.4 Hz, 2H), 7.62 (d, J=8.6 Hz, 1H), 7.52 (d, J=8.4 Hz, 2H), 7.00 (d, J=2.4 Hz, 1H), 6.94 (dd, J=8.6, 2.4 Hz, 1H), 6.29 (d, J=9.5 Hz, 1H), 5.62 (d, J=1.5 Hz, 1H), 5.06 (d, J=1.7 Hz, 1H), 4.90 (dd, J=36.4, 12.3 Hz, 2H), 3.60 (dd, J=41.3, 18.1 Hz, 3H), 2.43 (s, 3H). MS: Calculated for $C_{24}H_{18}NO_9S_2^-$ ([M–H]$^-$): 528.54. Found: 527.88.

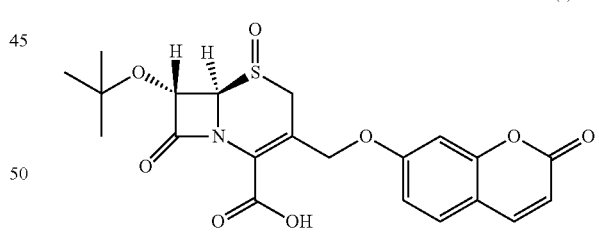

(s)-CC-7

(6R,7S)-7-(tert-butoxy)-8-oxo-3-(((2-oxo-2H-chromen-7-yl)oxy)methyl)-5-thia-1-azabicyclo[4.2.0]oct-2-ene-2-carboxylic acid 5-oxide ((s)-CC-7)

$^1$H NMR (400 MHz, CD$_3$OD) δ 7.87 (d, J=9.6 Hz, 1H), 7.54 (d, J=8.4 Hz, 1H), 6.95 (dd, J=11.6, 3.1 Hz, 2H), 6.25 (d, J=9.5 Hz, 1H), 5.44-4.98 (m, 2H), 4.61 (d, J=50.3 Hz, 2H), 4.15 (d, J=16.5 Hz, 1H), 4.06 (d, J=18.8 Hz, 1H), 3.90 (d, J=16.0 Hz, 1H), 3.74-3.59 (m, 1H), 1.31 (s, 1H). MS: Calculated for $C_{21}H_{20}NO_8S$ ([M–H]$^-$): 446.46. Found: 445.98.

Example 8

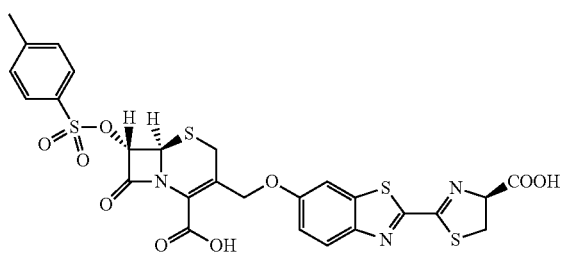

(s)-CL-6

$^1$H NMR (400 MHz, DMSO) δ 8.09 (d, J=9.1 Hz, 1H), 7.98 (s, 1H), 7.86 (d, J=7.8 Hz, 2H), 7.51 (d, J=8.1 Hz, 2H), 7.32 (dd, J=9.2, 1.6 Hz, 1H), 5.41 (s, 1H), 4.96 (dd, J=25.3, 11.6 Hz, 2H), 4.84 (s, 1H), 3.52 (d, J=17.4 Hz, 1H), 3.35 (d, J=17.0 Hz, 4H), 2.42 (s, 3H). $^{13}$C NMR (101 MHz, CD$_3$OD) δ 172.08, 166.42, 162.95, 158.54, 157.99, 157.77, 147.87, 146.62, 137.69, 131.99, 130.37, 128.19, 127.43, 126.52, 124.76, 117.30, 105.14, 84.02, 78.20, 67.01, 57.19, 48.50, 48.29, 48.08, 47.87, 47.65, 47.44, 47.23, 34.79, 26.87, 20.66. MS: Calculated for C$_{26}$H$_{21}$N$_3$O$_9$S$_4$ ([M+H$^+$]): 648.02. Found: 648.40.

Example 9

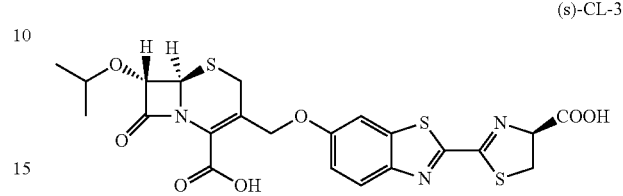

(s)-CL-3

$^1$H NMR (400 MHz, DMSO) δ 8.04 (d, J=9.1 Hz, 1H), 7.79 (d, J=2.3 Hz, 1H), 7.20 (dd, J=9.1, 2.5 Hz, 1H), 5.47-5.36 (m, 1H), 4.88-4.82 (m, 2H), 4.77 (d, J=1.0 Hz, 1H), 3.88-3.80 (m, 1H), 3.80-3.75 (m, 1H), 3.73 (s, 1H), 3.68 (d, J=8.3 Hz, 1H), 3.58 (d, J=18.1 Hz, 2H), 1.15 (dd, J=8.7, 6.1 Hz, 6H). MS: Calculated for C$_{22}$H$_{21}$N$_3$O$_7$S$_3$([M+H]$^+$): 536.05. Found: 536.40.

---

The invention claimed is:

1. A probe selectively cleavable by a metallo-β-lactamase, wherein said probe consists of an isolated cephalosporin enantiomer having a 6,7-trans configuration and a detectable label attached thereto, wherein the probe has the formula I or formula II:

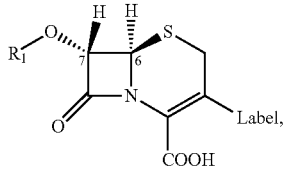

I

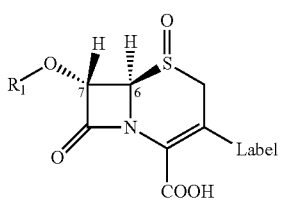

II wherein:

R$_1$ is selected from the group consisting of: methyl, ethyl, isopropyl, tert-butyl, benzyl-, and tosyl, and wherein the detectable label is (2-oxo-2H-chromen-7-yl) (III) or (4S)-2-(6-oxo-1,3-benzothiazol-2-yl)-4,5-dihydrothiazole-4-carboxylic acid (IV) having the structures:

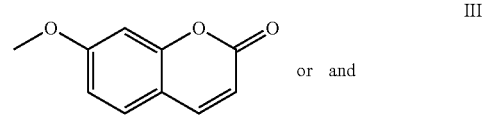

III or and

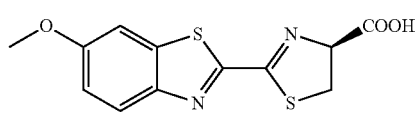

IV

2. The composition of claim 1, wherein the probe is selected from the group consisting of:

(s)-CC-1

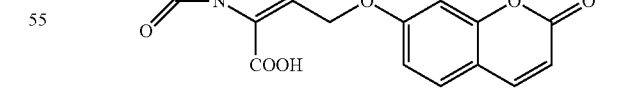

(s)-CC-2

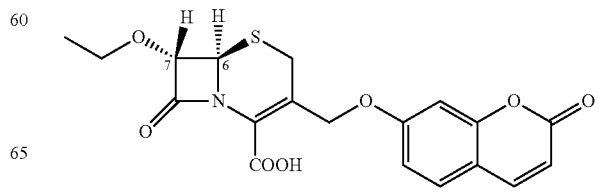

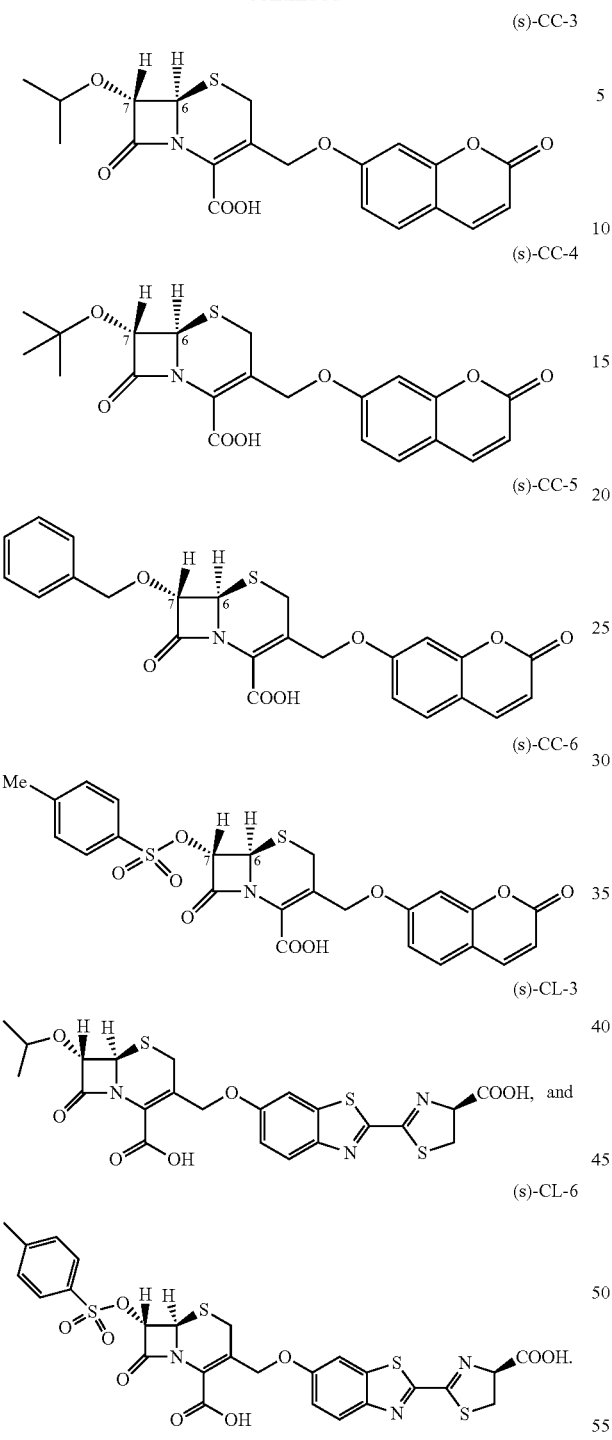

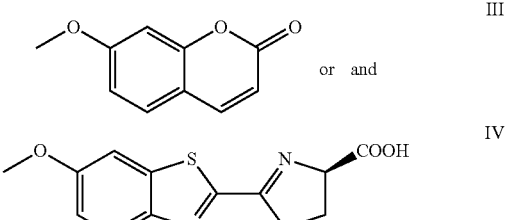

wherein:

R$_1$ is selected from the group consisting of: methyl, ethyl, isopropyl, tert-butyl, benzyl-, and tosyl, and wherein the detectable label is (2-oxo-2H-chromen-7-yl) (III) or (4S)-2-(6-oxo-1,3-benzothiazol-2-yl)-4,5-dihydrothiazole-4-carboxylic acid (IV) having the structures:

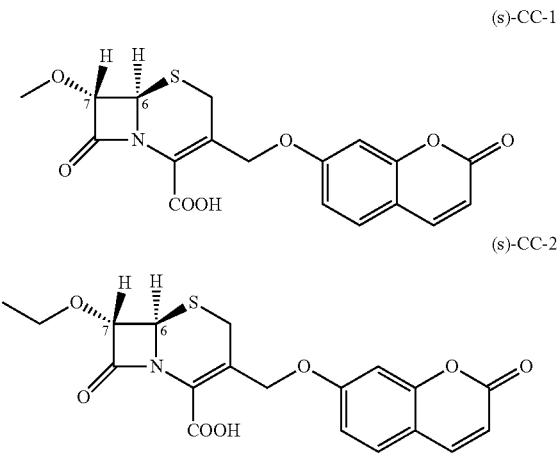

allowing an effective period for a metallo-β-lactamase activity to cleave the cephalosporin moiety, thereby releasing the detectable label from the cephalosporin moiety, whereby a detectable signal is generated; and detecting the signal, wherein a detectable signal indicates that the sample contains a metallo-β-lactamase activity or a source of a metallo-β-lactamase activity.

4. The method of claim 3, wherein the probe is selected from the group consisting of:

3. A method of selectively detecting a metallo-β-lactamase activity, said method comprising contacting a sample suspected of having a metallo-β-lactamase activity with a probe selectively cleavable by a metallo-β-lactamase, wherein said probe consists of an isolated cephalosporin enantiomer having a 6,7-trans configuration and a detectable label attached thereto, wherein the probe has the formula I or formula II:

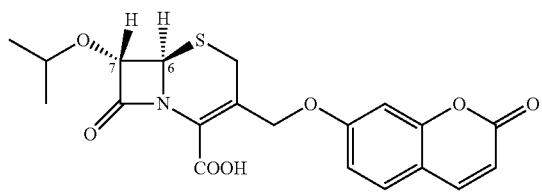
(s)-CC-3
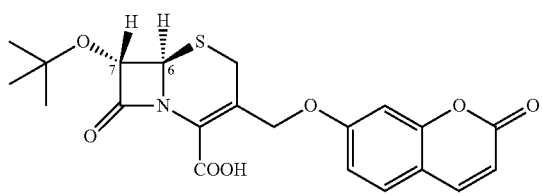
(s)-CC-4
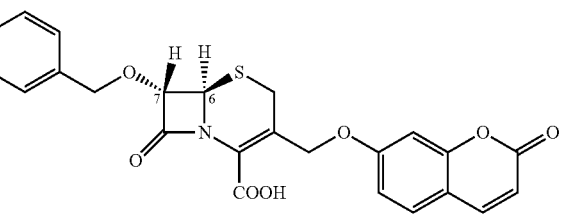
(s)-CC-5
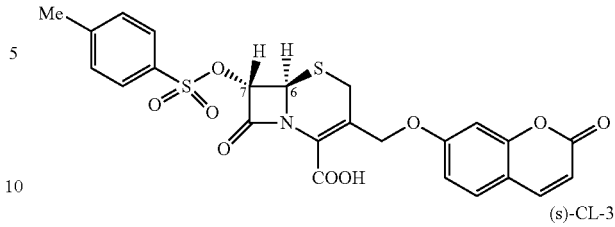
(s)-CC-6
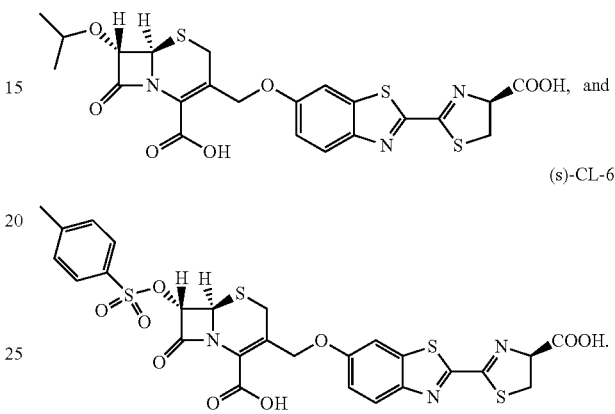
(s)-CL-3
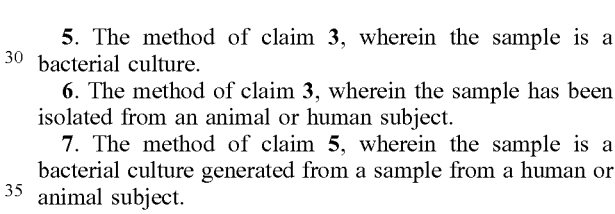
(s)-CL-6
5. The method of claim 3, wherein the sample is a bacterial culture.
6. The method of claim 3, wherein the sample has been isolated from an animal or human subject.
7. The method of claim 5, wherein the sample is a bacterial culture generated from a sample from a human or animal subject.
* * * * *

SEQUENCE LISTING

<160> NUMBER OF SEQ ID NOS: 18

<210> SEQ ID NO 1
<211> LENGTH: 801
<212> TYPE: DNA
<213> ORGANISM: Artificial sequence
<220> FEATURE:
<223> OTHER INFORMATION: Beta-lactamase VIM-27 Genbank Accession No: HQ858608.1

<400> SEQUENCE: 1

```
atgttaaaag ttattagtag tttattggtc tacatgaccg cgtctgtcat ggctgtcgca      60
agtccgttag cccattccgg ggagccgagt ggtgagtatc cgacagtcaa cgaaattccg     120
gtcggagagg tccgacttta ccagattgcc gatggtgttt ggtcgcatat ctcaacgcag     180
tcgtttgatg gcgcggtcta cccgtccaat ggtctcattg tccgtgatgg tgatgagttg     240
cttttgattg atacagcgtg gggtgcgaaa acacagcgg cacttctcgc ggagattgaa      300
aagcaaattg gacttcccgt aacgcgtgca gtctccacgc actttcatga cgaccgcgtc     360
ggcggcgttg atgtccttcg ggcggctggg gtggcaacgt acgcatcacc gtcgacacgc     420
cggctagccg aggcagaggg gaacgagatt cccacgcatt ctctagaagg actctcatcg     480
agcggggacg cagtgcgctt cggtccagta gagctcttct atcctggtgc tgcgcattcg     540
accgacaatc tggttgtata cgtcccgtca gcgaacgtgc tataeggtgg ttgtgccgtt     600
catgagttgt caagcacgtc tgcggggaac gtggccgatg ccgatctggc tgaatggccc     660
acctccgttg agcggattca aaaacactac ccggaagcag aggtcgtcat tcccgggcac     720
ggtctaccgg gcggtctaga cttgctccag cacacagcga acgttgtcaa agcacacaaa     780
aatcgctcag tcgccgagta g                                               801
```

<210> SEQ ID NO 2
<211> LENGTH: 780
<212> TYPE: DNA
<213> ORGANISM: Artificial sequence
<220> FEATURE:
<223> OTHER INFORMATION: Beta-lactamase IMP-1 Genbank Accession No:

KC200566.1

<400> SEQUENCE: 2

| | | | | | |
|---|---|---|---|---|---|
| aaaaggaaaa | gtatgagcaa | gttatctgta | ttctttatat | ttttgttttg | cagcattgct | 60 |
| accgcagcag | agtctttgcc | agatttaaaa | attgaaaagc | ttgatgaagg | cgtttatgtt | 120 |
| catacttcgt | ttgaagaagt | taacgggtgg | ggcgttgttc | ctaaacatgg | tttggtggtt | 180 |
| cttgtaaatg | ctgaggctta | cctaattgac | actccattta | cggctaaaga | tactgaaaag | 240 |
| ttagtcactt | ggtttgtgga | gcgtggctat | aaaataaaag | gcagcatttc | ctctcatttt | 300 |
| catagcgaca | gcacgggcgg | aatagagtgg | cttaattctc | gatctatccc | cacgtatgca | 360 |
| tctgaattaa | caaatgaact | gcttaaaaaa | gacggtaagg | ttcaagccac | aaattcattt | 420 |
| agcggagtta | actattggct | agttaaaaat | aaaattgaag | ttttttatcc | aggcccggga | 480 |
| cacactccag | ataacgtagt | ggtttggttg | cctgaaagga | aatattatt | cggtggttgt | 540 |
| tttattaaac | cgtacggttt | aggcaatttg | ggtgacgcaa | atatagaagc | ttggccaaag | 600 |
| tccgccaaat | tattaaagtc | caaatatggt | aaggcaaaac | tggttgttcc | aagtcacagt | 660 |
| gaagttggag | acgcatcact | cttgaaactt | acattagagc | aggcggttaa | agggttaaac | 720 |
| gaaagtaaaa | aaccatcaaa | accaagcaac | taaatttcta | acaagtcgtt | gcagcacgcc | 780 |

<210> SEQ ID NO 3
<211> LENGTH: 900
<212> TYPE: DNA
<213> ORGANISM: Artificial sequence
<220> FEATURE:
<223> OTHER INFORMATION: Beta-lactamase NDM-1 Genbank Accession No:
AF059836.1

<400> SEQUENCE: 3

| | | | | | |
|---|---|---|---|---|---|
| gattgggggt | gacgtggtca | gccatggctc | agcgcagctt | gtcggccatg | cgggccgtat | 60 |
| gagtgattgc | ggcgcggcta | tcggggcgg | aatggctcat | cacgatcatg | ctggccttgg | 120 |
| ggaacgccgc | accaaacgcg | cgcgctgacg | cggcgtagtg | ctcagtgtcg | gcatcaccga | 180 |
| gattgccgag | cgacttggcc | ttgctgtcct | tgatcaggca | gccaccaaaa | gcgatgtcgg | 240 |
| tgccgtcgat | cccaacggtg | atattgtcac | tggtgtggcc | ggggccgggg | taaaatacct | 300 |
| tgagcgggcc | aaagttgggg | gcggttgctg | gttcgaccca | gccattggcg | gcgaaagtca | 360 |
| ggctgtgttg | cgccgcaacc | atcccctctt | gcggggcaag | ctggttcgac | aacgcattgg | 420 |
| cataagtcgc | aatccccgcc | gcatgcagcg | cgtccatacc | gcccatcttg | tcctgatgcg | 480 |
| cgtgagtcac | caccgccagc | gcgaccggca | ggttgatctc | ctgcttgatc | cagttgagga | 540 |
| tctgggcggt | ctggtcatcg | gtccaggcgg | tatcgaccac | cagcacgcgg | ccgccatccc | 600 |
| tgacgatcaa | accgttggaa | gcgactgccc | cgaaacccgg | catgtcgaga | taggaagtgt | 660 |
| gctgccagac | attcggtgcg | agctggcgga | aaaccagatc | gccaaaccgt | tggtcgccag | 720 |
| tttccatttg | ctggccaatc | gtcggcgga | tttcaccggg | catgcacccg | ctcagcatca | 780 |
| atgcagcggc | taatgcggtg | ctcagcttcg | cgaccgggtg | cataatattg | ggcaattcca | 840 |
| tcaagttttc | cttttattca | gcattaaaaa | ccccgcaaat | gcgaggccta | gtaaatagat | 900 |

<210> SEQ ID NO 4
<211> LENGTH: 1146
<212> TYPE: DNA
<213> ORGANISM: Artificial sequence
<220> FEATURE:
<223> OTHER INFORMATION: Beta-lactamase KPC-1 Genbank Accession No:
NC_019155.1

<400> SEQUENCE: 4

```
tcaggcgagg tggccgaccc atgaacgccg acctgattcg tttttcaagc tcggtgataa      60
tcccagctgt agcggcctga ttacatccgg ccgctacacc tagctccacc ttcaaacaag     120
gaatatcgtt gatgtcactg tatcgccgtc tagttctgct gtcttgtctc tcatggccgc     180
tggctggctt ttctgccacc gcgctgacca acctcgtcgc ggaaccattc gctaaactcg     240
aacaggactt tggcggctcc atcggtgtgt acgcgatgga taccggctca ggcgcaactg     300
taagttaccg cgctgaggag cgcttcccac tgtgcagctc attcaagggc tttcttgctg     360
ccgctgtgct ggctcgcagc cagcagcagg ccggcttgct ggacacaccc atccgttacg     420
gcaaaaatgc gctggttccg tggtcaccca tctcggaaaa atatctgaca acaggcatga     480
cggtggcgga gctgtccgcg gccgccgtgc aatacagtga taacgccgcc gccaatttgt     540
tgctgaagga gttgggcggc ccggccgggc tgacggcctt catgcgctct atcggcgata     600
ccacgttccg tctggaccgc tgggagctgg agctgaactc cgccatccca ggcgatgcgc     660
gcgataccte atcgccgcgc gccgtgacgg aaagcttaca aaaactgaca ctgggctctg     720
cactggctgc gccgcagcgg cagcagtttg ttgattggct aaagggaaac acgaccggca     780
accaccgcat ccgcgcggcg gtgccggcag actgggcagt cggagacaaa accggaacct     840
gcggagtgta tggcacggca aatgactatg ccgtcgtctg gcccactggg cgcgcaccta     900
tgtgttggc cgtctacacc cgggcgccta acaaggatga caagtacagc gaggccgtca     960
tcgccgctgc ggctagactc gcgctcgagg gattgggcgt caacgggcag taaggctctg    1020
aaaatcatct attggcccac caccgccgcc cttgcgggcg gcatggatta ccaaccactg    1080
tcacatttag gctaggagtc tgcgcggcag agccgtgtga ccggttttct gtagagcact    1140
gacgat                                                              1146
```

<210> SEQ ID NO 5
<211> LENGTH: 820
<212> TYPE: DNA
<213> ORGANISM: Artificial sequence
<220> FEATURE:
<223> OTHER INFORMATION: Beta-lactamase OXA-48

<400> SEQUENCE: 5

```
acttctaggg aataatttt tcctgtttga gcacttcttt tgtgatggct tggcgcagcc      60
ctaaaccatc cgatgtgggc atatccatat tcatcgcaaa aaaccacaca ttatcatcaa     120
gttcaaccca accgacccac cagccaatct taggttcgat tctagtcgag tatccagttt     180
tagcccgaat aatatagtca ccattggctt cggtcagcat ggcttgtttg acaatacgct     240
ggctgcgctc cgatacgtgt aacttattgt gatacagctt tcttaaaaag ctgatttgct     300
ccgtggccga aattcgaata ccaccgtcga gccagaaact gtctacattg cccgaaatgt     360
cctcattacc ataatcgaaa gcatgtagca tcttgctcat acgtgcctcg ccaatttggc     420
gggcaaattc ttgataaaca ggcacaactg aatatttcat cgcggtgatt agattatgat     480
cgcgattcca gtggcgata tcgcgcgtct gtccatccca cttaaagact tggtgttcat     540
ccttaaccac gcccaaatcg agggcgatca agctattggg aattttaaag gtagatgcgg     600
gtaaaaatgc ttggttcgcc cgtttaagat tattggtaaa tccttgctgc ttattctcat     660
tccagagcac aactacgccc tgtgatttat gttcagtaaa gtgagcattc caacttttgt     720
tttcttgcca ttcctttgct accgcaggca ttccgataat cgatgccacc aaaaacacag     780
```

```
ccgataaggc taatacacgc ataacgtccc cttgcttaat                           820
```

<210> SEQ ID NO 6
<211> LENGTH: 1073
<212> TYPE: DNA
<213> ORGANISM: Artificial sequence
<220> FEATURE:
<223> OTHER INFORMATION: Beta-lactamase TEM-1 Genbank Accession No: KC493654.1

<400> SEQUENCE: 6

```
aaggaagagt atgagtattc aacattttcg tgtcgccctt attcccttttt ttgcggcatt    60
ttgccttcct gttttttgctc acccagaaac gctggtgaaa gtaaaagatg ctgaagatca   120
gttgggtgca cgagtgggtt acatcgaact ggatctcaac agcggtaaga tccttgagag   180
ttttcgcccc gaagaacgtt ttccaatgat gagcactttt aaagttctgc tatgtggtgc   240
ggtattatcc cgtgttgacg ccgggcaaga gcaactcggt cgccgcatac actattctca   300
gaatgacttg gttgagtact caccagtcac agaaaagcat cttacggatg gcatgacagt   360
aagagaatta tgcagtgctg ccataaccat gagtgataac actgctgcca acttacttct   420
gacaacgatc ggaggaccga aggagctaac cgcttttttg cacaacatgg gggatcatgt   480
aactcgcctt gatcgttggg aaccggagct gaatgaagcc ataccaaacg acgagcgtga   540
caccacgatg cctgcagcaa tggcaacaac gttgcgcaaa ctattaactg gcgaactact   600
tactctagct tcccggcaac aattaataga ctggatggag gcggataaag ttgcaggacc   660
acttctgcgc tcggcccttc cggctggctg gtttattgct gataaatctg gagccggtga   720
gcgtgggtct cgcggtatca ttgcagcact ggggccagat ggtaagccct cccgtatcgt   780
agttatctac acgacgggga gtcaggcaac tatggatgaa cgaaatagac agatcgctga   840
gataggtgcc tcactgatta agcattggta actgtcagac caagtttact catatatact   900
ttagattgat ttaaaacttc attttttaatt taaaaggatc taggtgaaga tcctttttga   960
taatctcatg accaaaatcc cttaacgtga gttttcgttc cactgagcgt cagacccta   1020
aggcaaaaga aacgctcgat atcatgcaag gtctttacga aactcataag ctt          1073
```

<210> SEQ ID NO 7
<211> LENGTH: 32
<212> TYPE: DNA
<213> ORGANISM: Artificial sequence
<220> FEATURE:
<223> OTHER INFORMATION: Primer NDM-1F

<400> SEQUENCE: 7

```
atttccatgg aattgcccaa tattatgcac cc                                   32
```

<210> SEQ ID NO 8
<211> LENGTH: 32
<212> TYPE: DNA
<213> ORGANISM: Artificial sequence
<220> FEATURE:
<223> OTHER INFORMATION: Primer NDM-1R

<400> SEQUENCE: 8

```
aaaagcttgt cgacgcgcag cttgtcggcc at                                   32
```

<210> SEQ ID NO 9
<211> LENGTH: 34
<212> TYPE: DNA
<213> ORGANISM: Artificial sequence
<220> FEATURE:

<223> OTHER INFORMATION: Primer KPC-3F

<400> SEQUENCE: 9
atttccatgg aatcactgta tcgccgtcta gttc                          34

<210> SEQ ID NO 10
<211> LENGTH: 34
<212> TYPE: DNA
<213> ORGANISM: Artificial sequence
<220> FEATURE:
<223> OTHER INFORMATION: Primer KPC-3R

<400> SEQUENCE: 10
aaaagcttgt cgacctgccc gttgacgccc aatc                          34

<210> SEQ ID NO 11
<211> LENGTH: 49
<212> TYPE: DNA
<213> ORGANISM: Artificial sequence
<220> FEATURE:
<223> OTHER INFORMATION: Primer VIM-27F

<400> SEQUENCE: 11
atttccatgg gattaaaagt tattagtagt ttattggtct acatgaccg          49

<210> SEQ ID NO 12
<211> LENGTH: 38
<212> TYPE: DNA
<213> ORGANISM: Artificial sequence
<220> FEATURE:
<223> OTHER INFORMATION: Primer VIM-27R

<400> SEQUENCE: 12
aaaagcttgt cgacctcggc gactgagcga tttttgtg                      38

<210> SEQ ID NO 13
<211> LENGTH: 51
<212> TYPE: DNA
<213> ORGANISM: Artificial sequence
<220> FEATURE:
<223> OTHER INFORMATION: Primer IMP-1F

<400> SEQUENCE: 13
atttccatgg gaagcaagtt atctgtattc tttatatttt tgttttgtag c       51

<210> SEQ ID NO 14
<211> LENGTH: 44
<212> TYPE: DNA
<213> ORGANISM: Artificial sequence
<220> FEATURE:
<223> OTHER INFORMATION: Primer IMP-1R

<400> SEQUENCE: 14
aaaagcttgt cgacgttgct tggttttgat ggttttttac tttc               44

<210> SEQ ID NO 15
<211> LENGTH: 36
<212> TYPE: DNA
<213> ORGANISM: Artificial sequence
<220> FEATURE:
<223> OTHER INFORMATION: Primer OXA-48F

<400> SEQUENCE: 15
atttccatgg gacgtgtatt agccttatcg gctgtg                        36

```
<210> SEQ ID NO 16
<211> LENGTH: 44
<212> TYPE: DNA
<213> ORGANISM: Artificial sequence
<220> FEATURE:
<223> OTHER INFORMATION: Primer OXA-48R

<400> SEQUENCE: 16
aaaagcttgt cgacgggaat aattttttcc tgtttgagca cttc              44

<210> SEQ ID NO 17
<211> LENGTH: 60
<212> TYPE: DNA
<213> ORGANISM: Artificial sequence
<220> FEATURE:
<223> OTHER INFORMATION: Primer TEM-1F

<400> SEQUENCE: 17
atttccatgg gccatcatca tcatcatcat agtattcaac atttccgtgt cgcccttatt    60

<210> SEQ ID NO 18
<211> LENGTH: 38
<212> TYPE: DNA
<213> ORGANISM: Artificial sequence
<220> FEATURE:
<223> OTHER INFORMATION: Primer TEM-1R

<400> SEQUENCE: 18
aaaagcttgt cgacttacca atgcttaatc agtgaggc                     38
```